US010340457B2

(12) United States Patent
D'Lavari et al.

(10) Patent No.: US 10,340,457 B2
(45) Date of Patent: Jul. 2, 2019

(54) ORGANIC SEMICONDUCTING COMPOUNDS

(71) Applicant: Merck Patent GmbH, Darmstadt (DE)

(72) Inventors: Mansoor D'Lavari, Bude (GB); William Mitchell, Chandler's Ford (GB); Changsheng Wang, Durham (GB); David Sparrowe, Bournemouth (GB)

(73) Assignee: Merck Patent GmbH, Darmstadt (DE)

( * ) Notice: Subject to any disclaimer, the term of this patent is extended or adjusted under 35 U.S.C. 154(b) by 92 days.

(21) Appl. No.: 15/302,602

(22) PCT Filed: Mar. 17, 2015

(86) PCT No.: PCT/EP2015/000586
§ 371 (c)(1),
(2) Date: Oct. 7, 2016

(87) PCT Pub. No.: WO2015/154845
PCT Pub. Date: Oct. 15, 2015

(65) Prior Publication Data
US 2017/0117477 A1    Apr. 27, 2017

(30) Foreign Application Priority Data

Apr. 10, 2014  (EP) .................................... 14001324

(51) Int. Cl.
*H01B 1/00*     (2006.01)
*H01L 51/00*    (2006.01)
(Continued)

(52) U.S. Cl.
CPC ........ *H01L 51/0036* (2013.01); *C07D 495/04* (2013.01); *C07D 495/22* (2013.01);
(Continued)

(58) Field of Classification Search
CPC ........... H01B 1/00; H01B 1/124; H01L 51/00; C07D 487/00; C08G 61/12; C08G 61/123
See application file for complete search history.

(56) References Cited

U.S. PATENT DOCUMENTS 9,017,577 B2    4/2015  Tierney et al.
9,620,716 B2 *  4/2017  Wang ...................... C08K 3/04
(Continued)

FOREIGN PATENT DOCUMENTS

EP          2075274 A1      7/2009
JP       2009-302470 A     12/2009
(Continued)

OTHER PUBLICATIONS

International Search Report dated Jun. 10, 2015 issued in corresponding PCT/EP2015/000586 application (4 pages).
(Continued)

*Primary Examiner* — Mark Kopec
(74) *Attorney, Agent, or Firm* — Millen White Zelano and Branigan, PC; John Sopp

(57) ABSTRACT

The invention relates to novel organic semiconducting compounds, which are small molecules or conjugated polymers, containing one or more fluorinated polycyclic units, to methods for their preparation and educts or intermediates used therein, to compositions, polymer blends and formulations containing them, to the use of the compounds, compositions and polymer blends as organic semiconductors in, or for the preparation of, organic electronic (OE) devices, especially organic photovoltaic (OPV) devices, organic photodetectors (OPD), organic field effect transistors (OFET) and organic light emitting diodes (OLED), and to OE, OPV, OPD, OFET and OLED devices comprising these compounds, compositions or polymer blends.

34 Claims, 1 Drawing Sheet

(51) Int. Cl.
*C08G 61/00* (2006.01)
*C08G 61/12* (2006.01)
*C07D 495/04* (2006.01)
*C07D 495/22* (2006.01)
*H01L 51/05* (2006.01)
*H01L 51/42* (2006.01)
*H01L 51/50* (2006.01)

(52) U.S. Cl.
CPC ........ *C08G 61/126* (2013.01); *H01L 51/0043* (2013.01); *C08G 61/123* (2013.01); *C08G 2261/124* (2013.01); *C08G 2261/148* (2013.01); *C08G 2261/1412* (2013.01); *C08G 2261/18* (2013.01); *C08G 2261/228* (2013.01); *C08G 2261/312* (2013.01); *C08G 2261/3243* (2013.01); *C08G 2261/3246* (2013.01); *C08G 2261/522* (2013.01); *C08G 2261/91* (2013.01); *C08G 2261/92* (2013.01); *C08G 2261/95* (2013.01); *H01L 51/0046* (2013.01); *H01L 51/0047* (2013.01); *H01L 51/0512* (2013.01); *H01L 51/0541* (2013.01); *H01L 51/42* (2013.01); *H01L 51/4253* (2013.01); *H01L 51/50* (2013.01); *H01L 51/5012* (2013.01); *Y02E 10/549* (2013.01); *Y02P 70/521* (2015.11)

(56) References Cited

U.S. PATENT DOCUMENTS

| | | | |
|---|---|---|---|
| 9,761,805 B2 * | 9/2017 | Wang | C07D 495/22 |
| 9,837,613 B2 * | 12/2017 | Mitchell | B82Y 10/00 |
| 2011/0226999 A1 | 9/2011 | Tierney et al. | |
| 2014/0158949 A1 | 6/2014 | Wang et al. | |
| 2015/0014599 A1 | 1/2015 | Griffiths | |
| 2015/0021524 A1 | 1/2015 | Griffiths | |
| 2015/0028261 A1 | 1/2015 | Griffiths | |
| 2015/0028262 A1 | 1/2015 | Griffiths | |
| 2015/0034878 A1 | 2/2015 | Griffiths | |
| 2015/0034879 A1 | 2/2015 | Griffiths | |
| 2016/0013416 A1 | 1/2016 | Griffiths | |

FOREIGN PATENT DOCUMENTS

| | | |
|---|---|---|
| WO | 2010/020329 A1 | 2/2010 |
| WO | 2010/041687 A1 | 4/2010 |
| WO | 2013/010614 A2 | 1/2013 |
| WO | 2013/124687 A1 | 8/2013 |

OTHER PUBLICATIONS

Written Opinion of the International Searching Authority dated Jun. 10, 2015 issued in corresponding PCT/EP2015/000586 application (5 pages).

Y. Li et al., "Eleven-Membered Fused-Ring Low Band-Gap Polymer with Enhanced Charge Carrier Mobility and Photovoltaic Performance", Advanced Functional Materials, vol. 24, No. 23 (Mar. 6, 2014) pp. 3631-3638.

English Abstract of JP 2009-302470 A published Dec. 24, 2009.

* cited by examiner

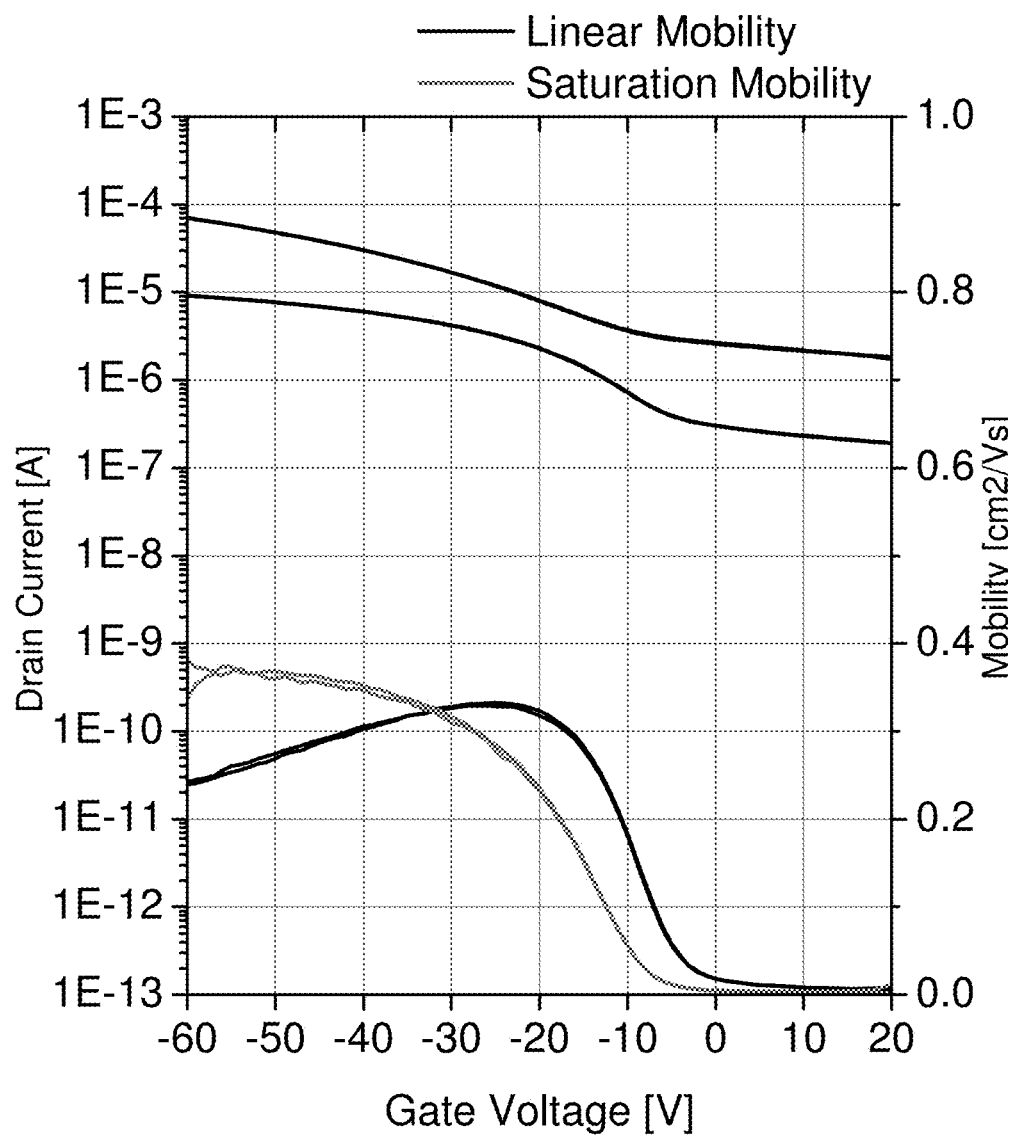

ORGANIC SEMICONDUCTING COMPOUNDS

TECHNICAL FIELD

The invention relates to novel organic semiconducting compounds, which are small molecules or conjugated polymers, containing one or more fluorinated polycyclic units, to methods for their preparation and educts or intermediates used therein, to compositions, polymer blends and formulations containing them, to the use of the compounds, compositions and polymer blends as organic semiconductors in, or for the preparation of, organic electronic (OE) devices, especially organic photovoltaic (OPV) devices, organic photodetectors (OPD), organic field effect transistors (OFET) and organic light emitting diodes (OLED), and to OE, OPV, OPD, OFET and OLED devices comprising these compounds, compositions or polymer blends.

BACKGROUND

In recent years, there has been development of organic semiconducting (OSC) materials in order to produce more versatile, lower cost electronic devices. Such materials find application in a wide range of devices or apparatus, including organic field effect transistors (OFETs), organic light emitting diodes (OLEDs), organic photodetectors (OPDs), organic photovoltaic (OPV) cells, sensors, memory elements and logic circuits to name just a few. The organic semiconducting materials are typically present in the electronic device in the form of a thin layer, for example of between 50 and 300 nm thickness.

One particular area of importance is organic photovoltaics (OPV). Conjugated polymers have found use in OPVs as they allow devices to be manufactured by solution-processing techniques such as spin casting, dip coating or ink jet printing. Solution processing can be carried out cheaper and on a larger scale compared to the evaporative techniques used to make inorganic thin film devices. Currently, polymer based photovoltaic devices are achieving efficiencies above 8%.

In order to obtain ideal solution-processible OSC molecules two basic features are essential, firstly a rigid π-conjugated core unit to form the backbone, and secondly a suitable functionality attached to the aromatic core unit in the OSC backbone. The former extends π-π overlaps, defines the primary energy levels of the highest occupied and lowest unoccupied molecular orbitals (HOMO and LUMO), enables both charge injection and transport, and facilitates optical absorption. The latter further fine-tunes the energy levels and enables solubility and hence processibility of the materials as well as π-π interactions of the molecular backbones in the solid state.

A high degree of molecular planarity reduces the energetic disorder of OSC backbones and accordingly enhances charge carrier mobilities. Linearly fusing aromatic rings is an efficient way of achieving maximum planarity with extended π-π conjugation of OSC molecules. Accordingly, most of the known polymeric OSCs with high charge carrier mobilities are generally composed of fused ring aromatic systems and are semicrystalline in their solid states. On the other hand, such fused aromatic ring systems are often difficult to synthesize, and do also often show poor solubility in organic solvents, which renders their processing as thin films for use in OE devices more difficult.

Another particular area of importance are OFETs. The performance of OFET devices is principally based upon the charge carrier mobility of the semiconducting material and the current on/off ratio, so the ideal semiconductor should have a low conductivity in the off state, combined with high charge carrier mobility ($>1\times10^{-3}$ cm$^2$ V$^{-1}$ s$^{-1}$). In addition, it is important that the semiconducting material is stable to oxidation i.e. it has a high ionisation potential, as oxidation leads to reduced device performance. Further requirements for the semiconducting material are good processibility, especially for large-scale production of thin layers and desired patterns, and high stability, film uniformity and integrity of the organic semiconductor layer.

In prior art, various materials have been proposed for use as organic semiconductors in OFETs, including small molecules like for example pentacene, and polymers like for example polyhexylthiophene. However, the materials and devices investigated so far do still have several drawbacks, and their properties, especially the processibility, charge-carrier mobility, on/off ratio and stability do still leave room for further improvement.

Presently the charge carrier mobility of OSC materials and their application in OFETs are the focus of many research groups. This is mainly driven by the tuneable electronic properties of these organic materials. These compounds are preferred alternatives to amorphous silicon technology due to their prospect of low-cost, solution processability, high throughput with low temperature deposition, the ease of large area device fabrication, light weight and flexibility.

A wide variety of organic compounds have been used to fabricate OFETs. A promising performance with enhanced electron delocalization, conductivity, ability to form planar conjugated structures has been observed for linearly fused polycyclic aromatic compounds. However, these materials so far do still have some drawbacks when used in devices like, for example, inadequate mobility to drive OLED displays, and potential stability issues.

The OSC materials as disclosed in prior art do thus still leave room for further improvement, for example regarding their processibility and their electronic properties. Therefore there is still a need for OSC materials for use in OE devices like OFETs and OPV cells, which have advantageous properties, in particular good processibility, high solubility in organic solvents, good structural organization and film-forming properties. In addition, the OSC materials should be easy to synthesize, especially by methods suitable for mass production. For use in OPV cells, the OSC materials should especially have a low bandgap, which enables improved light harvesting by the photoactive layer and can lead to higher cell efficiencies, high stability and long lifetime. For use in OFETs the OSC materials should especially have high charge-carrier mobility, high on/off ratio in transistor devices, high oxidative stability and long lifetime.

It was an aim of the present invention to provide compounds for use as OSC materials that provide one or more of the above-mentioned advantageous properties, especially easy synthesis by methods suitable for mass production, good processibility, high stability, good solubility in organic solvents, high charge carrier mobility, and a low bandgap. Another aim of the invention was to extend the pool of OSC materials available to the expert. Other aims of the present invention are immediately evident to the expert from the following detailed description.

The inventors of the present invention have found that one or more of the above aims can be achieved by providing small molecules and conjugated polymers as disclosed and claimed hereinafter. These comprise polycyclic units with a difluorinated central benzene ring. It has been found that these fluorinated units, when used as monomeric units in organic pi-conjugated polymers, will deepen the HOMO level of the polymer and as such potentially improve the device stability.

In prior art various linearly fused polycyclic aromatic compounds have been proposed for use as organic semiconductors in OFETs, such as indacenodithiophene (IDT) as disclosed for example in WO 2010/020329 A1 and EP 2075274 A1, indacenothienothiophene (IDTT) as disclosed for example in WO 2013/010614 A2, indenofluorene (IF) as disclosed for example in WO 2013/124687 A1 and WO 2010/041687 A1, and their derivatives. WO 2010/041687 A1 discloses, among others, a compound of the following formula

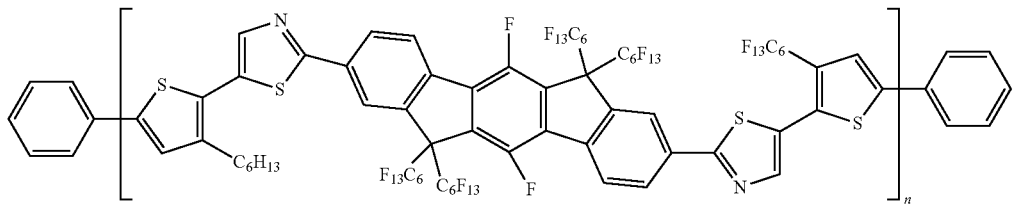

However, fused polycyclic aromatic compounds with a fluorinated central benzene ring as disclosed and claimed hereinafter have hitherto not been disclosed or suggested in prior art.

SUMMARY

The invention relates to a compound comprising one or more divalent units of formula I polycyclic aryl or heteroaryl, each of which is optionally substituted with one or more groups $R^S$ and has 4 to 30 ring atoms, p, q are independently of each other 0, 1 or 2, $Ar^{21}$, $Ar^{22}$, $Ar^{23}$, $Ar^{24}$ denote, independently of each other, and on each occurrence identically or differently, an aromatic or heteroaromatic group, each of which is monocyclic or polycyclic, has 4 to 20 ring atoms, and is optionally substituted by one or more groups $R^S$, $R^S$ denotes, on each occurrence identically or differently, F, Br, Cl, —CN, —NC, —NCO, —NCS, —OCN, —SCN, —C(O)NR°R°°, —C(O)X°, —C(O)R°, —C(O)OR°, —NH$_2$, —NR°R°°, —SH, —SR°, —SO$_3$H, —SO$_2$R°, —OH, —NO$_2$, —CF$_3$, —SF$_5$, optionally substituted silyl, carbyl or hydrocarbyl with 1 to 40 C atoms that is optionally substituted and optionally comprises one or more hetero atoms, $R°$, $R°°$ independently of each other denote H or optionally substituted $C_{1-40}$ carbyl or hydrocarbyl, and preferably denote H or alkyl with 1 to 12 C-atoms, $Y^1$, $Y^2$ independently of each other denote H, F, Cl or CN, $X°$ denotes halogen, preferably F, Cl or Br,

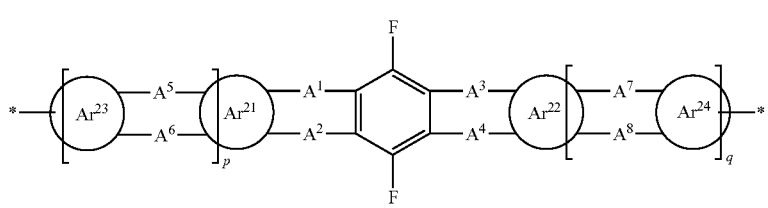

wherein
one of $A^1$ and $A^2$ is X and the other is a single bond,
one of $A^3$ and $A^4$ is X and the other is a single bond,
one of $A^5$ and $A^6$ is X and the other is a single bond,
one of $A^7$ and $A^8$ is X and the other is a single bond,
X is, on each occurrence identically or differently, $CR^1R^2$, $C=CR^1R^2$, $SiR^1R^2$, $GeR^1R^2$, C=O or $NR^1$,
$R^1$, $R^2$ denote, independently of each other and on each occurrence identically or differently, H or straight chain, branched or cyclic alkyl group with 1 to 50 C atoms in which one or more non-adjacent CH$_2$ groups are optionally replaced, in each case independently from one another, by —O—, —S—, —C(O)—, —C(O)O—, —O—C(O)—, —O—CO(O)—O—, —SO$_2$—, —SO$_3$—, —NR°—, —SiR°R°°—, —CF$_2$—, —CR°=CR°°—, —CY$^1$=CY$^2$— or —C≡C— in such a manner that O and/or S atoms are not linked directly to one another, and in which one or more, but not all, H atoms are optionally replaced by F, Cl, Br, I or CN, or denotes monocyclic or with the proviso that, if $Ar^{21}$ and $Ar^{22}$ are benzene rings, p=q=0, and $A^1$, $A^2$, $A^3$ and $A^4$ are $CR^1R^2$, then $R^1$ and $R^2$ are not perfluoroalkyl.

The invention further relates to a formulation comprising one or more compounds comprising a unit of formula I and one or more solvents, preferably selected from organic solvents.

The invention further relates to the use of units of formula I as electron donor or electron acceptor units in semiconducting polymers.

The invention further relates to conjugated polymers comprising one or more repeating units of formula I.

The invention further relates to conjugated polymers comprising one or more repeating units of formula I and/or one or more groups selected from aryl and heteroaryl groups that are optionally substituted, and wherein at least one repeating unit in the polymer is a unit of formula I.

The invention further relates to monomers containing a unit of formula I and further containing one or more reactive groups which can be reacted to form a conjugated polymer as described above and below.

The invention further relates to semiconducting polymers comprising one or more units of formula I and one or more additional units which are different from formula I and have electron donor properties.

The invention further relates to semiconducting polymers comprising one or more units of formula I as electron donor units, and preferably further comprising one or more units having electron acceptor properties.

The invention further relates to the use of the compounds according to the present invention as electron donor or p-type semiconductor.

The invention further relates to the use of the compounds according to the present invention as dyes or pigments.

The invention further relates to the use of the compounds according to the present invention as electron donor component in a semiconducting material, formulation, polymer blend, device or component of a device.

The invention further relates to a semiconducting material, formulation, polymer blend, device or component of a device comprising a compound according to the present invention as electron donor component, and preferably further comprising one or more compounds or polymers having electron acceptor properties.

The invention further relates to a composition or polymer blend comprising one or more compounds according to the present invention, and further comprising one or more compounds selected from compounds having one or more of semiconducting, charge transport, hole or electron transport, hole or electron blocking, electrically conducting, photoconducting or light emitting properties.

The invention further relates to a composition or polymer blend as described above and below, which comprises one or more compounds according to the present invention, and further comprises one or more n-type organic semiconductor compounds, preferably selected from fullerenes or substituted fullerenes.

The invention further relates to the use of a compound according to the present invention, or a composition or polymer blend comprising it as described above and below, as semiconducting, charge transport, electrically conducting, photoconducting, photoactive or light emitting material or as dye or pigment, or in an optical, electrooptical, electronic, electroluminescent or photoluminescent device, or in a component of such a device or in an assembly comprising such a device or component.

The invention further relates to a semiconducting, charge transport, electrically conducting, photoconducting, photoactive or light emitting material or a dye or pigment, comprising a compound, composition or polymer blend according to the present invention.

The invention further relates to a formulation comprising one or more compounds according to the present invention, or a composition or polymer blend comprising it as described above and below, and further comprising one or more solvents, preferably selected from organic solvents.

The invention further relates to an optical, electrooptical, electronic, photoactive, electroluminescent or photoluminescent device, or a component thereof, or an assembly comprising it, which is prepared using a formulation as described above and below.

The invention further relates to an optical, electrooptical, electronic, photoactive, electroluminescent or photoluminescent device, or a component thereof, or an assembly comprising it, which comprises a compound according to the present invention, or a composition or polymer blend comprising it.

The invention further relates to an optical, electrooptical, electronic, photoactive, electroluminescent or photoluminescent device, or a component thereof, which comprises a semiconducting, charge transport, electrically conducting, photoconducting or light emitting material or a dye or pigment according to the present invention as described above and below.

The optical, electrooptical, electronic, electroluminescent and photoluminescent devices include, without limitation, organic field effect transistors (OFET), organic thin film transistors (OTFT), organic light emitting diodes (OLED), organic light emitting transistors (OLET), organic photovoltaic devices (OPV), organic photodetectors (OPD), organic solar cells, dye-sensitized solar cells (DSSC), laser diodes, Schottky diodes, photoconductors, photodetectors and thermoelectric devices.

Preferred devices are OFETs, OTFTs, OPVs, OPDs and OLEDs, in particular bulk heterojunction (BHJ) OPVs or inverted BHJ OPVs.

Further preferred is the use of a compound, composition or polymer blend according to the present invention as dye in a DSSC or a perovskite-based solar cells, and a DSSC or perovskite-based solar cells comprising a compound, composition or polymer blend according to the present invention.

The components of the above devices include, without limitation, charge injection layers, charge transport layers, interlayers, planarising layers, antistatic films, polymer electrolyte membranes (PEM), conducting substrates and conducting patterns.

The assemblies comprising such devices or components include, without limitation, integrated circuits (IC), radio frequency identification (RFID) tags or security markings or security devices containing them, flat panel displays or backlights thereof, electrophotographic devices, electrophotographic recording devices, organic memory devices, sensor devices, biosensors and biochips.

In addition the compounds, polymers, compositions, polymer blends and formulations of the present invention can be used as electrode materials in batteries and in components or devices for detecting and discriminating DNA sequences.

Terms and Definitions

As used herein, the term "polymer" will be understood to mean a molecule of high relative molecular mass, the structure of which essentially comprises the multiple repetition of units derived, actually or conceptually, from molecules of low relative molecular mass (*Pure Appl. Chem.*, 1996, 68, 2291). The term "oligomer" will be understood to mean a molecule of intermediate relative molecular mass, the structure of which essentially comprises a small plurality of units derived, actually or conceptually, from molecules of lower relative molecular mass (*Pure Appl. Chem.*, 1996, 68, 2291). In a preferred meaning as used herein present invention a polymer will be understood to mean a compound having >1, i.e. at least 2 repeat units, preferably ≥5 repeat units, and an oligomer will be understood to mean a compound with >1 and <10, preferably <5, repeat units.

Further, as used herein, the term "polymer" will be understood to mean a molecule that encompasses a backbone (also referred to as "main chain") of one or more distinct types of repeat units (the smallest constitutional unit of the molecule) and is inclusive of the commonly known terms "oligomer", "copolymer", "homopolymer" and the like. Further, it will be understood that the term polymer is inclusive of, in addition to the polymer itself, residues from initiators, catalysts and other elements attendant to the synthesis of such a polymer, where such residues are understood as not being covalently incorporated thereto. Further, such residues and other elements, while normally removed during post polymerization purification processes, are typically mixed or co-mingled with the polymer such that they generally remain with the polymer when it is transferred between vessels or between solvents or dispersion media.

As used herein, in a formula showing a polymer or a repeat unit, an asterisk (*) will be understood to mean a chemical linkage to an adjacent unit or to a terminal group in the polymer backbone. In a ring, like for example a benzene or thiophene ring, an asterisk (*) will be understood to mean a C atom that is fused to an adjacent ring.

As used herein, the terms "repeat unit", "repeating unit" and "monomeric unit" are used interchangeably and will be understood to mean the constitutional repeating unit (CRU), which is the smallest constitutional unit the repetition of which constitutes a regular macromolecule, a regular oligomer molecule, a regular block or a regular chain (*Pure Appl. Chem.*, 1996, 68, 2291). As further used herein, the term "unit" will be understood to mean a structural unit which can be a repeating unit on its own, or can together with other units form a constitutional repeating unit.

As used herein, a "terminal group" will be understood to mean a group that terminates a polymer backbone. The expression "in terminal position in the backbone" will be understood to mean a divalent unit or repeat unit that is linked at one side to such a terminal group and at the other side to another repeat unit. Such terminal groups include endcap groups, or reactive groups that are attached to a monomer forming the polymer backbone which did not participate in the polymerisation reaction, like for example a group having the meaning of $R^5$ or $R^6$ as defined below.

As used herein, the term "endcap group" will be understood to mean a group that is attached to, or replacing, a terminal group of the polymer backbone. The endcap group can be introduced into the polymer by an endcapping process. Endcapping can be carried out for example by reacting the terminal groups of the polymer backbone with a monofunctional compound ("endcapper") like for example an alkyl- or arylhalide, an alkyl- or arylstannane or an alkyl- or arylboronate. The endcapper can be added for example after the polymerisation reaction. Alternatively the endcapper can be added in situ to the reaction mixture before or during the polymerisation reaction. In situ addition of an endcapper can also be used to terminate the polymerisation reaction and thus control the molecular weight of the forming polymer. Typical endcap groups are for example H, phenyl and lower alkyl.

As used herein, the term "small molecule" will be understood to mean a monomeric compound which typically does not contain a reactive group by which it can be reacted to form a polymer, and which is designated to be used in monomeric form. In contrast thereto, the term "monomer" unless stated otherwise will be understood to mean a monomeric compound that carries one or more reactive functional groups by which it can be reacted to form a polymer.

As used herein, the terms "donor" or "donating" and "acceptor" or "accepting" will be understood to mean an electron donor or electron acceptor, respectively. "Electron donor" will be understood to mean a chemical entity that donates electrons to another compound or another group of atoms of a compound. "Electron acceptor" will be understood to mean a chemical entity that accepts electrons transferred to it from another compound or another group of atoms of a compound. See also International Union of Pure and Applied Chemistry, Compendium of Chemical Technology, Gold Book, Version 2.3.2, 19 Aug. 2012, pages 477 and 480.

As used herein, the term "n-type" or "n-type semiconductor" will be understood to mean an extrinsic semiconductor in which the conduction electron density is in excess of the mobile hole density, and the term "p-type" or "p-type semiconductor" will be understood to mean an extrinsic semiconductor in which mobile hole density is in excess of the conduction electron density (see also, J. Thewlis, *Concise Dictionary of Physics*, Pergamon Press, Oxford, 1973).

As used herein, the term "leaving group" will be understood to mean an atom or group (which may be charged or uncharged) that becomes detached from an atom in what is considered to be the residual or main part of the molecule taking part in a specified reaction (see also *Pure Appl. Chem.*, 1994, 66, 1134).

As used herein, the term "conjugated" will be understood to mean a compound (for example a polymer) that contains mainly C atoms with $sp^2$-hybridisation (or optionally also sp-hybridisation), and wherein these C atoms may also be replaced by hetero atoms. In the simplest case this is for example a compound with alternating C—C single and double (or triple) bonds, but is also inclusive of compounds with aromatic units like for example 1,4-phenylene. The term "mainly" in this connection will be understood to mean that a compound with naturally (spontaneously) occurring defects, or with defects included by design, which may lead to interruption of the conjugation, is still regarded as a conjugated compound.

As used herein, unless stated otherwise the molecular weight is given as the number average molecular weight $M_n$ or weight average molecular weight $M_w$, which is determined by gel permeation chromatography (GPC) against polystyrene standards in eluent solvents such as tetrahydrofuran, trichloromethane (TCM, chloroform), chlorobenzene or 1,2,4-trichlorobenzene. Unless stated otherwise, 1,2,4-trichlorobenzene is used as solvent. The degree of polymerization, also referred to as total number of repeat units, n, will be understood to mean the number average degree of polymerization given as $n=M_n/M_U$, wherein $M_n$ is the number average molecular weight and $M_U$ is the molecular weight of the single repeat unit, see J. M. G. Cowie, *Polymers: Chemistry & Physics of Modern Materials*, Blackie, Glasgow, 1991.

As used herein, the term "carbyl group" will be understood to mean any monovalent or multivalent organic moiety which comprises at least one carbon atom either without any non-carbon atoms (like for example —C≡C—), or optionally combined with at least one non-carbon atom such as B, N, O, S, P, Si, Se, As, Te or Ge (for example carbonyl etc.).

As used herein, the term "hydrocarbyl group" will be understood to mean a carbyl group that does additionally contain one or more H atoms and optionally contains one or more hetero atoms like for example B, N, O, S, P, Si, Se, As, Te or Ge.

As used herein, the term "hetero atom" will be understood to mean an atom in an organic compound that is not a H- or C-atom, and preferably will be understood to mean B, N, O, S, P, Si, Se, As, Te or Ge.

A carbyl or hydrocarbyl group comprising a chain of 3 or more C atoms may be straight-chain, branched and/or cyclic, and may include spiro-connected and/or fused rings.

Preferred carbyl and hydrocarbyl groups include alkyl, alkoxy, alkylcarbonyl, alkoxycarbonyl, alkylcarbonyloxy and alkoxycarbonyloxy, each of which is optionally substituted and has 1 to 40, preferably 1 to 30, very preferably 1 to 24 C atoms, furthermore optionally substituted aryl or aryloxy having 6 to 40, preferably 6 to 25 C atoms, furthermore alkylaryloxy, arylcarbonyl, aryloxycarbonyl, arylcarbonyloxy and aryloxycarbonyloxy, each of which is optionally substituted and has 6 to 40, preferably 7 to 40 C atoms, wherein all these groups do optionally contain one or more hetero atoms, preferably selected from B, N, O, S, P, Si, Se, As, Te and Ge.

Further preferred carbyl and hydrocarbyl group include for example: a $C_1$-$C_{40}$ alkyl group, a $C_1$-$C_{40}$ fluoroalkyl group, a $C_1$-$C_{40}$ alkoxy or oxaalkyl group, a $C_2$-$C_{40}$ alkenyl group, a $C_2$-$C_{40}$ alkynyl group, a $C_3$-$C_{40}$ allyl group, a $C_4$-$C_{40}$ alkyldienyl group, a $C_4$-$C_{40}$ polyenyl group, a $C_2$-$C_{40}$ ketone group, a $C_2$-$C_{40}$ ester group, a $C_6$-$C_{18}$ aryl group, a $C_6$-$C_{40}$ alkylaryl group, a $C_6$-$C_{40}$ arylalkyl group, a $C_4$-$C_{40}$ cycloalkyl group, a $C_4$-$C_{40}$ cycloalkenyl group, and the like. Preferred among the foregoing groups are a $C_1$-$C_{20}$ alkyl group, a $C_1$-$C_{20}$ fluoroalkyl group, a $C_2$-$C_{20}$ alkenyl group, a $C_2$-$C_{20}$ alkynyl group, a $C_3$-$C_{20}$ allyl group, a $C_4$-$C_{20}$ alkyldienyl group, a $C_2$-$C_{20}$ ketone group, a $C_2$-$C_{20}$ ester group, a $C_6$-$C_{12}$ aryl group, and a $C_4$-$C_{20}$ polyenyl group, respectively.

Also included are combinations of groups having carbon atoms and groups having hetero atoms, like e.g. an alkynyl group, preferably ethynyl, that is substituted with a silyl group, preferably a trialkylsilyl group.

The carbyl or hydrocarbyl group may be an acyclic group or a cyclic group. Where the carbyl or hydrocarbyl group is an acyclic group, it may be straight-chain or branched. Where the carbyl or hydrocarbyl group is a cyclic group, it may be a non-aromatic carbocyclic or heterocyclic group, or an aryl or heteroaryl group.

A non-aromatic carbocyclic group as referred to above and below is saturated or unsaturated and preferably has 4 to 30 ring C atoms. A non-aromatic heterocyclic group as referred to above and below preferably has 4 to 30 ring C atoms, wherein one or more of the C ring atoms are optionally replaced by a hetero atom, preferably selected from N, O, S, Si and Se, or by a —S(O)— or —S(O)$_2$— group. The non-aromatic carbo- and heterocyclic groups are mono- or polycyclic, may also contain fused rings, preferably contain 1, 2, 3 or 4 fused or unfused rings, and are optionally substituted with one or more groups L, wherein L is selected from halogen, —CN, —NC, —NCO, —NCS, —OCN, —SCN, —C(=O)NR$^0$R$^{00}$, —C(=O)X$^0$, —C(=O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, optionally substituted silyl, or carbyl or hydrocarbyl with 1 to 40 C atoms that is optionally substituted and optionally comprises one or more hetero atoms, and is preferably alkyl, alkoxy, thioalkyl, alkylcarbonyl, alkoxycarbonyl or alkoxycarbonyloxy with 1 to 20 C atoms that is optionally fluorinated, X$^0$ is halogen, preferably F, Cl or Br, and R$^0$, R$^{00}$ have the meanings given above and below, and preferably denote H or alkyl with 1 to 20 C atoms.

Preferred substituents L are selected from halogen, most preferably F, or alkyl, alkoxy, oxaalkyl, thioalkyl, fluoroalkyl and fluoroalkoxy with 1 to 16 C atoms, or alkenyl or alkynyl with 2 to 20 C atoms.

Preferred non-aromatic carbocyclic or heterocyclic groups are tetrahydrofuran, indane, pyran, pyrrolidine, piperidine, cyclopentane, cyclohexane, cycloheptane, cyclopentanone, cyclohexanone, dihydro-furan-2-one, tetrahydro-pyran-2-one and oxepan-2-one.

An aryl group as referred to above and below preferably has 4 to 30 ring C atoms, is mono- or polycyclic and may also contain fused rings, preferably contains 1, 2, 3 or 4 fused or unfused rings, and is optionally substituted with one or more groups L as defined above.

A heteroaryl group as referred to above and below preferably has 4 to 30 ring C atoms, wherein one or more of the C ring atoms are replaced by a hetero atom, preferably selected from N, O, S, Si and Se, is mono- or polycyclic and may also contain fused rings, preferably contains 1, 2, 3 or 4 fused or unfused rings, and is optionally substituted with one or more groups L as defined above.

As used herein, "arylene" will be understood to mean a divalent aryl group, and "heteroarylene" will be understood to mean a divalent heteroaryl group, including all preferred meanings of aryl and heteroaryl as given above and below.

Preferred aryl and heteroaryl groups are phenyl in which, in addition, one or more CH groups may be replaced by N, naphthalene, thiophene, selenophene, thienothiophene, dithienothiophene, fluorene and oxazole, all of which can be unsubstituted, mono- or polysubstituted with L as defined above. Very preferred rings are selected from pyrrole, preferably N-pyrrole, furan, pyridine, preferably 2- or 3-pyridine, pyrimidine, pyridazine, pyrazine, triazole, tetrazole, pyrazole, imidazole, isothiazole, thiazole, thiadiazole, isoxazole, oxazole, oxadiazole, thiophene, preferably 2-thiophene, selenophene, preferably 2-selenophene, thieno[3,2-b]thiophene, thieno[2,3-b]thiophene, furo[3,2-b]furan, furo[2,3-b]furan, seleno[3,2-b]selenophene, seleno[2,3-b]selenophene, thieno[3,2-b]selenophene, thieno[3,2-b]furan, indole, isoindole, benzo[b]furan, benzo[b]thiophene, benzo[1,2-b;4,5-b']dithiophene, benzo[2,1-b;3,4-b']dithiophene, quinole, 2-methylquinole, isoquinole, quinoxaline, quinazoline, benzotriazole, benzimidazole, benzothiazole, benzisothiazole, benzisoxazole, benzoxadiazole, benzoxazole, benzothiadiazole, 4H-cyclopenta[2,1-b;3,4-b']dithiophene, 7H-3,4-dithia-7-sila-cyclopenta[a]pentalene, all of which can be unsubstituted, mono- or polysubstituted with L as defined above. Further examples of aryl and heteroaryl groups are those selected from the groups shown hereinafter.

An alkyl group or an alkoxy group, i.e., where the terminal CH$_2$ group is replaced by —O—, can be straight-chain or branched. It is preferably a straight-chain, has 2, 3, 4, 5, 6, 7, 8, 10, 12, 14, 16, 18, 20 or 24 carbon atoms and accordingly is preferably ethyl, propyl, butyl, pentyl, hexyl, heptyl, octyl, decyl, dodecyl, tetradecyl, hexadecyl, octadecyl or didecyl, ethoxy, propoxy, butoxy, pentoxy, hexoxy, heptoxy, octoxy, decoxy, dodecoxy, tetradecoxy, hexadecoxy, octadecoxy or didecoxy, furthermore methyl, nonyl, undecyl, tridecyl, pentadecyl, nonoxy, undecoxy or tridecoxy, for example.

An alkenyl group, i.e., wherein one or more CH$_2$ groups are replaced by —CH=CH— can be straight-chain or branched. It is preferably straight-chain, has 2 to 10 C atoms and accordingly is preferably vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl.

Especially preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples for particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 C atoms are generally preferred.

An oxaalkyl group, i.e., where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

In an alkyl group wherein one $CH_2$ group is replaced by —O— and one $CH_2$ group is replaced by —C(O)—, these radicals are preferably neighboured. Accordingly these radicals together form a carbonyloxy group —C(O)—O— or an oxycarbonyl group —O—C(O)—. Preferably this group is straight-chain and has 2 to 6 C atoms. It is accordingly preferably acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl, 4-(methoxycarbonyl)-butyl.

An alkyl group wherein two or more $CH_2$ groups are replaced by —O— and/or —C(O)O— can be straight-chain or branched. It is preferably straight-chain and has 3 to 12 C atoms. Accordingly it is preferably bis-carboxy-methyl, 2,2-bis-carboxy-ethyl, 3,3-bis-carboxy-propyl, 4,4-bis-carboxy-butyl, 5,5-bis-carboxy-pentyl, 6,6-bis-carboxy-hexyl, 7,7-bis-carboxy-heptyl, 8,8-bis-carboxy-octyl, 9,9-bis-carboxy-nonyl, 10,10-bis-carboxy-decyl, bis-(methoxycarbonyl)-methyl, 2,2-bis-(methoxycarbonyl)-ethyl, 3,3-bis-(methoxycarbonyl)-propyl, 4,4-bis-(methoxycarbonyl)-butyl, 5,5-bis-(methoxycarbonyl)-pentyl, 6,6-bis-(methoxycarbonyl)-hexyl, 7,7-bis-(methoxycarbonyl)-heptyl, 8,8-bis-(methoxycarbonyl)-octyl, bis-(ethoxycarbonyl)-methyl, 2,2-bis-(ethoxycarbonyl)-ethyl, 3,3-bis-(ethoxycarbonyl)-propyl, 4,4-bis-(ethoxycarbonyl)-butyl, 5,5-bis-(ethoxycarbonyl)-hexyl.

A thioalkyl group, i.e., where one $CH_2$ group is replaced by —S—, is preferably straight-chain thiomethyl (—$SCH_3$), 1-thioethyl (—$SCH_2CH_3$), 1-thiopropyl (=—$SCH_2CH_2CH_3$), 1-(thiobutyl), 1-(thiopentyl), 1-(thiohexyl), 1-(thioheptyl), 1-(thiooctyl), 1-(thiononyl), 1-(thiodecyl), 1-(thioundecyl) or 1-(thiododecyl), wherein preferably the $CH_2$ group adjacent to the $sp^2$ hybridised vinyl carbon atom is replaced.

A fluoroalkyl group is perfluoroalkyl $C_iF_{2i+1}$, wherein i is an integer from 1 to 15, in particular $CF_3$, $C_2F_5$, $C_3F_7$, $C_4F_9$, $C_5F_{11}$, $C_6F_{13}$, $C_7F_{15}$ or $C_8F_{17}$, very preferably $C_6F_{13}$, or partially fluorinated alkyl with 1 to 15 C atoms, in particular 1,1-difluoroalkyl, all of which are straight-chain or branched.

Alkyl, alkoxy, alkenyl, oxaalkyl, thioalkyl, carbonyl and carbonyloxy groups can be achiral or chiral groups. Particularly preferred chiral groups are 2-butyl (=1-methylpropyl), 2-methylbutyl, 2-methylpentyl, 2-ethylhexyl, 2-butylhexyl, 2-ethyloctyl, 2-butyloctly, 2-hexyloctyl, 2-ethyldecyl, 2-butyldecyl, 2-hexyldecyl, 2-octyldecyl, 2-ethyldodecyl, 2-butyldodecyl, 2-hexyldodecyl, 2-octyldodecyl, 2-decyldodecyl, 2-propylpentyl, 3-methylpentyl, 3-ethylpentyl, 3-ethylheptyl, 3-butylheptyl, 3-ethylnonyl, 3-butylnonyl, 3-hexylnonyl, 3-ethylundecyl, 3-butylundecyl, 3-hexylundecyl, 3-octylundecyl, in particular 2-methylbutyl, 2-methylbutoxy, 2-methylpentoxy, 3-methylpentoxy, 2-ethylhexoxy, 2-butyloctoxyo, 2-hexyldecoxy, 2-octyldodecoxy, 1-methylhexoxy, 2-octyloxy, 2-oxa-3-methylbutyl, 3-oxa-4-methyl-pentyl, 4-methylhexyl, 2-hexyl, 2-octyl, 2-nonyl, 2-decyl, 2-dodecyl, 6-methoxy-octoxy, 6-methyloctoxy, 6-methyloctanoyloxy, 5-methylheptyloxy-carbonyl, 2-methylbutyryloxy, 3-methylvaleroyloxy, 4-methylhexanoyloxy, 2-chloro-propionyloxy, 2-chloro-3-methylbutyryloxy, 2-chloro-4-methyl-valeryl-oxy, 2-chloro-3-methylvaleryloxy, 2-methyl-3-oxapentyl, 2-methyl-3-oxa-hexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, 1,1,1-trifluoro-2-octyloxy, 1,1,1-trifluoro-2-octyl, 2-fluoromethyloctyloxy for example. Very preferred are 2-ethylhexyl, 2-butylhexyl, 2-ethyloctyl, 2-butyloctly, 2-hexyloctyl, 2-ethyldecyl, 2-butyldecyl, 2-hexyldecyl, 2-octyldecyl, 2-ethyldodecyl, 2-butyldodecyl, 2-hexyldodecyl, 2-octyldodecyl, 2-decyldodecyl, 3-ethylheptyl, 3-butylheptyl, 3-ethylnonyl, 3-butylnonyl, 3-hexylnonyl, 3-ethylundecyl, 3-butylundecyl, 3-hexylundecyl, 3-octylundecyl, 2-hexyl, 2-octyl, 2-octyloxy, 1,1,1-trifluoro-2-hexyl, 1,1,1-trifluoro-2-octyl and 1,1,1-trifluoro-2-octyloxy.

Preferred achiral branched groups are isopropyl, isobutyl (=methylpropyl), isopentyl (=3-methylbutyl), tert. butyl, isopropoxy, 2-methyl-propoxy and 3-methylbutoxy.

In a preferred embodiment, the alkyl groups are independently of each other selected from primary, secondary or tertiary alkyl or alkoxy with 1 to 30 C atoms, wherein one or more H atoms are optionally replaced by F, or aryl, aryloxy, heteroaryl or heteroaryloxy that is optionally alkylated or alkoxylated and has 4 to 30 ring atoms. Very preferred groups of this type are selected from the group consisting of the following formulae

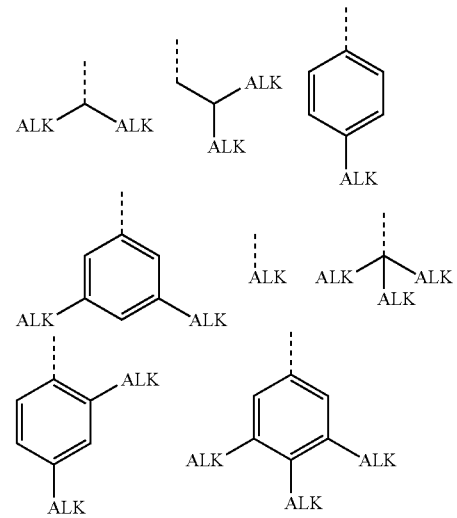

wherein "ALK" denotes optionally fluorinated, preferably linear, alkyl or alkoxy with 1 to 20, preferably 1 to 12 C-atoms, in case of tertiary groups very preferably 1 to 9 C atoms, and the dashed line denotes the link to the ring to which these groups are attached. Especially preferred among these groups are those wherein all ALK subgroups are identical.

As used herein, "halogen" or "hal" means F, Cl, Br or I, preferably F, Cl or Br, very preferably F or Cl.

As used herein, —CO—, C=O, —C(=O)— and —C(O)— will be understood to mean a carbonyl group, i.e. a group having the structure

As used herein, C=CR$^1$R$^2$ will be understood to mean an ylidene group, i.e. a group having the structure

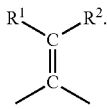

Above and below, Y$^1$ and Y$^2$ are independently of each other H, F, Cl or CN.

Above and below, R$^0$ and R$^{00}$ are independently of each other H or an optionally substituted carbyl or hydrocarbyl group with 1 to 40 C atoms, and preferably denote H or alkyl with 1 to 12 C-atoms.

BRIEF DESCRIPTION OF THE DRAWINGS

The Drawing shows the transfer characteristics and the charge carrier mobility of a top-gate OFET prepared according to Example 1.

DETAILED DESCRIPTION

The compounds of the present invention are easy to synthesize and exhibit advantageous properties. They show good processibility for the device manufacture process, high solubility in organic solvents, and are especially suitable for large scale production using solution processing methods.

The units of formula I are especially suitable as (electron) acceptor or donor unit in both n-type and p-type semiconducting compounds, polymers or copolymers, in particular copolymers containing both donor and acceptor units, and for the preparation of blends of p-type and n-type semiconductors which are suitable for use in BHJ photovoltaic devices.

The units of formula I contain an enlarged system of fused aromatic rings, which creates numerous benefits in developing novel high performance OSC materials. Thus, a large number of fused aromatic rings along the long axis of the core structure increases the overall planarity and reduces the number of the potential twists of the conjugated molecular backbone. Elongation of the π-π structure or monomer increases the extent of conjugation which facilitates charge transport along the polymer backbone. Also, a high proportion of sulphur atoms in the molecular backbone through the presence of fused thiophene rings promotes more intermolecular short contacts, which benefits charge hopping between molecules. Moreover, the large number of fused rings leads to an increased proportion of ladder structure in the OSC polymer main chain. This forms a broader and more intense absorption band resulting in improved solar light harvesting compared with prior art materials. Additionally, fusing aromatic rings can more efficiently modify the HOMO and LUMO energy levels and bandgaps of the target monomer structures compared with periphery substitutions.

In particular, fluorinated organic compounds like those of formula I exhibit a series of unique features, which are related to the properties of the fluorine atom. Among these are the following:

As the most electronegative element, with a Pauling electronegativity of 4.0, fluorine can lower the HOMO level of the polymer and hence increase their thermal and oxidative stability and an elevated resistance to degradation.

Being the smallest electron-withdrawing group (with vander Waals radius, r=1.35 Å) fluorine can be employed without any negative steric effect.

Fluorine atoms often have a great influence on inter- and intramolecular interactions through C—F . . . H, F . . . S, and C—F . . . pi-F interactions. Fluorination can also affect the interchain interactions of polymer backbones, thus leading to different polymer packing in thin films that can in turn tune the field effect mobility.

Di-fluorination of the indeno unit (central ring) is employed as an effective tool capable of modulating the electronic properties of organic pi-conjugated polymers to effectively improve the performance and/or stability of the organic semiconductor.

Besides, the compounds of the present invention show the following advantageous properties:

i) The fluorinated polycyclic unit of formula I exhibits a co-planar structure similar to indenofluorene. Adopting a highly co-planar structure in the solid-state is beneficial for charge transport.

ii) Organic pi-conjugated polymers comprising units of formula I possess a deeper HOMO level compared to polymers comprising corresponding units with an unfluorinated benzene ring, and hence exhibit increased thermal and oxidative stability as well as elevated resistance to degradation.

iii) Fluorine atoms as used in the units of formula I have a great influence on inter- and intra-molecular interactions. These inter-chain interactions of polymer backbones can lead to enhanced polymer packing in thin films resulting in potential improved field effect mobility.

iv) The optoelectronic properties of conjugated polymers vary significantly based upon the intrinsic electron density within each repeating unit and the degree of conjugation between the repeating units along the polymer backbone. By fusing additional aromatic rings along the long axis of the fluorinated unit, the conjugation within the resultant monomers and consequently along the polymers can be extended, and the impact of potential "twists" between repeating units can be minimized.

v) Additional fine-tuning and further modification of the fluorinated ring based polycyclic or co-polymerisation with appropriate co-monomer(s) can afford candidate materials for organic electronic applications.

vi) Variation of the R$^1$, R$^2$ and R$^S$ substituents, and/or introduction of additional substituents on the core unit, allows additional fine-tuning of the polymer electronics.

vii) Additionally, variation of the R$^1$, R$^2$ and R$^S$ substituents and/or introduction of additional substituents on the core unit allows modulation of the polymer solubility.

The synthesis of the unit of formula I, its functional derivatives, compounds, homopolymers, and co-polymers can be achieved based on methods that are known to the skilled person and described in the literature, as will be further illustrated herein.

Preferably, if in formula I Ar$^{21}$ and Ar$^{22}$ are benzene rings, p=q=0, and A$^1$, A$^2$, A$^3$ and A$^4$ are CR$^1$R$^2$, then R$^1$ and R$^2$ are not perfluoroalkyl. More preferably, the following compounds are excluded, wherein n is an integer≥1:

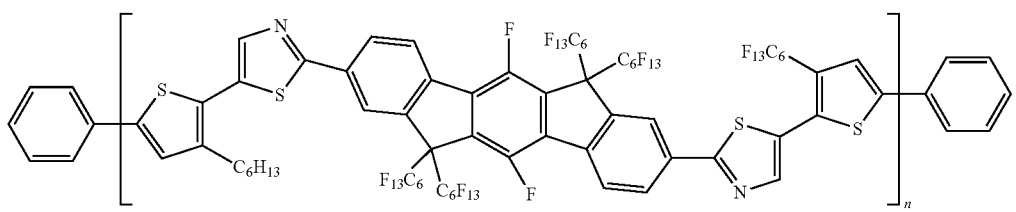

Preferably $R^1$, $R^2$ and $R^S$ in formula I are selected from halogen or straight-chain or branched alkyl, alkoxy, sulfanylalkyl, sulfonylalkyl, alkylcarbonyl, alkoxycarbonyl and alkylcarbonyloxy, each having 1 to 30 C atoms and being unsubstituted or substituted by one or more F atoms, without being perfluorinated, or aryl or heteroaryl, each of which is optionally substituted with one or more groups $R^S$ as defined in formula I and has 4 to 30 ring atoms.

In another preferred embodiment one or more of $R^1$, $R^2$ and $R^S$ denote a straight-chain, branched or cyclic alkyl group with 1 to 50, preferably 2 to 50, very preferably 2 to 30, more preferably 2 to 24, most preferably 2 to 16 C atoms, in which one or more $CH_2$ or $CH_3$ groups are replaced by a cationic or anionic group.

The cationic group is preferably selected from the group consisting of phosphonium, sulfonium, ammonium, uronium, thiouronium, guanidinium or heterocyclic cations such as imidazolium, pyridinium, pyrrolidinium, triazolium, morpholinium or piperidinium cation.

Preferred cationic groups are selected from the group consisting of tetraalkylammonium, tetraalkylphosphonium, N-alkylpyridinium, N,N-dialkylpyrrolidinium, 1,3-dialkylimidazolium, wherein "alkyl" preferably denotes a straight-chain or branched alkyl group with 1 to 12 C atoms.

Further preferred cationic groups are selected from the group consisting of the following formulae

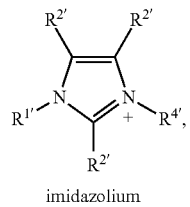

imidazolium

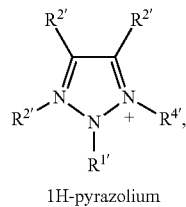

1H-pyrazolium

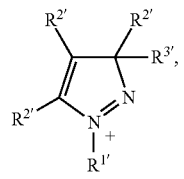

3H-pyrazolium  4H-pyrazolium

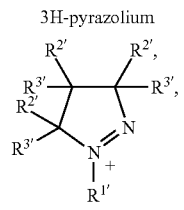

1-pyrazolinium

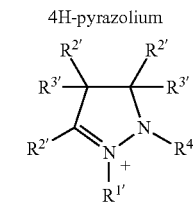

2-pyrazolinium

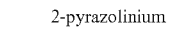

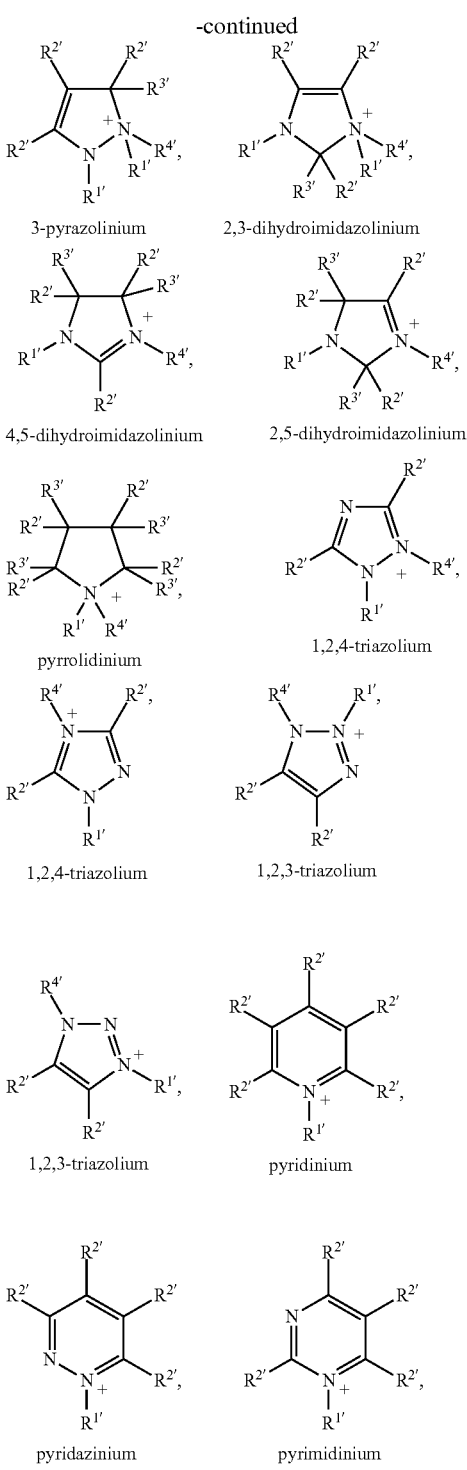

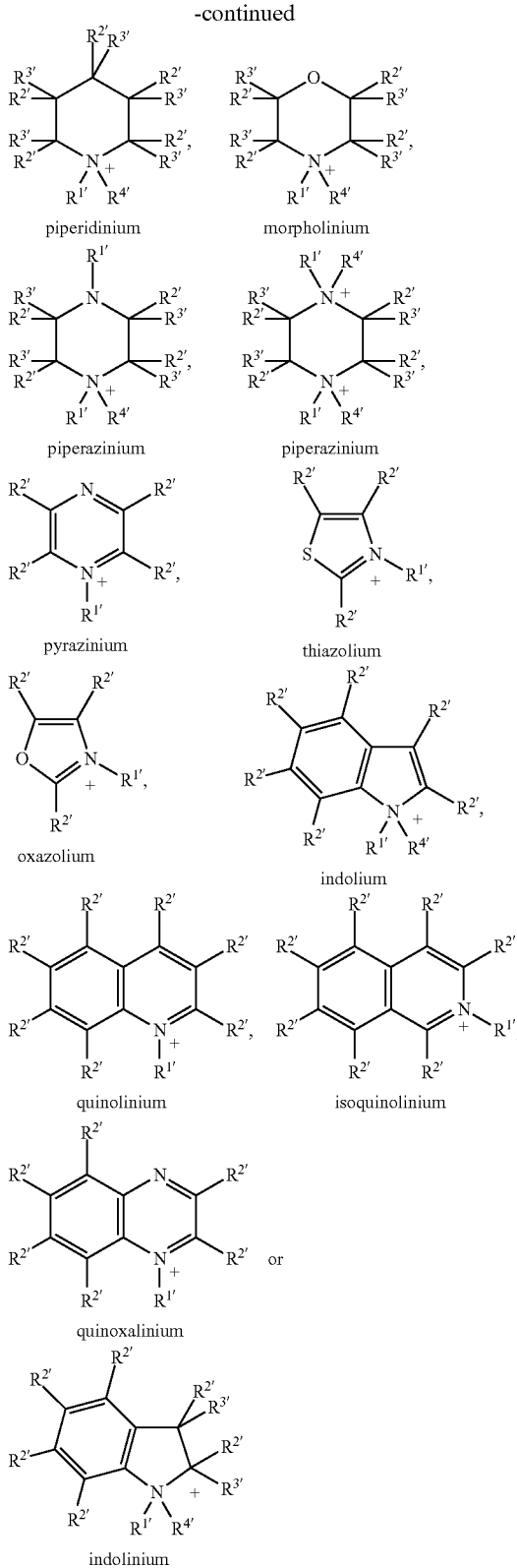

piperidinium morpholinium piperazinium piperazinium pyrazinium thiazolium oxazolium indolium quinolinium isoquinolinium quinoxalinium indolinium wherein $R^{1'}$, $R^{2'}$, $R^{3'}$ and $R^{4'}$ denote, independently of each other, H, a straight-chain or branched alkyl group with 1 to 12 C atoms or non-aromatic carbo- or heterocyclic group or an aryl or heteroaryl group, each of the aforementioned groups having 3 to 20, preferably 5 to 15, ring atoms, being mono- or polycyclic, and optionally being substituted by one or more identical or different substituents $R^S$ as defined above, or denote a link to the group $R^1$.

In the above cationic groups of the above-mentioned formulae any one of the groups $R^{1'}$, $R^{2'}$, $R^{3'}$ and $R^{4'}$ (if they replace a $CH_3$ group) can denote a link to the group $R^1$, or two neighbored groups $R^{1'}$, $R^{2'}$, $R^{3'}$ or $R^{4'}$ (if they replace a $CH_2$ group) can denote a link to the group $R^1$.

The anionic group is preferably selected from the group consisting of borate, imide, phosphate, sulfonate, sulfate, succinate, naphthenate or carboxylate, very preferably from phosphate, sulfonate or carboxylate If $R^1$ in formula I denotes substituted aryl or heteroaryl, it is preferably substituted by one or more groups L, wherein L is selected from P-Sp-, F, Cl, Br, I, —OH, —CN, —NO$_2$, —NCO, —NCS, —OCN, —SCN, —C(=O)NR$^0$R$^{00}$, —C(=O)X$^0$, —C(=O)R$^0$, —NR$^0$R$^{00}$, C(=O)OH, optionally substituted aryl or heteroaryl having 4 to 20 ring atoms, or straight chain, branched or cyclic alkyl with 1 to 20, preferably 1 to 12 C atoms wherein one or more non-adjacent $CH_2$ groups are optionally replaced, in each case independently from one another, by —O—, —S—, —NR$^0$—, —SiR$^0$R$^{00}$—, —C(=O)—, —C(=O)O—, —CY$^1$=CY$^2$— or —C≡C— in such a manner that O and/or S atoms are not linked directly to one another and which is unsubstituted or substituted with one or more F or Cl atoms or OH groups, $X^0$ is halogen, preferably F, Cl or Br, and $Y^1$, $Y^2$, $R^0$ and $R^{00}$ have the meanings given above and below.

In a preferred embodiment $Ar^{21}$, $Ar^{22}$, $Ar^{23}$ and $Ar^{24}$ are selected from the following groups
a) the group consisting of monocyclic aromatic or heteroaromatic groups with 5 or 6 ring atoms, which are optionally substituted with one or more groups $R^S$ as defined in formula I,
b) the group consisting of bi- or tricyclic aromatic or heteroaromatic groups with 10 to 25 ring atoms, which are optionally substituted with one or more groups $R^S$ as defined in formula I.

Preferred monocyclic groups of group a) include, without limitation, pyrrole, thiophene, thiazole, benzene and pyridine, all of which are optionally substituted with one or more groups $R^S$.

Preferred monocyclic groups of group a) include, without limitation, thienothiophene, dithienothiophene, benzodithiophene, fluorene, carbazole, cyclopentadithiophene, silacyclopentadithiophene, indene, naphthalene, anthracene, all of which are optionally substituted with one or more groups $R^S$.

Very preferably $Ar^{21}$, $Ar^{22}$, $Ar^{23}$ and $Ar^{24}$ in formula I, when representing a non-terminal ring, are selected from the following formulae

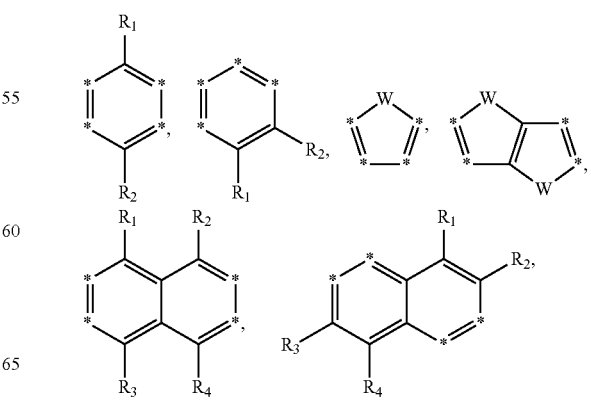

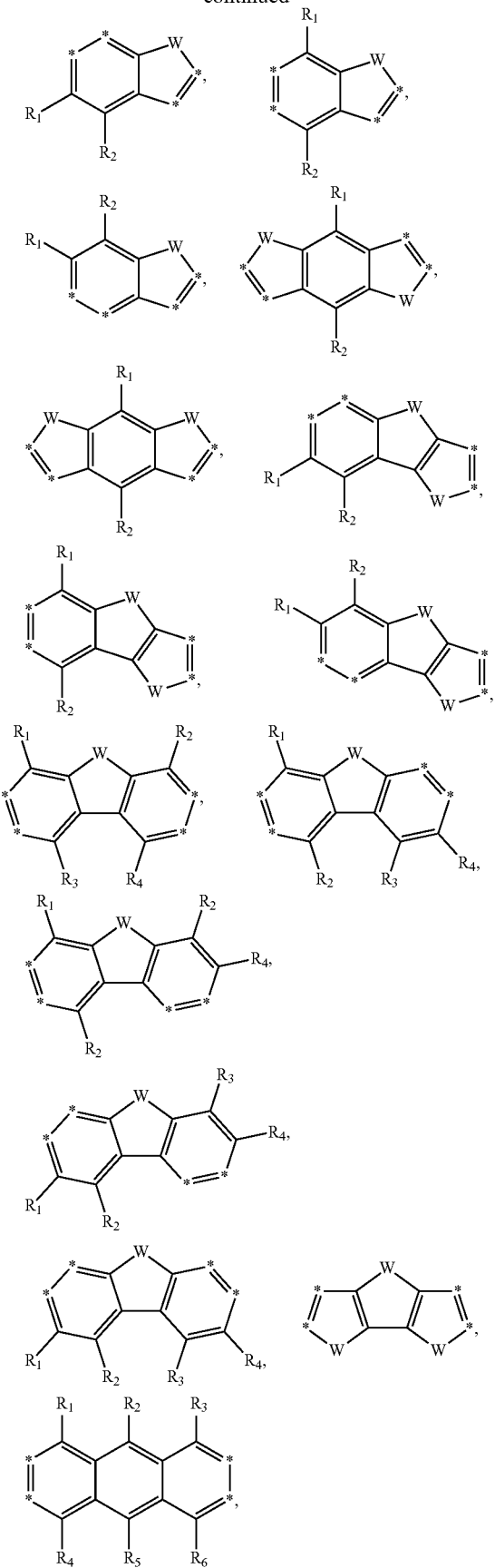
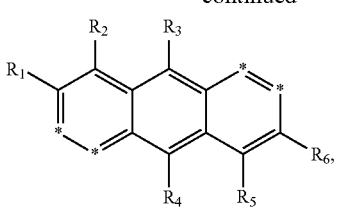

wherein

W is on each occurrence identically or differently S, O or Se, $R^1$ and $R^2$ have independently of each other one of the meanings given above, and $R^3$, $R^4$, $R^5$ and $R^6$ have independently of each other one of the meanings given for $R^1$.

Very preferably $Ar^{21}$, $Ar^{22}$, $Ar^{23}$ and $Ar^{24}$ in formula I, when representing a terminal ring, are selected from the following formulae

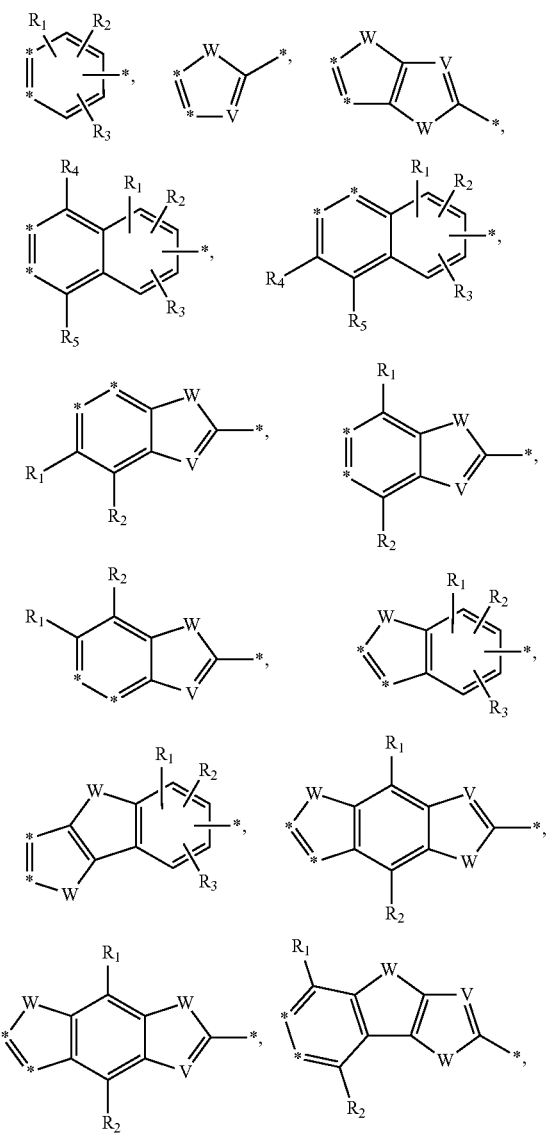

-continued

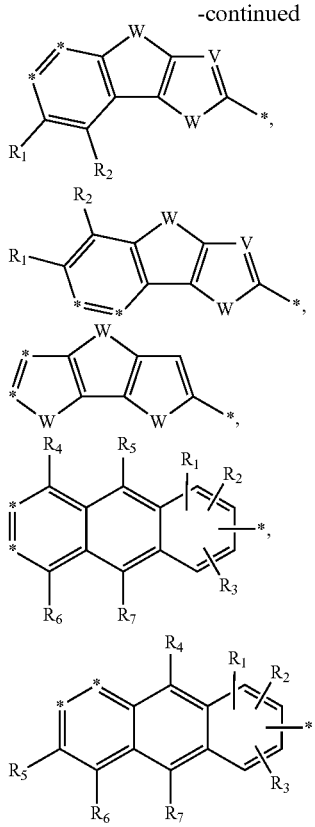

wherein
W is on each occurrence identically or differently S, O or Se,
V is on each occurrence identically or differently $CR^1$ or N,
$R^1$ and $R^2$ have independently of each other one of the meanings given above, and
$R^3$, $R^4$, $R^5$, $R^6$ and $R^7$ have independently of each other one of the meanings given for $R^1$.

Preferred units of formula I are selected from the following preferred embodiments or any combination thereof:

$A^1$, $A^4$, $A^6$ an $A^7$ are a single bond,
$A^1$, $A^3$, $A^6$ and $A^8$ are a single bond,
$A^1$, $A^3$, $A^5$ and $A^7$ are a single bond,
$A^1$, $A^4$, $A^5$ and $A^8$ are a single bond,
X is $CR^1R^2$,
X is $SiR^1R^2$,
X is $NR^1$,
p is 0 and/or q is 0,
p is 0 and q is 0,
p is 0 and q is 1,
p is 0 and q is 2,
p is 1 and q is 1,
p is 1 and q is 2,
p is 2 and q is 2,
$Ar^{21}$, $Ar^{22}$, $Ar^{23}$ and $Ar^{24}$ denote a five-membered ring, or a bicyclic group consisting of two fused five-membered rings, said five-membered rings preferably selected from thiophene,
$Ar^{21}$, $Ar^{22}$, $Ar^{23}$ and $Ar^{24}$ denote a six-membered ring, preferably selected from benzene.

Preferred units of formula I are selected from the following subformulae

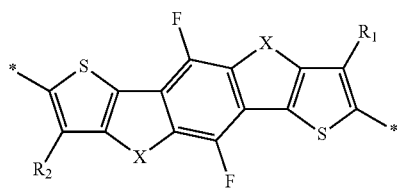

I1

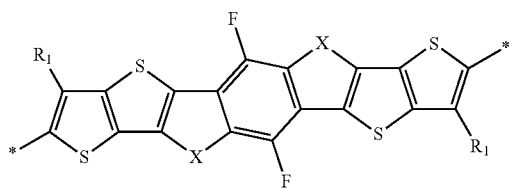

I2

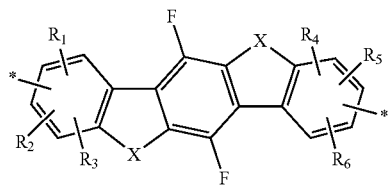

I3

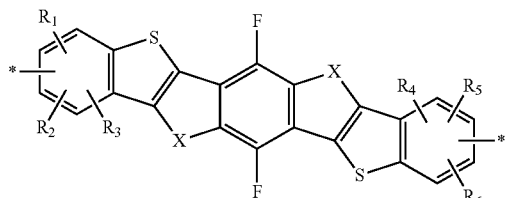

I4

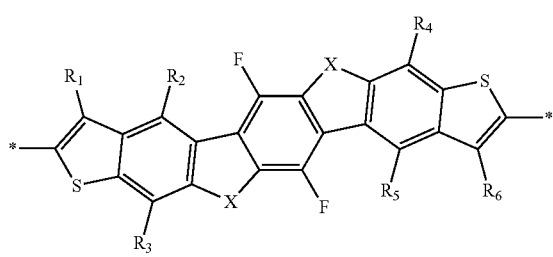

I5

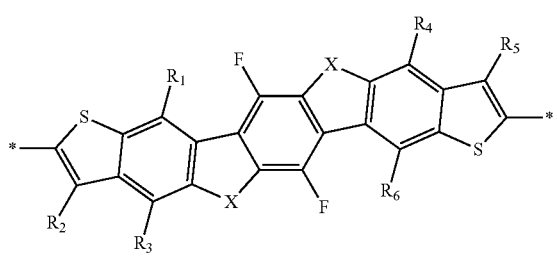

I6

-continued
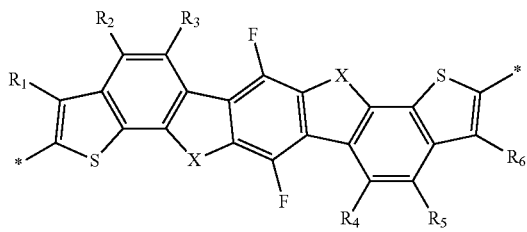
I7
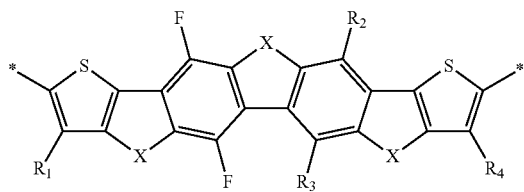
I8
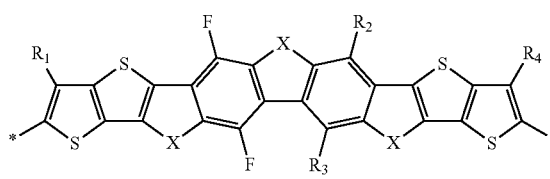
I9
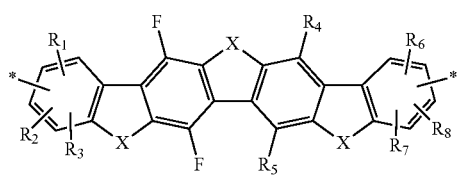
I10
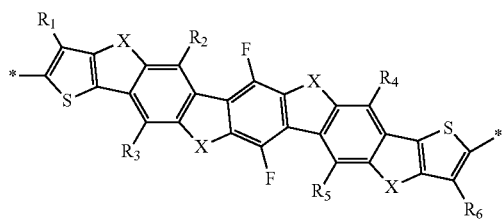
I11
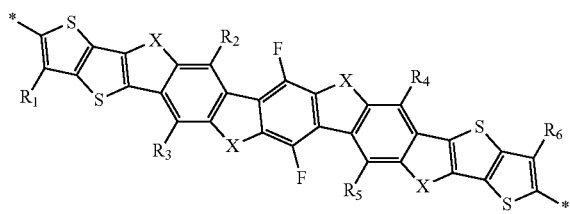
I12
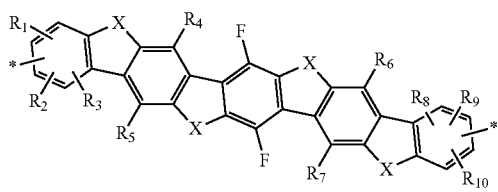
I13
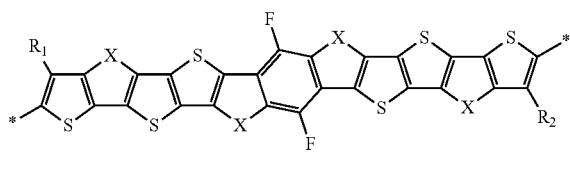
I14
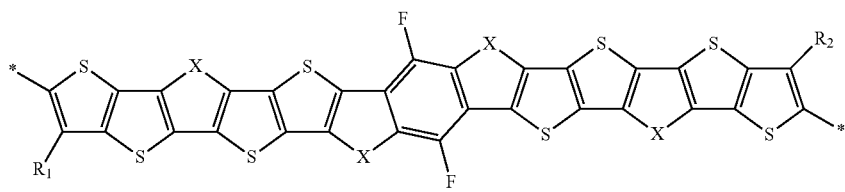
I15
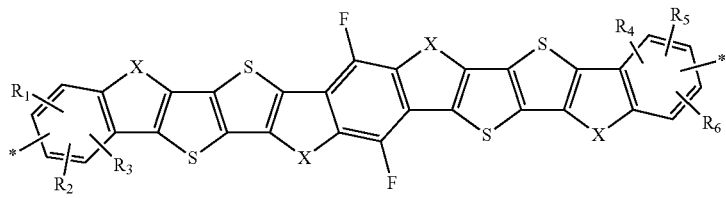
I16
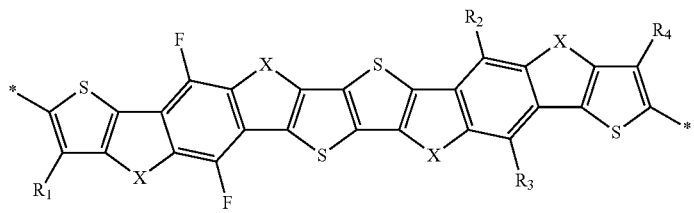
I17

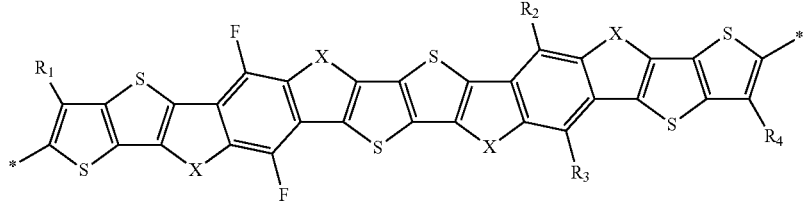

I18

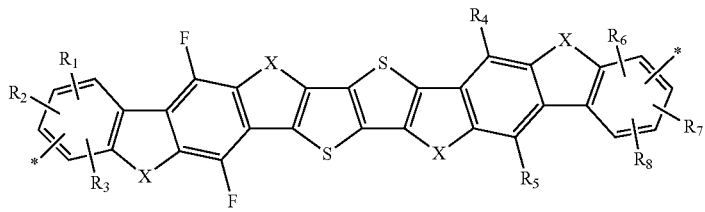

I19

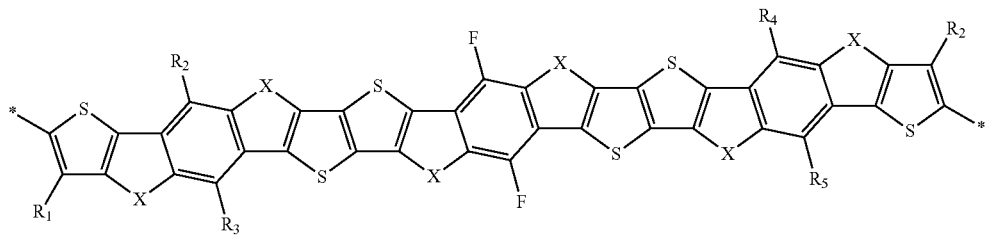

I20

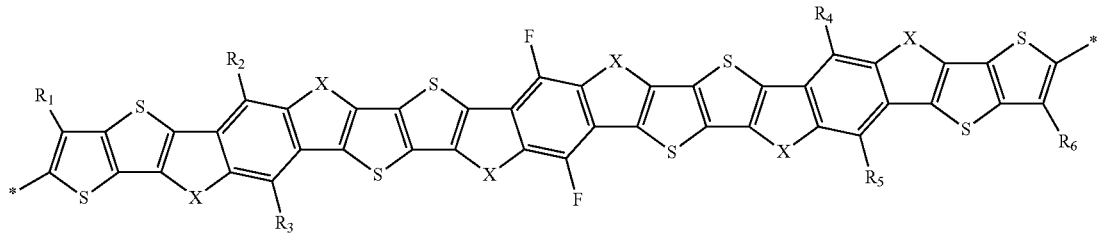

I21

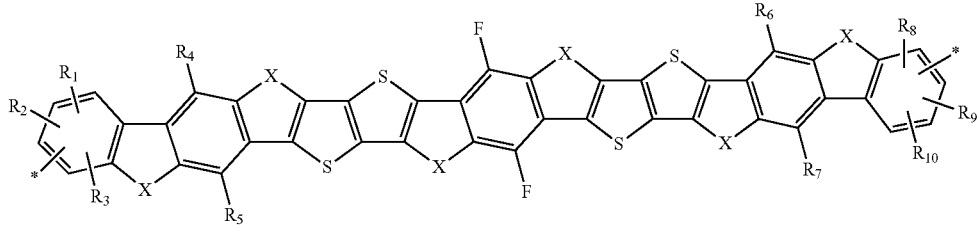

I22 wherein X is $CR^1R^2$, $C=R^1R^2$, $SiR^1R^2$ or $GeR^1R^2$, and $R^1$, $R^2$, $R^3$, $R^4$, $R^5$, $R^6$ and $R^7$ have the meanings given above, and $R^8$ has one of the meanings given for R.

Very preferred units of formula I are selected from the subformulae I1, I2, I3, I8, I9, I10, I11, I12, I13, I14, I15, I16, I17, I18, I19, I20, I21, and I22, wherein X is $CR^1R^2$ or $SiR^1R^2$, preferably $CR^1R^2$, and $R^1$, $R^2$, $R^3$, $R^4$, $R^5$, $R^6$, $R^7$ and $R^8$ have the meanings given above.

Most preferred units of formula I are selected from the subformulae I1, I2 and I3, wherein X is $CR^1R^2$, and $R^1$, $R^2$, $R^3$, $R^4$, $R^5$ and $R^6$ have the meanings given above.

The compounds according to the present invention include small molecules, monomers, oligomers and polymers.

The polymers of the present invention are preferably conjugated polymers.

Polymers according to the present invention preferably comprise two or more units of formula I as defined above and below.

Preferred polymers according to the present invention comprise one or more repeating units of formula IIa or IIb:

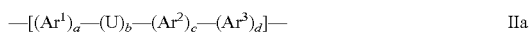      IIa

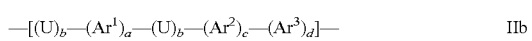      IIb wherein
U is a unit of formula I or its subformulae I1-I22,
$Ar^1$, $Ar^2$, $Ar^3$ are, on each occurrence identically or differently, and independently of each other, aryl or heteroaryl that is different from U, preferably has 5 to 30 ring atoms, and is optionally substituted, preferably by one or more groups $R^S$,
$R^S$ is on each occurrence identically or differently F, Br, Cl, —CN, —NC, —NCO, —NCS, —OCN, —SCN, —C(O)

NR⁰R⁰⁰, —C(O)X⁰, —C(O)R⁰, —C(O)OR⁰, —NH₂, —NR⁰R⁰⁰, —SH, —SR⁰, —SO₃H, —SO₂R⁰, —OH, —NO₂, —CF₃, —SF₅, optionally substituted silyl, carbyl or hydrocarbyl with 1 to 40 C atoms that is optionally substituted and optionally comprises one or more hetero atoms, R⁰ and R⁰⁰ are independently of each other H or optionally substituted C$_{1-40}$ carbyl or hydrocarbyl, and preferably denote H or alkyl with 1 to 12 C-atoms, X⁰ is halogen, preferably F, Cl or Br, a, b, c are on each occurrence identically or differently 0, 1 or 2, d is on each occurrence identically or differently 0 or an integer from 1 to 10, wherein the polymer comprises at least one repeating unit of formula IIa or IIb wherein b is at least 1.

Further preferred polymers according to the present invention comprise, in addition to the units of formula I, IIa or IIb, one or more repeating units selected from monocyclic or polycyclic aryl or heteroaryl groups that are optionally substituted. These additional repeating units are preferably selected of formula IIIa and IIIb —[(Ar¹)$_a$-(A$^c$)$_b$-(Ar²)$_c$—(Ar³)$_d$]—    IIIa -[(A$^c$)$_b$-(Ar¹)$_a$-(A$^c$)$_b$-(Ar²)$_c$—(Ar³)$_d$]—    IIIb wherein Ar¹, Ar², Ar³, a, b, c and d are as defined in formula IIa, and A$^c$ is an aryl or heteroaryl group that is different from U and Ar$^{1-3}$, preferably has 5 to 30 ring atoms, is optionally substituted by one or more groups R$^S$ as defined above and below, and is preferably selected from aryl or heteroaryl groups having electron acceptor properties, wherein the polymer comprises at least one repeating unit of formula IIIa or IIIb wherein b is at least 1.

R$^S$ preferably denotes, on each occurrence identically or differently, H, straight-chain, branched or cyclic alkyl with 1 to 30 C atoms, in which one or more CH₂ groups are optionally replaced by —O—, —S—, —C(O)—, —C(S)—, —C(O)—O—, —O—C(O)—, —NR⁰—, —SiR⁰R⁰⁰—, —CF₂—, —CHR⁰=CR⁰⁰—, —CY¹=CY²— or —C≡C— in such a manner that O and/or S atoms are not linked directly to one another, and in which one or more H atoms are optionally replaced by F, Cl, Br, I or CN, or denotes aryl, heteroaryl, aryloxy or heteroaryloxy with 4 to 20 ring atoms which is optionally substituted, preferably by halogen or by one or more of the aforementioned alkyl or cyclic alkyl groups, wherein R⁰ and R⁰⁰ denote independently of each other H or optionally substituted C$_{1-40}$ carbyl or hydrocarbyl, and preferably denote H or alkyl with 1 to 12 C-atoms, X⁰ denotes halogen, preferably F, Cl or Br, and Y¹ and Y² denote H, F or CN.

The conjugated polymers according to the present invention are preferably selected of formula IV:

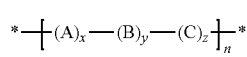    IV wherein

A, B, C independently of each other denote a distinct unit of formula I, Ia, IIa, IIb, IIIa, IIIb, or their subformulae, x is >0 and ≤1, y is ≥0 and <1, z is ≥0 and <1, x+y+z is 1, and n is an integer>1.

Preferred polymers of formula IV are selected of the following formulae

*—[(Ar¹—U—Ar²)$_x$—(Ar³)$_y$]$_n$—*    IVa

*—[(Ar¹—U—Ar²)$_x$—(Ar³—Ar³)$_y$]$_n$—*    IVb

*—[(Ar¹—U—Ar²)$_x$—(Ar³—Ar³—Ar³)$_y$]$_n$—*    IVc

*—[(Ar¹)$_a$—(U)$_b$—(Ar²)$_c$—(Ar³)$_d$]$_n$—*    IVd

*—([(Ar¹)$_a$—(U)$_b$—(Ar²)$_c$—(Ar³)$_d$]$_x$—[(Ar¹)$_a$-(A$^c$)$_b$-(Ar²)$_c$—(Ar³)$_d$]$_y$)$_n$—*    IVe

*—[(U—Ar¹—U)$_x$—(Ar²—Ar³)$_y$]$_n$—*    IVf

*—[(U—Ar¹—U)$_x$—(Ar²—Ar³—Ar²)$_y$]$_n$—*    IVg

*—[(U)$_b$—(Ar¹)$_a$—(U)$_b$—(Ar²)$_c$]$_n$—*    IVh

*—([(U)$_b$—(Ar¹)$_a$—(U)$_b$—(Ar²)$_c$]$_x$—[(A$^c$)$_b$-(Ar¹)$_a$-(A$^c$)$_b$-(Ar²)$_d$]$_y$)$_n$—*    IVi

*—[(U—Ar¹)$_x$—(U—Ar²)$_y$—(U—Ar³)$_z$]$_n$—*    IVk

*—[U]$_n$—*    IVm wherein U, Ar¹, Ar², Ar³, a, b, c and d have in each occurrence identically or differently one of the meanings given in formula IIa, A$^c$ has on each occurrence identically or differently one of the meanings given in formula IIIa, and x, y, z and n are as defined in formula IV, wherein these polymers can be alternating or random copolymers, and wherein in formula IVd and IVe in at least one of the repeating units [(Ar¹)$_a$—(U)$_b$—(Ar²)$_c$—(Ar³)$_d$] and in at least one of the repeating units [(Ar¹)$_a$-(A$^c$)$_b$-(Ar²)$_c$—(Ar³)$_d$] b is at least 1 and wherein in formula IVh and IVi in at least one of the repeating units [(U)$_b$—(Ar¹)$_a$—(U)$_b$—(Ar²)$_d$] and in at least one of the repeating units [(U)$_b$—(Ar¹)$_a$—(U)$_b$—(Ar²)$_d$] b is at least 1, In the polymers of formula IV and its subformulae IVa to IVm, b is preferably 1 in all repeating units.

In the polymers of formula IV and its subformulae IVa to IVm, x is preferably from 0.1 to 0.9, very preferably from 0.3 to 0.7.

In a preferred embodiment of the present invention one of y and z is 0 and the other is >0. In another preferred embodiment of the present invention, both y and z are 0. In yet another preferred embodiment of the present invention, both y and z are >0. If in the polymers of formula IV and its subformulae IVa to IVm y or z is >0, it is preferably from 0.1 to 0.9, very preferably from 0.3 to 0.7.

In the polymers according to the present invention, the total number of repeating units n is preferably from 2 to 10,000. The total number of repeating units n is preferably ≥5, very preferably ≥10, most preferably ≥50, and preferably ≤500, very preferably ≤1,000, most preferably ≤2,000, including any combination of the aforementioned lower and upper limits of n.

The polymers of the present invention include homopolymers and copolymers, like statistical or random copolymers, alternating copolymers and block copolymers, as well as combinations thereof.

Especially preferred are polymers selected from the following groups:

Group A consisting of homopolymers of the unit U or (Ar¹—U) or (Ar¹—U—Ar²) or (Ar¹—U—Ar³) or (U—Ar²—Ar³) or (Ar¹—U—Ar²—Ar³) or (U—Ar¹—U), i.e. where all repeating units are identical, Group B consisting of random or alternating copolymers formed by identical units (Ar¹—U—Ar²) or (U—Ar¹—U) and identical units (Ar³), Group C consisting of random or alternating copolymers formed by identical units (Ar¹—U—Ar²) or (U—Ar¹—U) and identical units (A¹), Group D consisting of random or alternating copolymers formed by identical units (Ar¹—U—Ar²) or (U—Ar¹—U) and identical units (Ar¹-A$^c$-Ar²) or (A$^c$-Ar¹-A$^c$), wherein in all these groups U, A$^c$, Ar¹, Ar² and Ar³ are as defined above and below, in groups A, B and C Ar¹, Ar² and Ar³ are different from a single bond, and in group D one of Ar¹ and Ar² may also denote a single bond.

Especially preferred are repeating units, monomers and polymers of formulae I, IIa, IIb, IIIa, IIIb, IV, IVa-IVm, V, VIa, VIB and their subformulae wherein one or more of Ar¹, Ar² and Ar³ denote aryl or heteroaryl, preferably having electron donor properties, selected from the group consisting of the following formulae

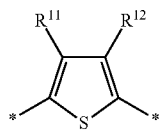
(D1)

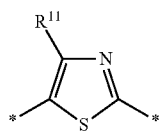
(D2)

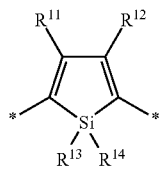
(D3)

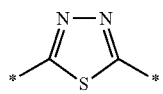
(D4)

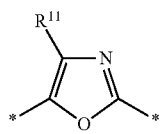
(D5)

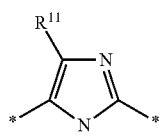
(D6)

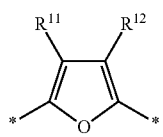
(D7)

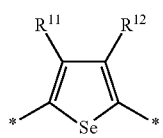
(D8)

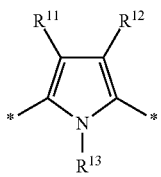
(D9)

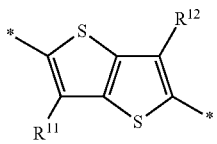
(D10)

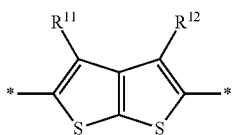
(D11)

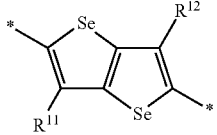
(D12)

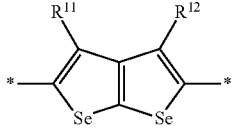
(D13)

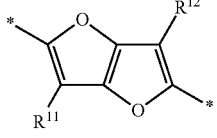
(D14)

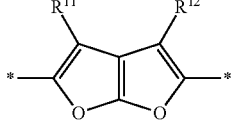
(D15)

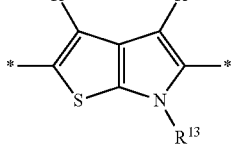
(D16)

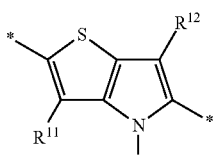
(D17)

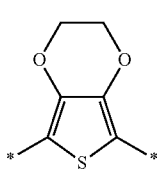
(D18)

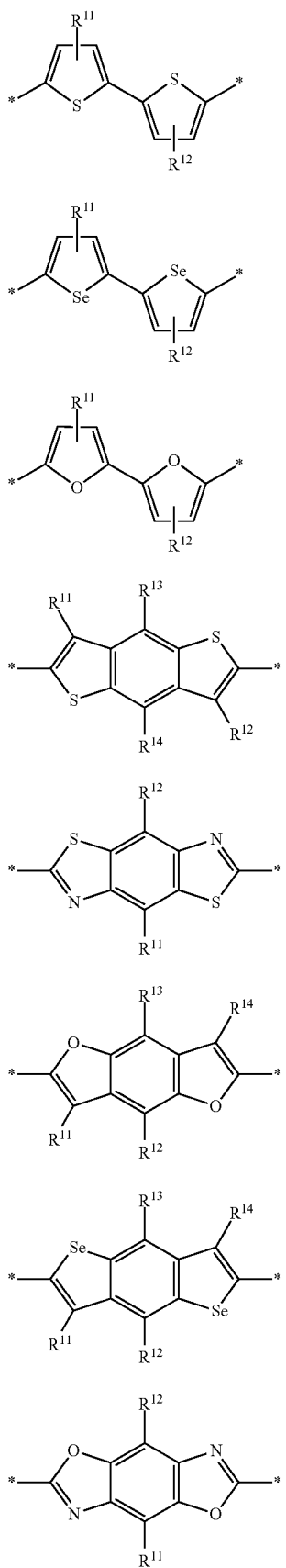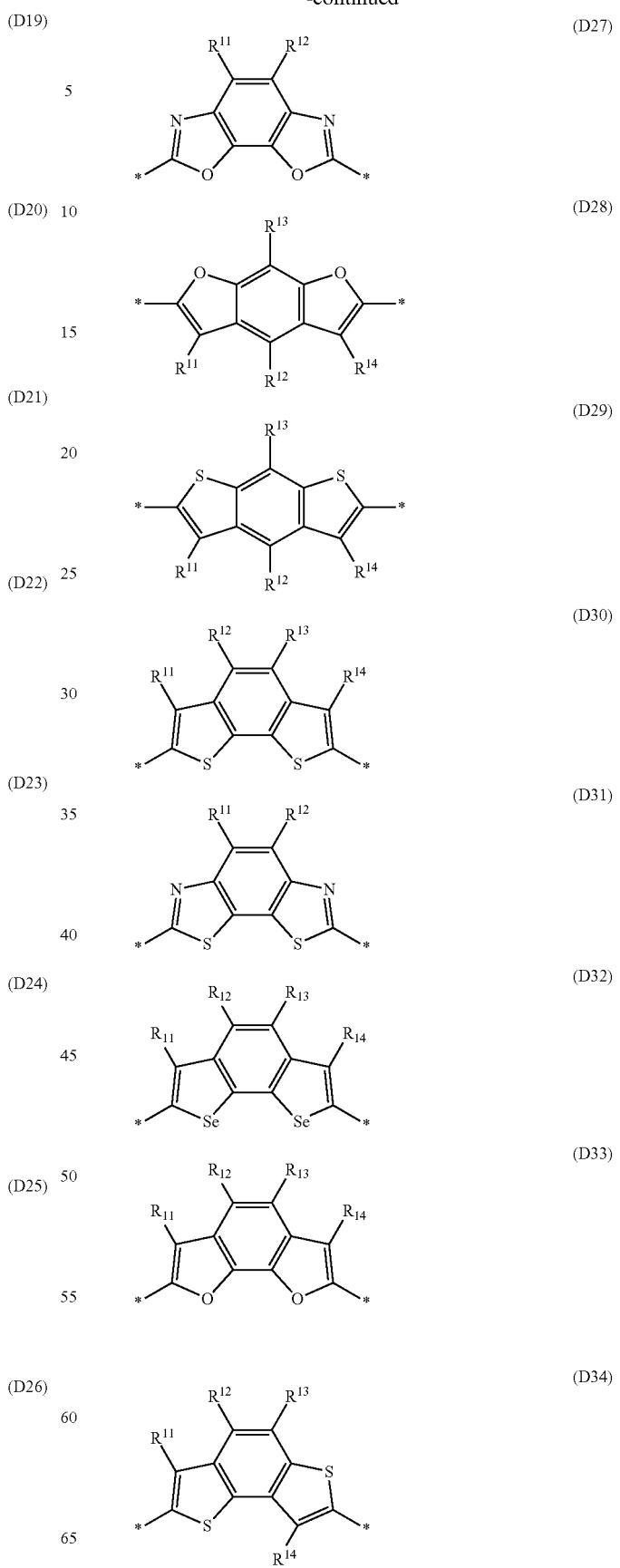

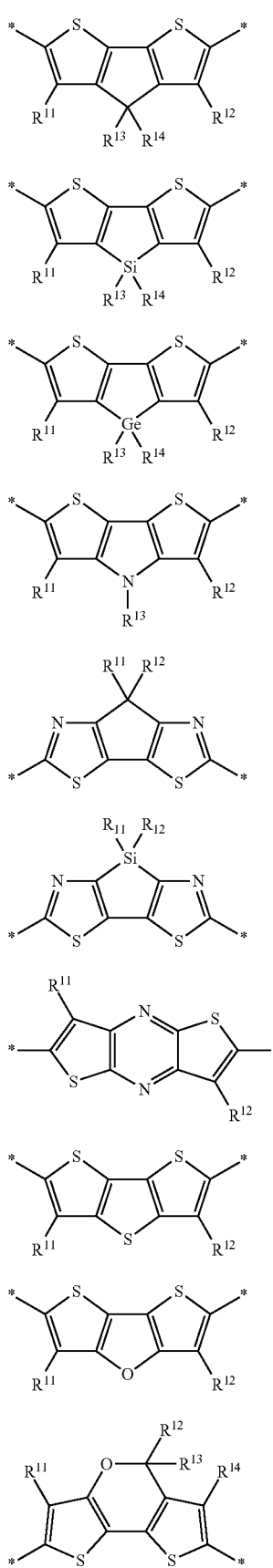
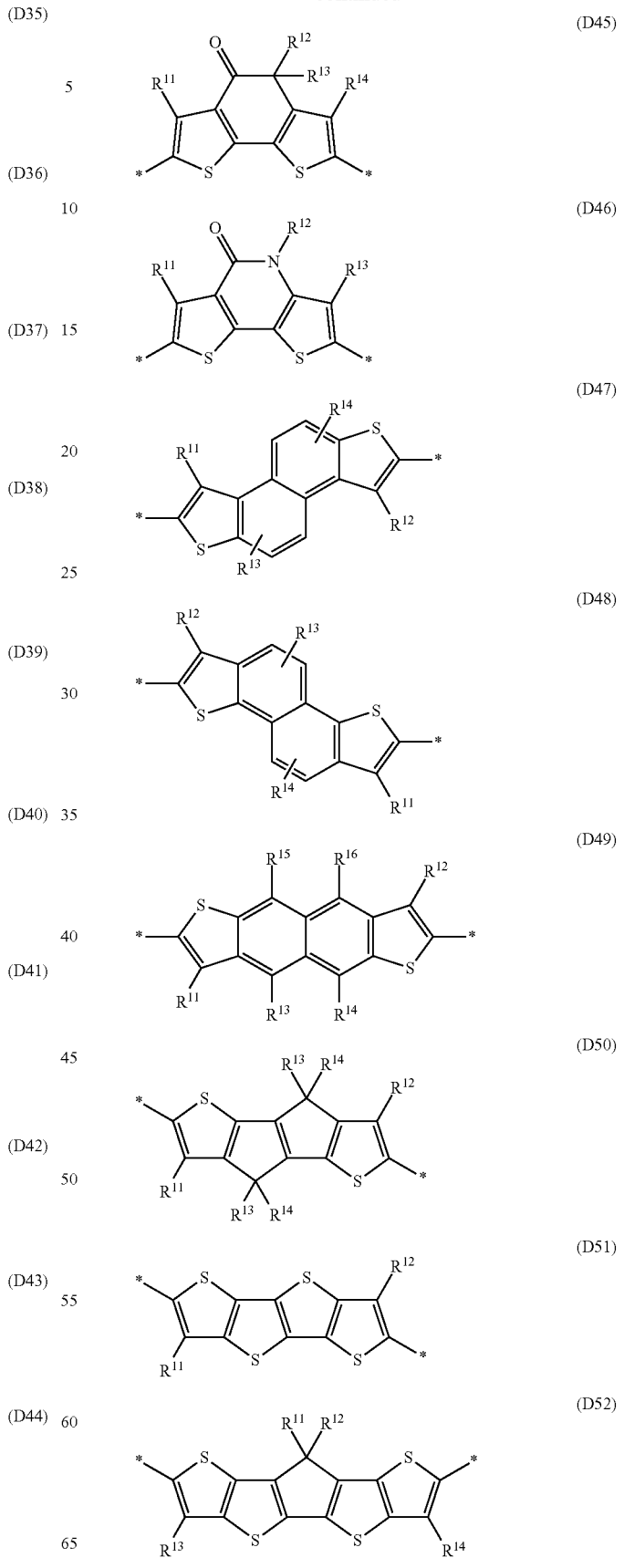

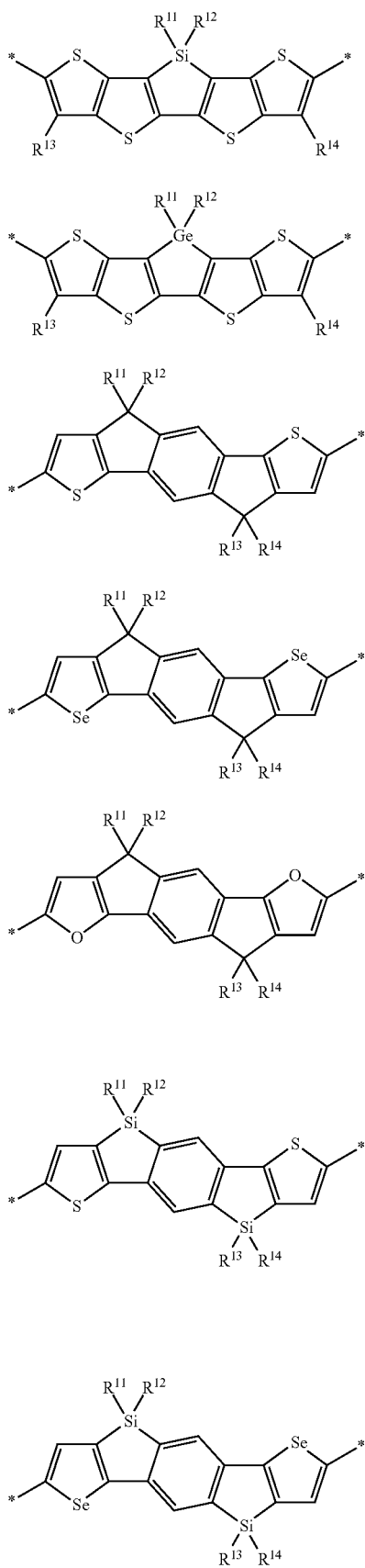
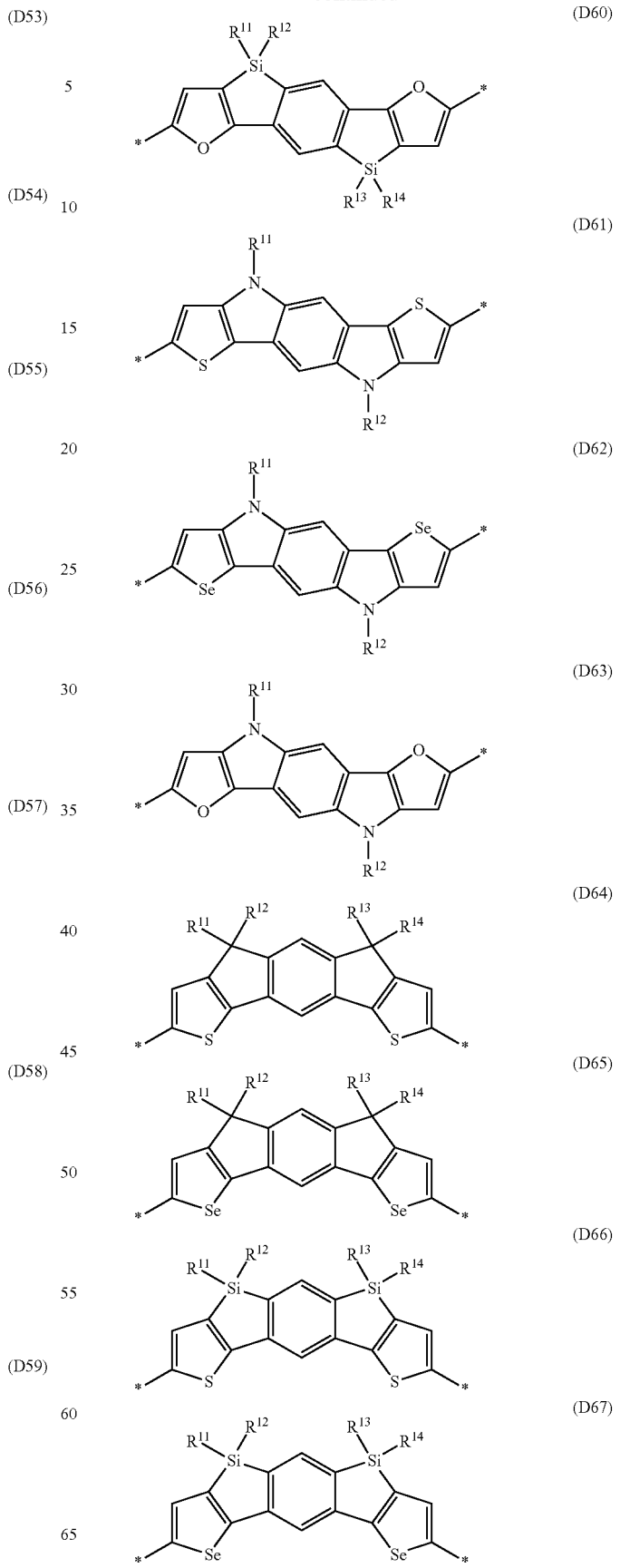

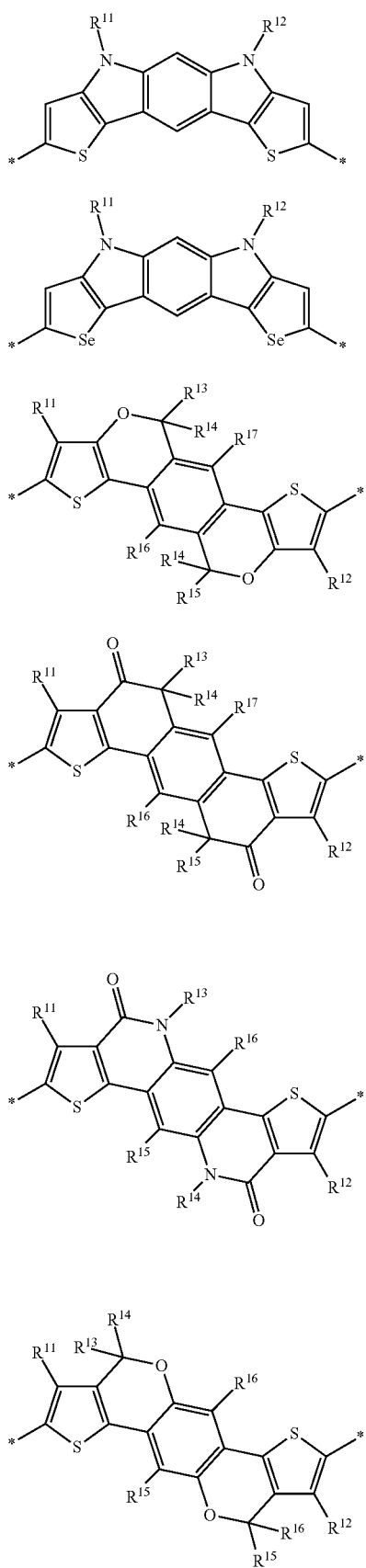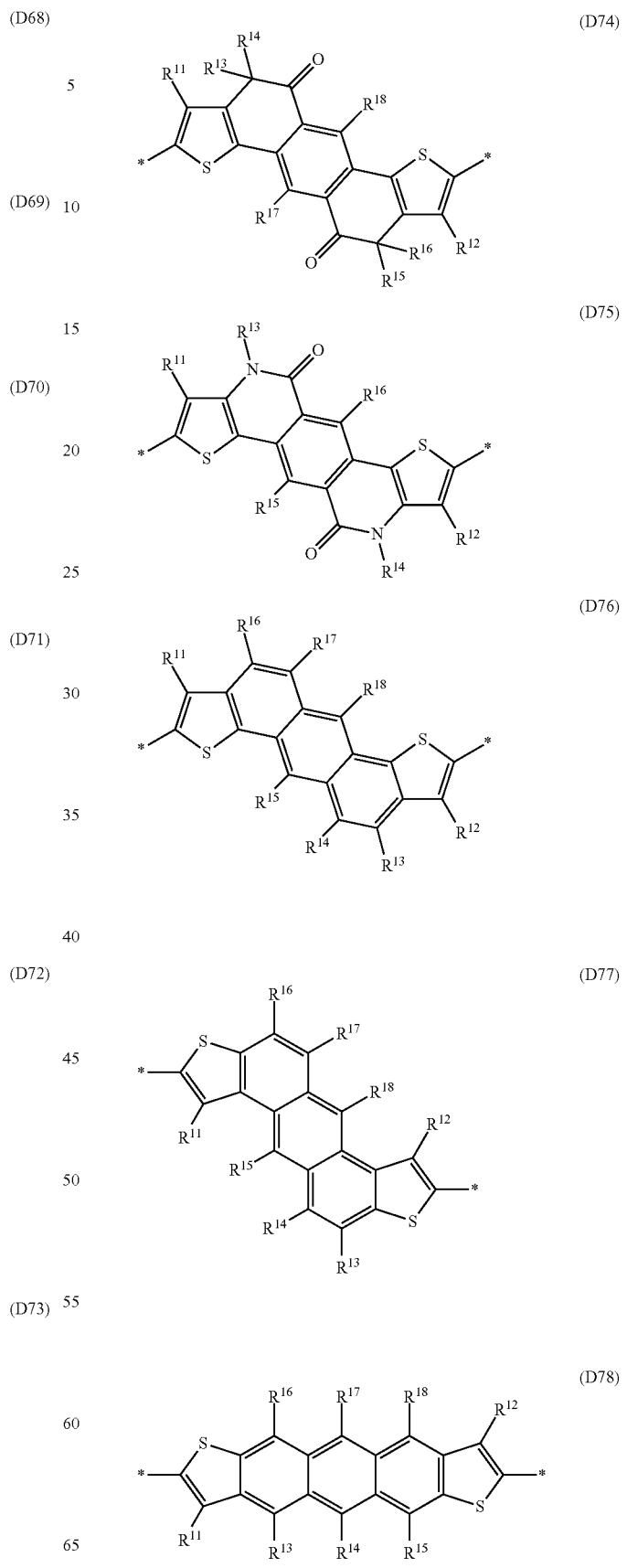

(D79)
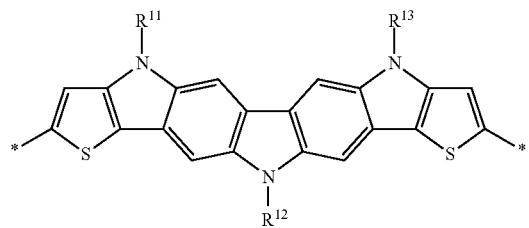
(D80)
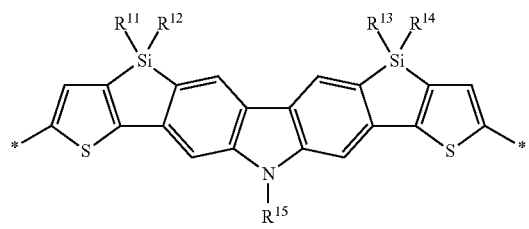
(D81)
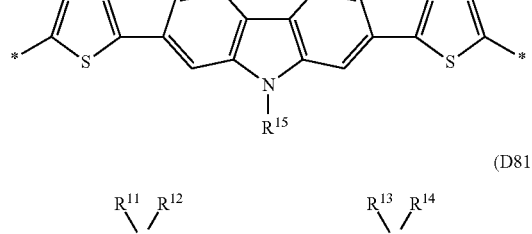
(D82)
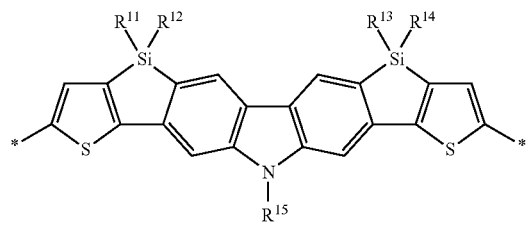
(D83)
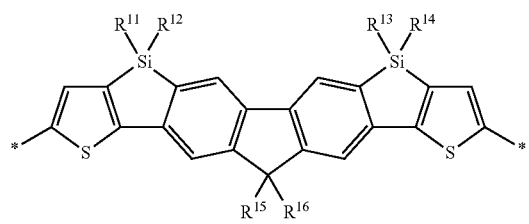
(D84)
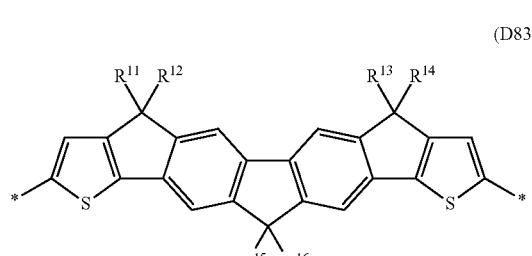
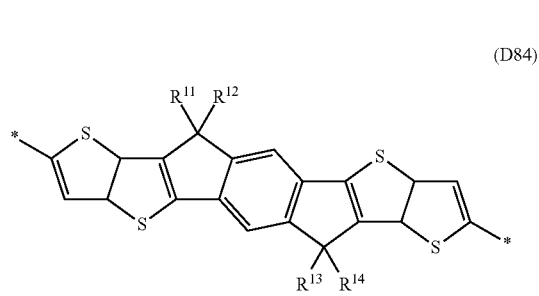
(D85)
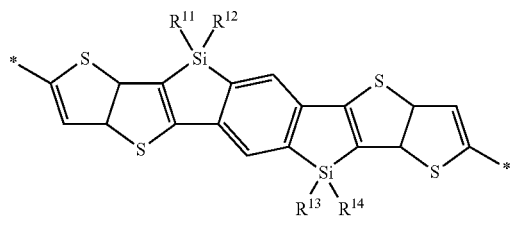
(D86)
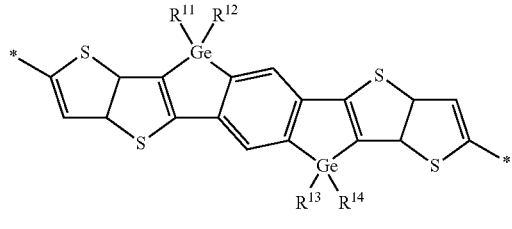
(D87)
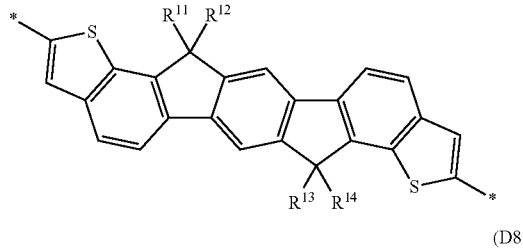
(D88)
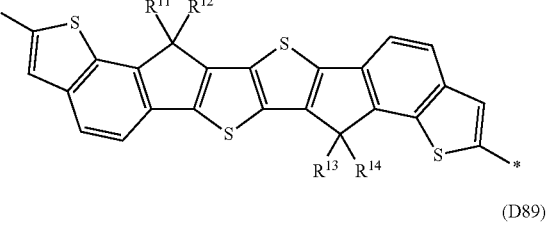
(D89)
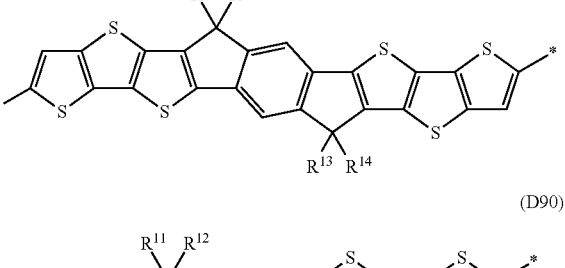
(D90)
(D91)
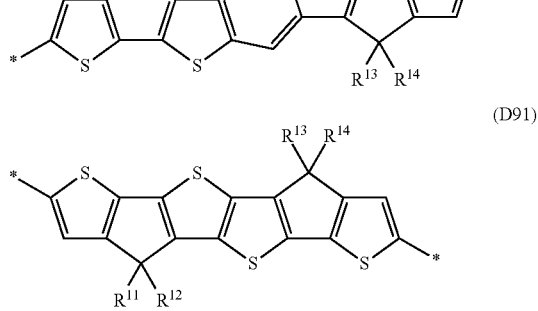

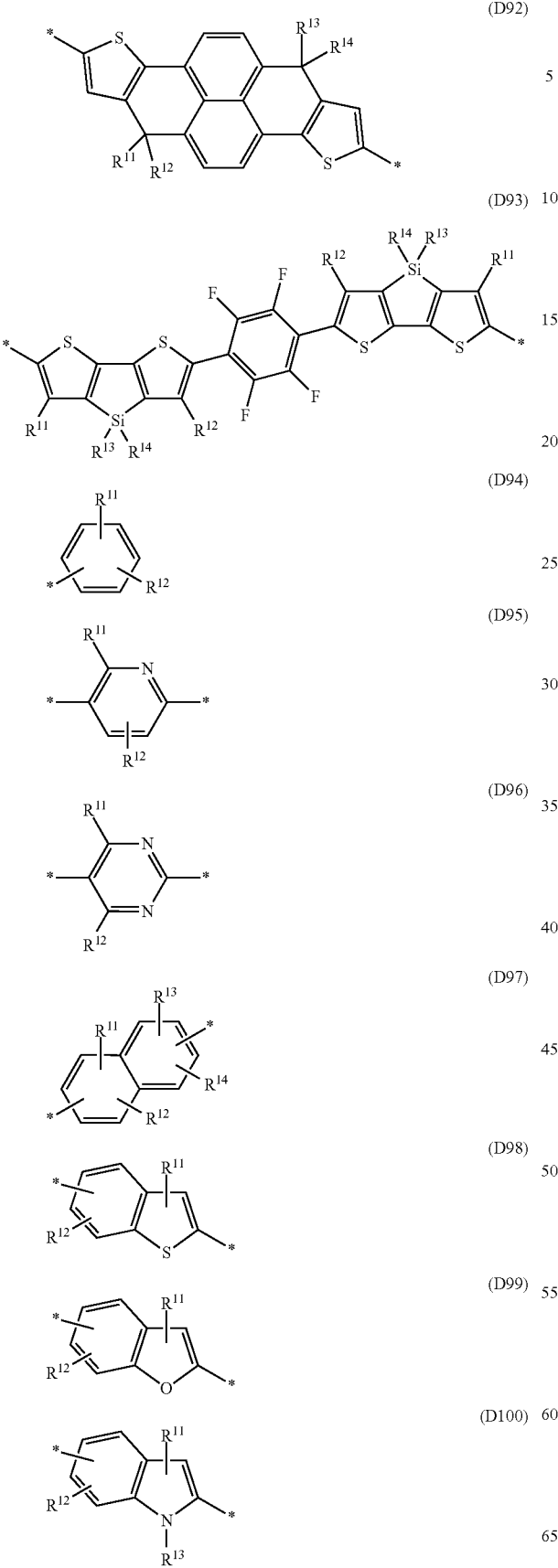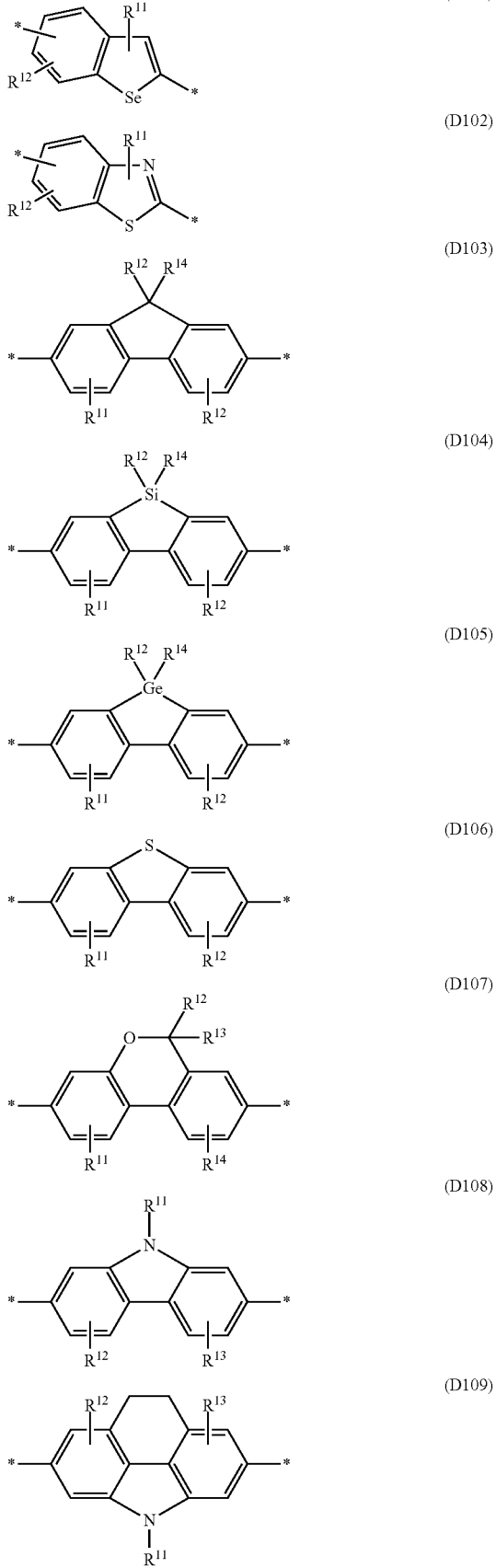

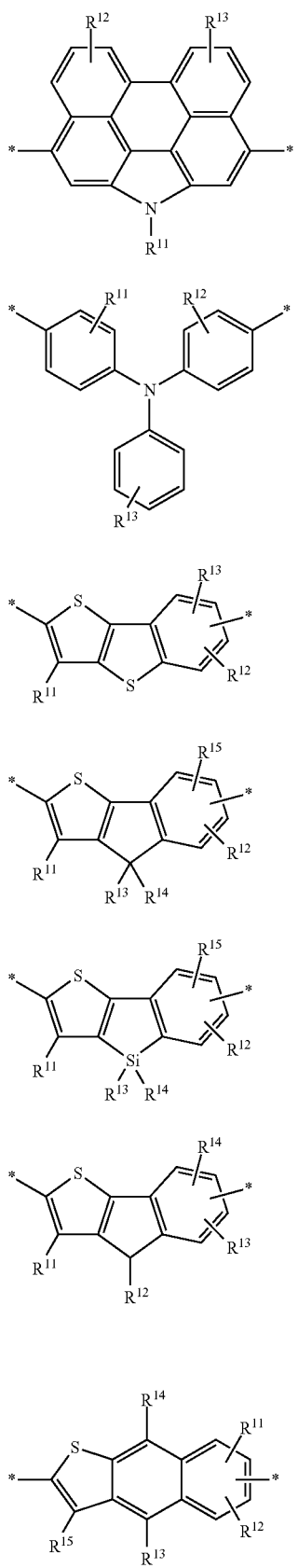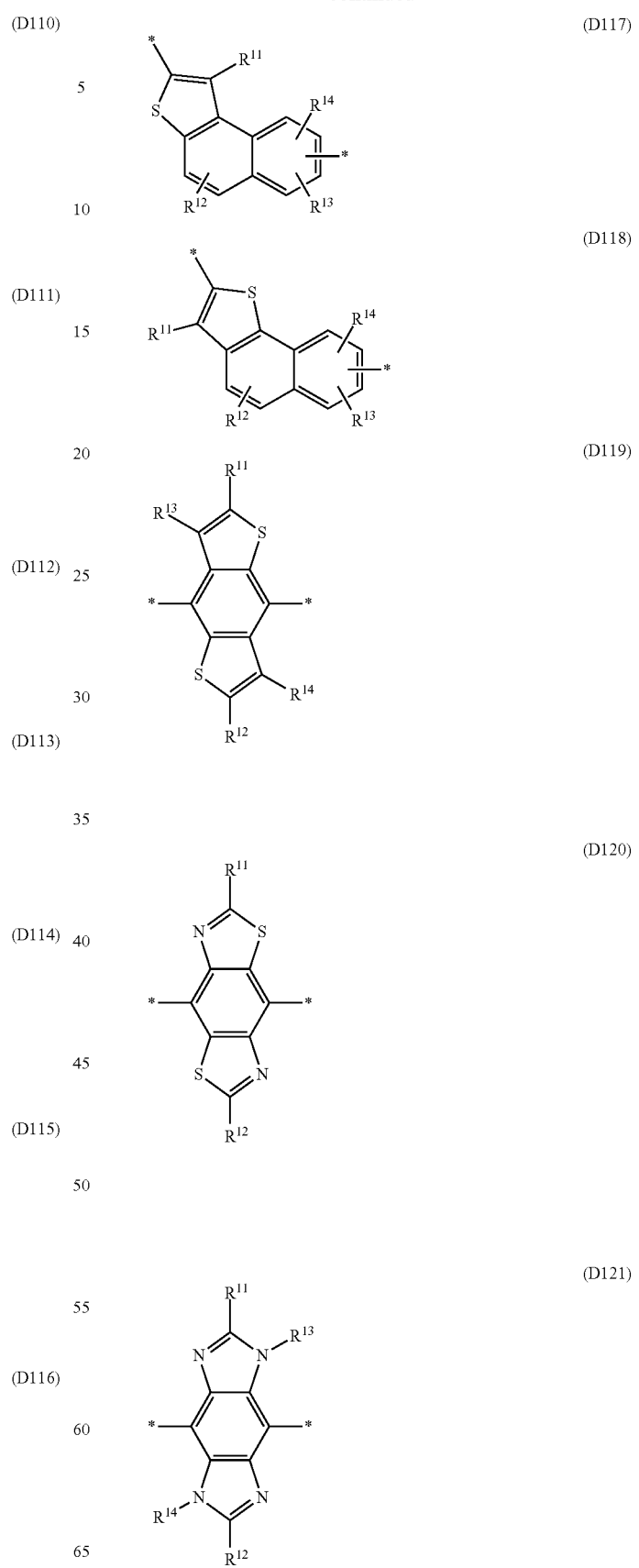

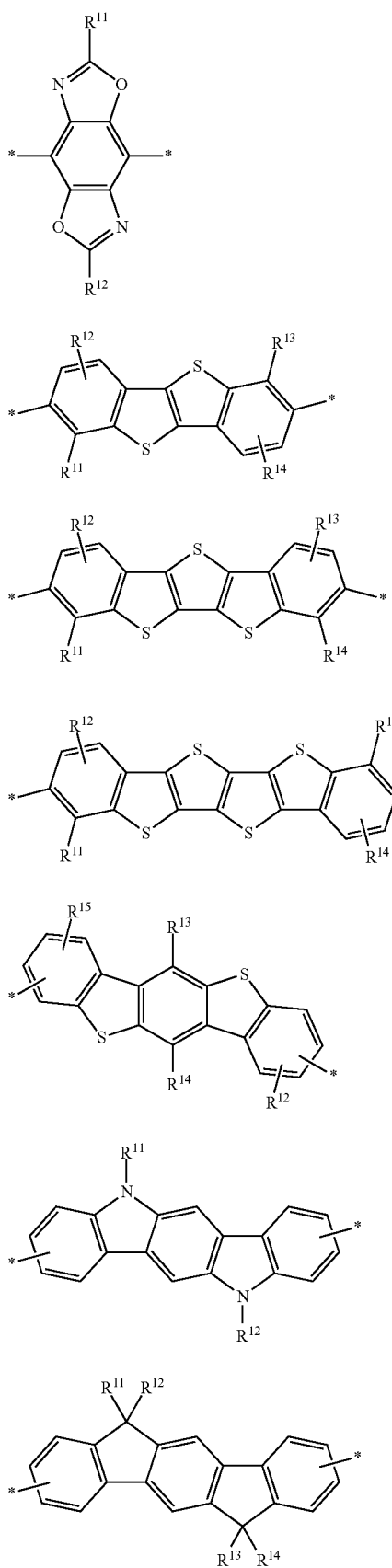
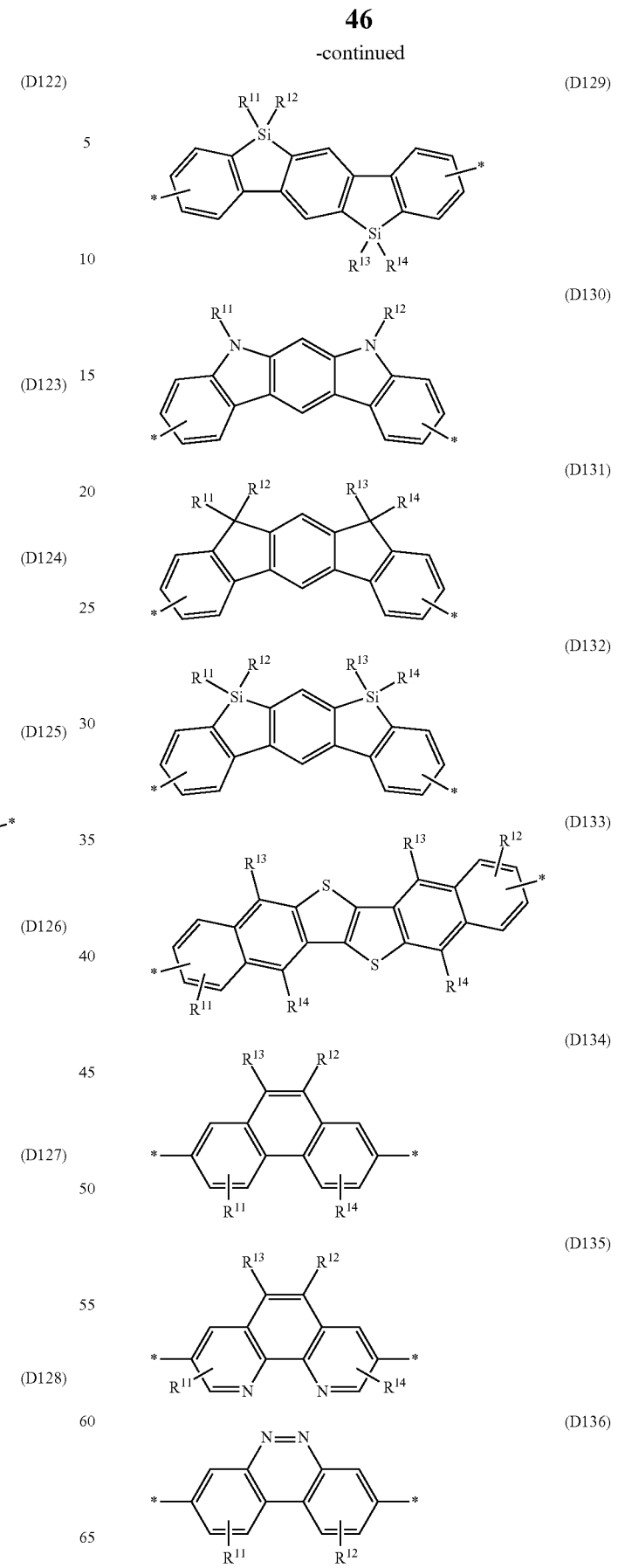

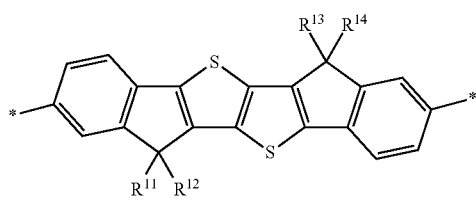 (D137)

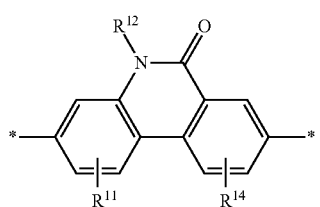 (D138)

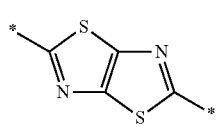 (D139)

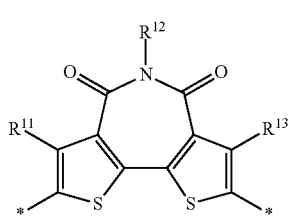 (D140)

wherein $R^{11}$, $R^{12}$, $R^{13}$, $R^{14}$, $R^{15}$, $R^{16}$, $R^{17}$ and $R^{18}$ independently of each other denote H or have one of the meanings of $R^S$ as defined above and below.

Further preferred are repeating units, monomers and polymers of formulae I, IIa, IIb, IIIa. IIIb, IV, IVa-IVm, V, VIa, VIb and their subformulae wherein $A^c$ and/or $Ar^3$ denotes aryl or heteroaryl, preferably having electron acceptor properties, selected from the group consisting of the following formulae

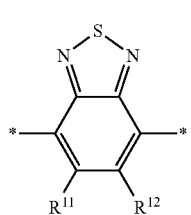 (A1)

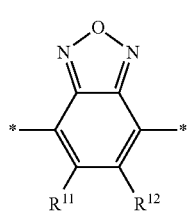 (A2)

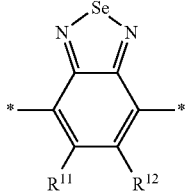 (A3)

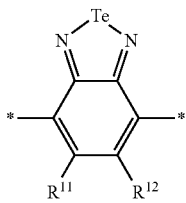 (A4)

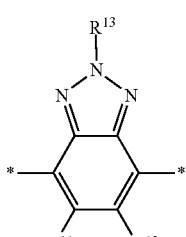 (A5)

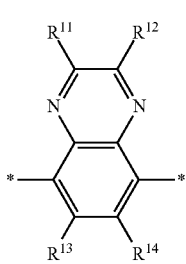 (A6)

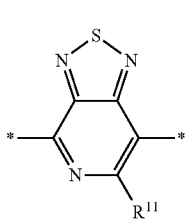 (A7)

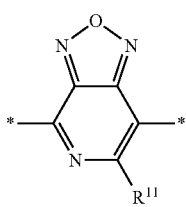 (A8)

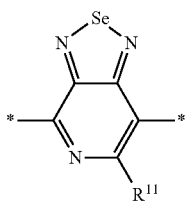 (A9)

-continued
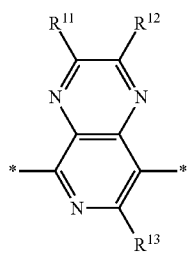
(A10)
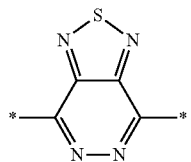
(A11)
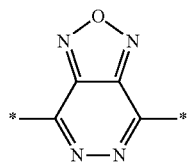
(A12)
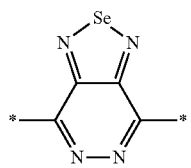
(A13)
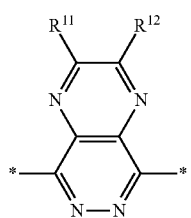
(A14)
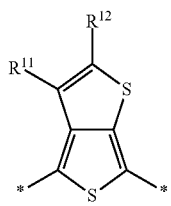
(A15)
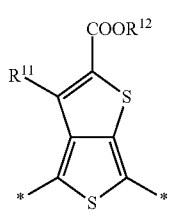
(A16)
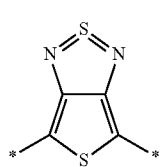
(A17)
-continued
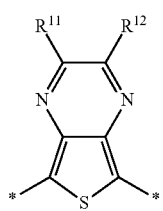
(A18)
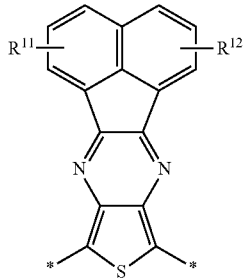
(A19)
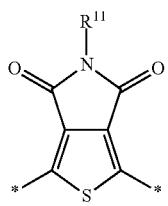
(A20)
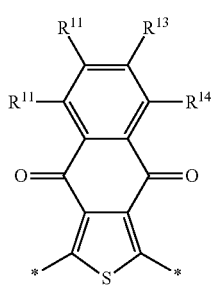
(A21)
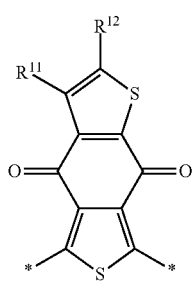
(A22)
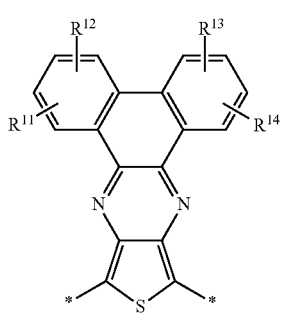
(A23)

-continued
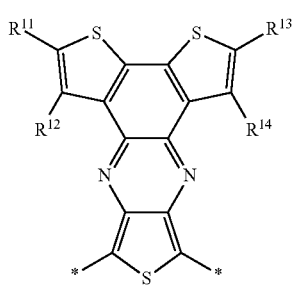
(A24)
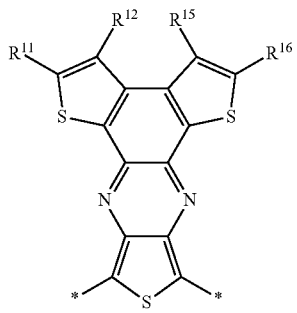
(A25)
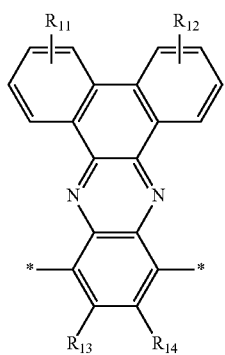
(A26)
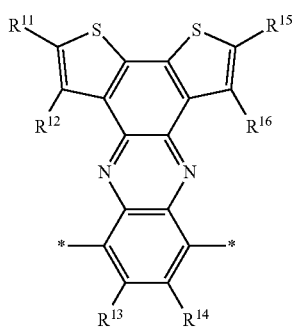
(A27)
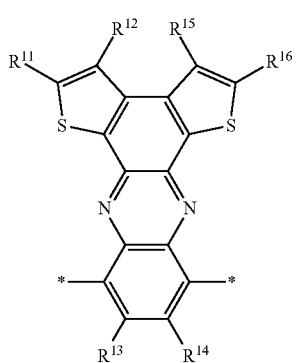
(A28)
-continued
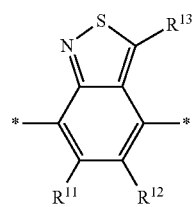
(A29)
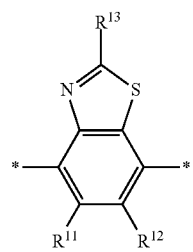
(A30)
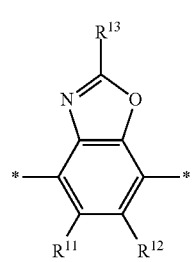
(A31)
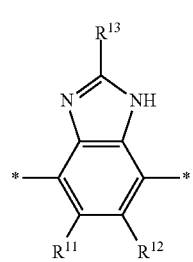
(A32)
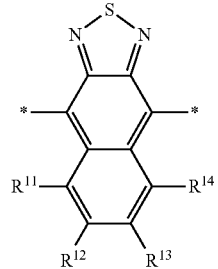
(A33)
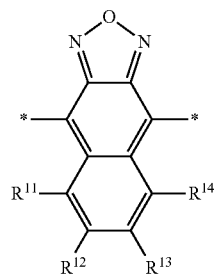
(A34)

-continued
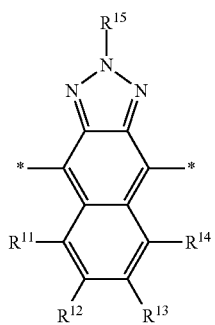
(A35)
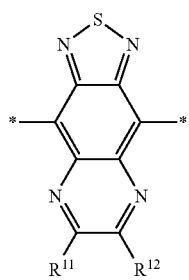
(A36)
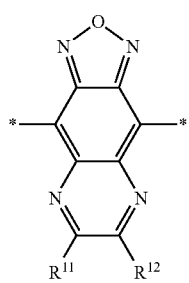
(A37)
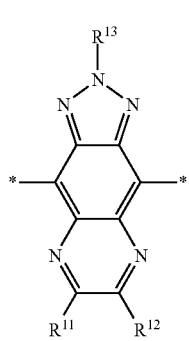
(A38)
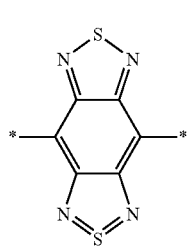
(A39)
-continued
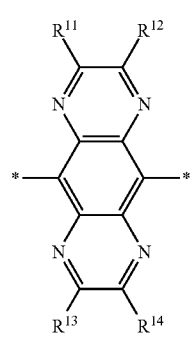
(A40)
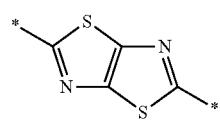
(A41)
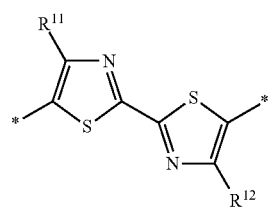
(A42)
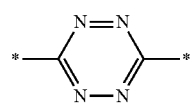
(A43)
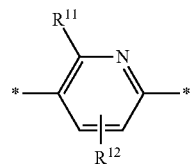
(A44)
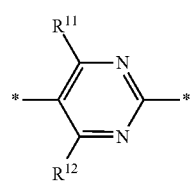
(A45)
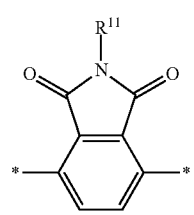
(A46)
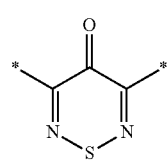
(A47)

(A48) 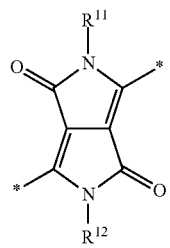
(A49) 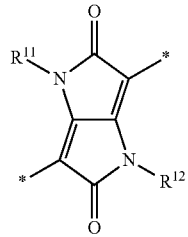
(A50) 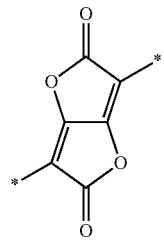
(A51) 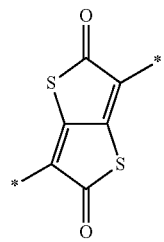
(A52) 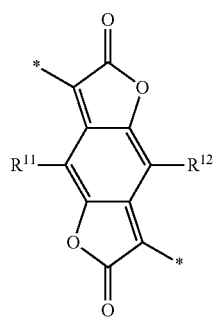
(A53) 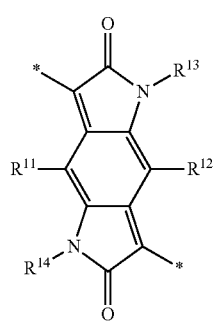
(A54) 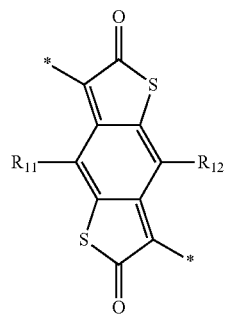
(A55) 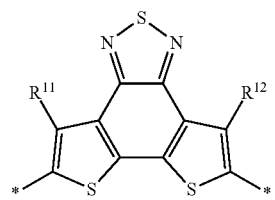
(A56) 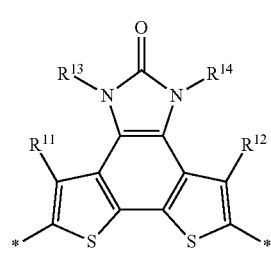
(A57) 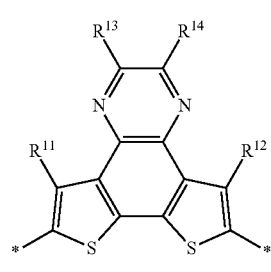
(A58) 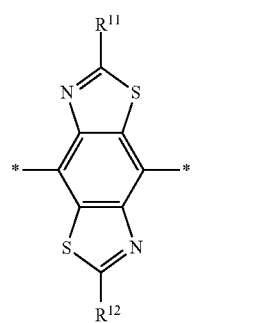

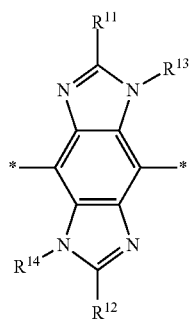
(A59)
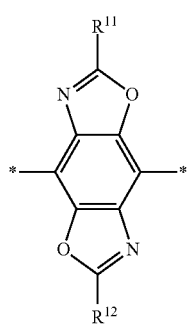
(A60)
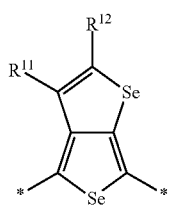
(A61)
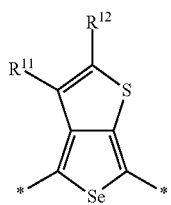
(A62)
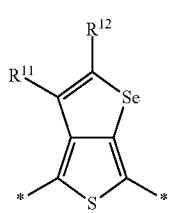
(A63)
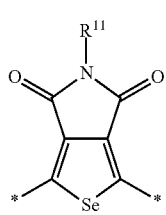
(A64)
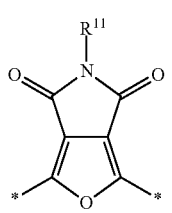
(A65)
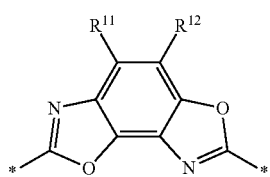
(A66)
(A67)
(A68)
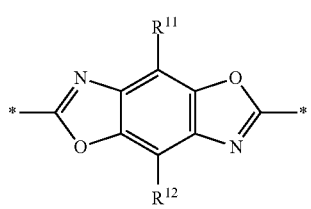
(A69)
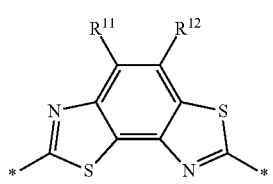
(A70)
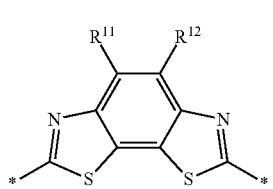
(A71)
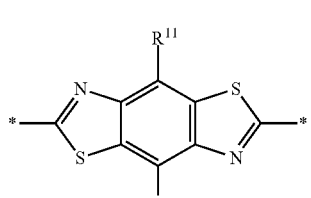
(A72)

-continued
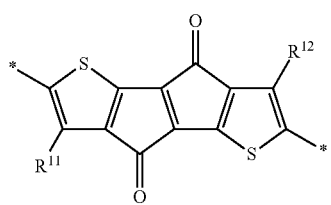
(A73)
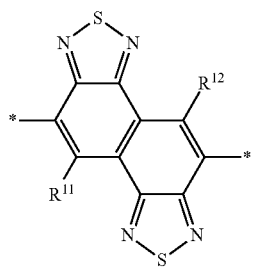
(A74)
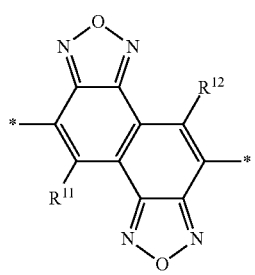
(A75)
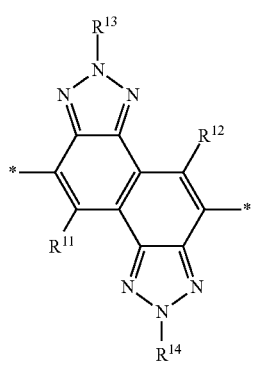
(A76)
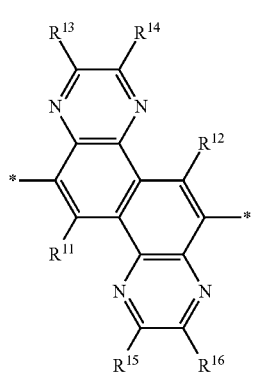
(A77)
-continued
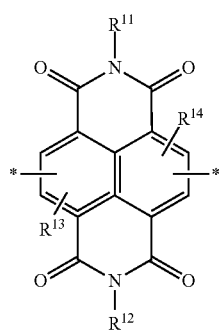
(A78)
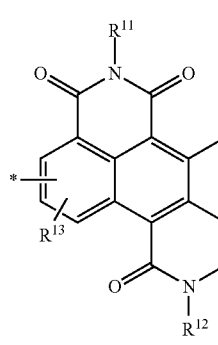
(A79)
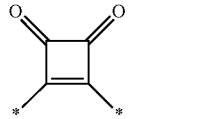
(A80)
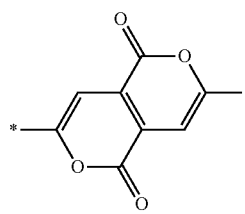
(A81)
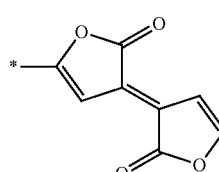
(A82)
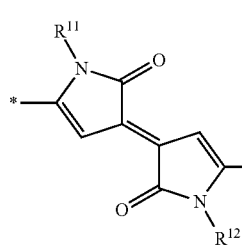
(A83)

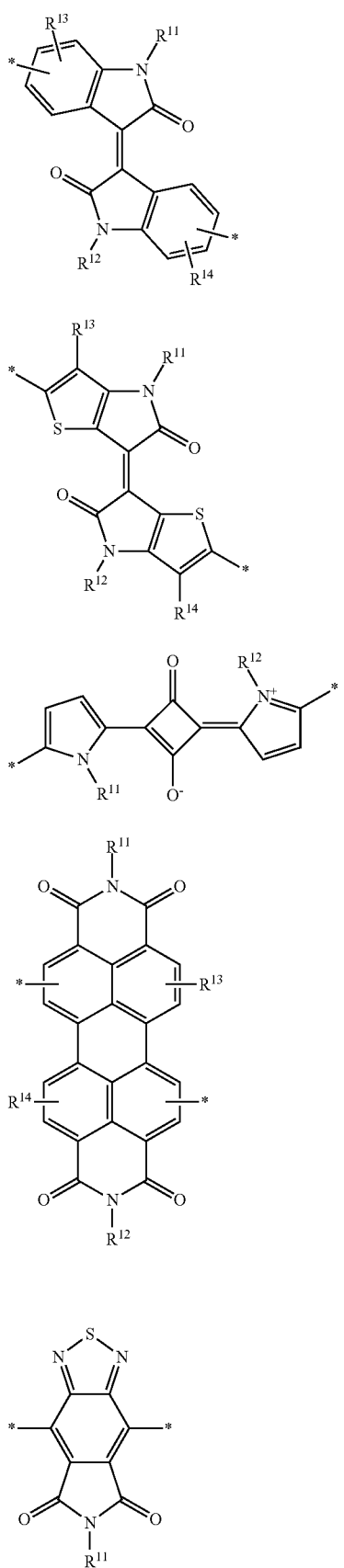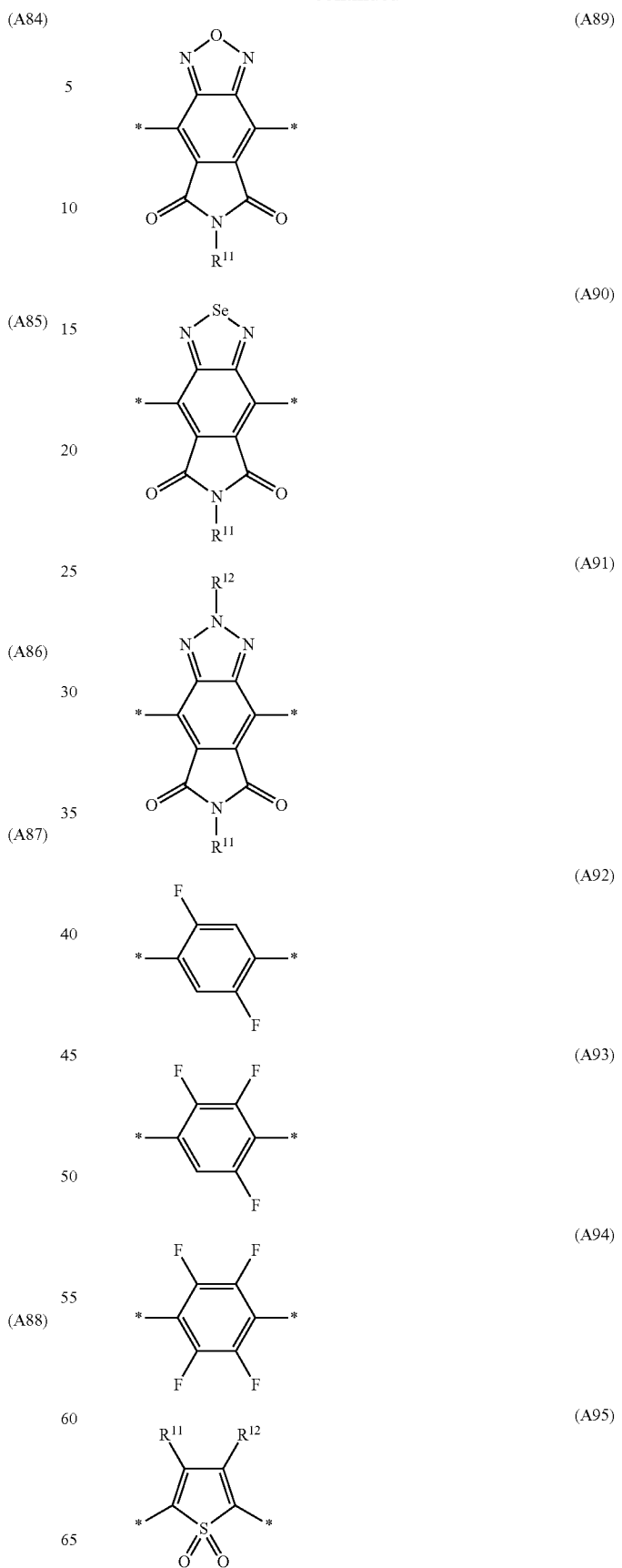

-continued

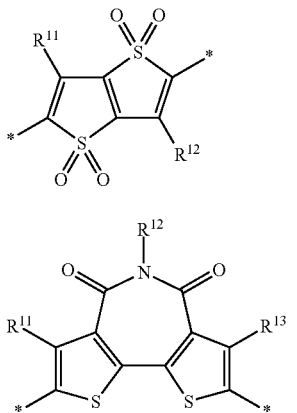
(A96)

(A97)

wherein $R^{11}$, $R^{12}$, $R^{13}$, $R^{14}$, $R^{15}$ and $R^{16}$ independently of each other denote H or have one of the meanings of $R^S$ as defined above and below.

Preferred polymers are selected from the following formulae:

$$*-[U]_n-* \qquad \text{IV1}$$

$$*-[(Ar^1)_a-U-(Ar^2)_c-(Ar^3)_d]_n-* \qquad \text{IV2}$$

$$*-[[(Ar^1)_a-U]_x-[(Ar^2)_c-(Ar^3)_d]_y]_n-* \qquad \text{IV3}$$

$$*-[[(Ar^1)_a]_x-[U]_y-[(Ar^2)_c]_z-[(Ar^3)_d]_w]_n-* \qquad \text{IV4}$$

$$*-[(Ar^1)_a-U]_n-* \qquad \text{IV5}$$

$$*-[(Ar^1)_a-U]_o-[(Ar^1)_a-U]_n-* \qquad \text{IV6}$$

$$*-[(Ar^1)_a-U]_o-[(Ar^2)_c-(Ar^3)_d]_n-* \qquad \text{IV7}$$

$$*-[(Ar^1)_a]_o-[U]_p-[(Ar^2)_c]_n-[(Ar^3)_d]_q-* \qquad \text{IV8}$$

wherein U is unit of formula I or its subformulae as described above and below, $Ar^1$, $Ar^2$, $Ar^3$, a, c and d have the meanings given in formula IIa or one of the preferred meanings given above and below, x, y, z and n have the meanings given in formula IV, w is ≥0 and <1, and o, p and q have one of the meanings given for n. Preferably x, y, z and w are each from 0.1 to 0.9, very preferably from 0.2 to 0.8.

Further preferred polymers are selected of formula V $$R^{21}\text{-chain-}R^{22} \qquad \text{V}$$

wherein "chain" denotes a polymer chain of formulae IV, IVa to IVm, or IV1 to IV9, and $R^{21}$ and $R^{22}$ have independently of each other one of the meanings of $R^S$ as defined above, or denote, independently of each other, H, F, Br, Cl, I, —CH$_2$Cl, —CHO, —CR'=CR''$_2$, —SiR'R''R''', —SiR'X'X'', —SiR'R''X', —SnR'R''R''', —BR'R'', —B(OR') (OR''), —B(OH)$_2$, —O—SO$_2$—R', —C≡CH, —C≡C—SiR'$_3$, —ZnX' or an endcap group, X' and X'' denote halogen, R', R'' and R''' have independently of each other one of the meanings of $R^0$ given in formula I, and two of R', R'' and R''' may also form a cyclosilyl, cyclostannyl, cycloborane or cycloboronate group with 2 to 20 C atoms together with the respective hetero atom to which they are attached.

Preferred endcap groups $R^{21}$ and $R^{22}$ are H, $C_{1-20}$ alkyl, or optionally substituted $C_{6-12}$ aryl or $C_{2-10}$ heteroaryl, very preferably H or phenyl.

Formulae IV, IVa to IVm, IV1 to IV8 and V include block copolymers, random or statistical copolymers and alternating copolymers.

The invention further relates to monomers of formula VIa and VIb

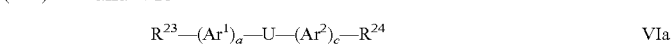
$$R^{23}-(Ar^1)_a-U-(Ar^2)_c-R^{24} \qquad \text{VIa}$$

$$R^{23}-U-(Ar^1)_a-U-R^{24} \qquad \text{VIb}$$

wherein
U, $Ar^1$, $Ar^2$, a and b have the meanings of formula IIa, or one of the preferred meanings as described above and below,
$R^{23}$ and $R^{24}$ are, preferably independently of each other, selected from the group consisting of H, Cl, Br, I, O-tosylate, O-triflate, O-mesylate, O-nona-flate, —SiMe$_2$F, —SiMeF$_2$, —O—SO$_2$Z$^1$, —B(OZ$^2$)$_2$, —CZ$^3$=C(Z$^3$)$_2$, —C≡CH, —C≡CSi(Z$^1$)$_3$, —ZnX$^0$ and —Sn(Z$^4$)$_3$, wherein X$^0$ is halogen, preferably Cl, Br or I, Z$^{1-4}$ are selected from the group consisting of alkyl and aryl, each being optionally substituted, and two groups Z$^2$ may also together form a cycloboronate group with 2 to 20 C atoms together with the B and O atoms.

Very preferred monomers are selected from the following formulae $$R^{23}-U-R^{24} \qquad \text{VI1}$$

$$R^{23}-Ar^1-U-R^{24} \qquad \text{VI2}$$

$$R^{23}-U-Ar^2-R^{24} \qquad \text{VI3}$$

$$R^{23}-U-Ar^1-U-R^{24} \qquad \text{VI4}$$

$$R^{23}-Ar^1-U-Ar^2-R^{24} \qquad \text{VI5}$$

$$R^{23}-U-A^c-R^{24} \qquad \text{VI6}$$

wherein U, $A^c$, $Ar^1$, $Ar^2$, $R^{23}$ and $R^{24}$ are as defined in formula IIIa and VI.

Small molecule compounds and oligomers according to the present invention are preferably selected of formula VII $$R^{T1}-(Ar^7)_h-(Ar^6)_g-[(Ar^5)_f-(Ar^4)_e-U-(Ar^8)_i-(Ar^9)_k]_l-(Ar^{10})_j-(Ar^{11})_m-R^{T2} \qquad \text{VII}$$

wherein
U is a unit of formula I or its subformulae I1 to I22,
$Ar^{4-11}$ independently of each other denote —CY$^1$=CY$^2$—, —C≡C—, or aryl or heteroaryl that has 5 to 30 ring atoms and is unsubstituted or substituted by one or more groups $R^S$ as defined in formula I, and one or more of $Ar^{4-11}$ may also denote U as defined in formula I,
$Y^1$, $Y^2$ independently of each other denote H, F, Cl or CN,
$R^{T1,T2}$ independently of each other denote H, F, Cl, Br, —CN, —CF$_3$, R, —CF$_2$—R, —O—R, —S—R, —SO$_2$—R, —SO$_3$—R—C(O)—R, —C(O)—H, —C(S)—R, —C(O)—CF$_2$—R, —C(O)—OR, —C(S)—OR, —O—C(O)—R, —O—C(S)—R, —C(O)—SR, —S—C(O)—R, —C(O)NRR', —NR'—C(O)—R, —NHR, —NRR', —SO$_2$—R, —CR'=CR''R''', —C≡C—R', —C≡C—SiR'R''R''', —SiR'R''R''', —CH=CH(CN), —CH=C(CN)$_2$, —C(CN)=C(CN)$_2$, —CH=C(CN)(Ar$^{12}$), —CH=C(CN)—COOR, —CH=C(COOR)$_2$, CH=C(CONRR')$_2$,

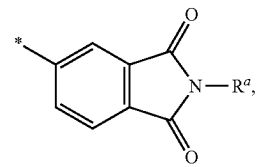

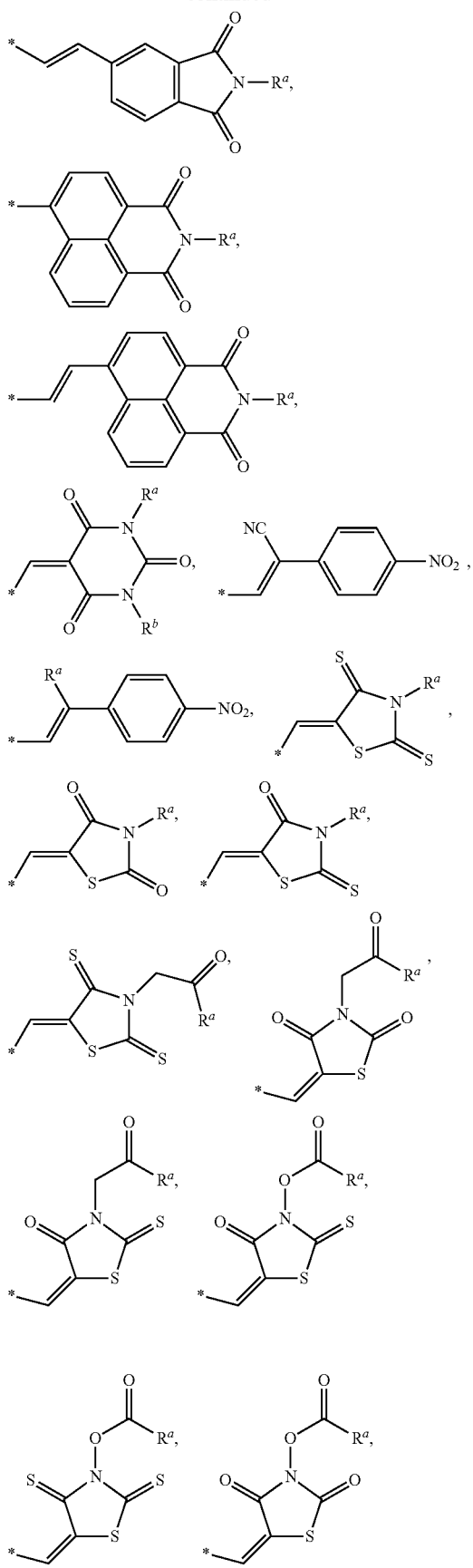
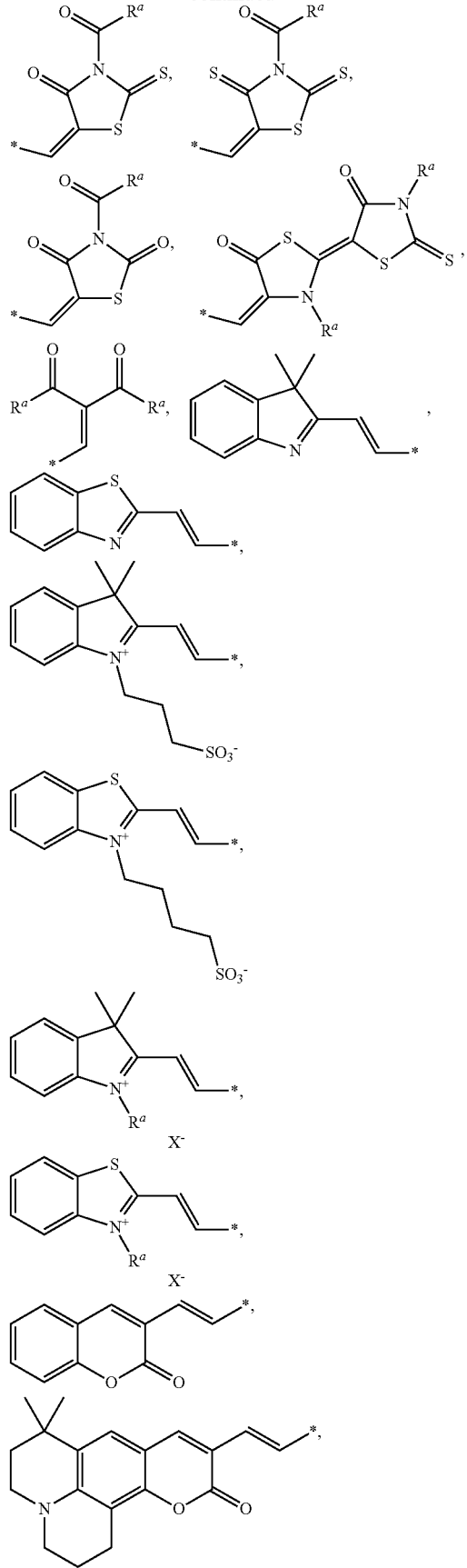

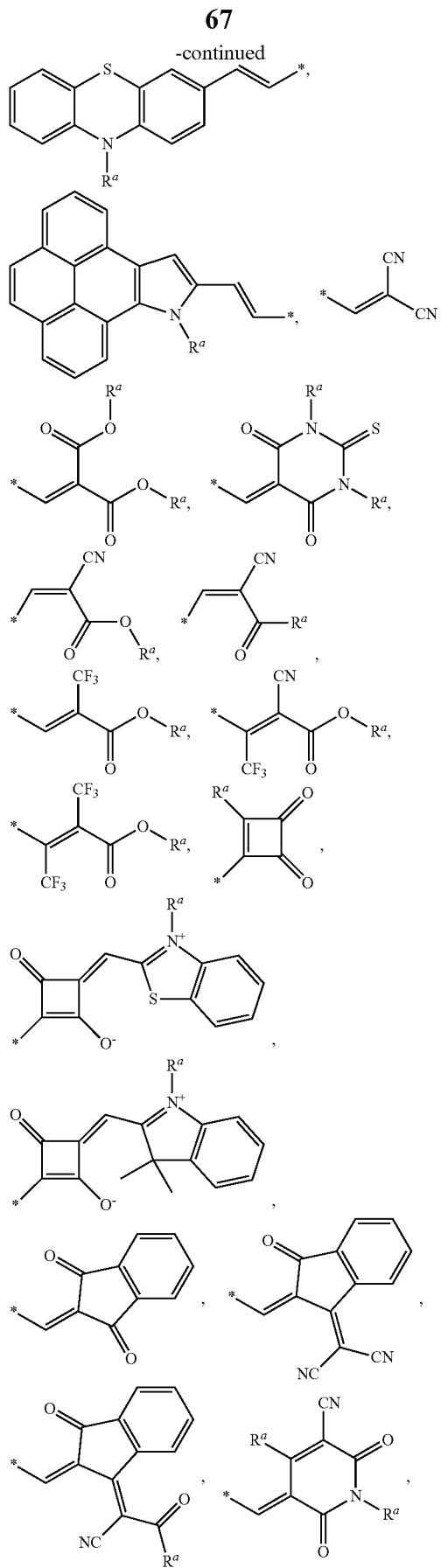

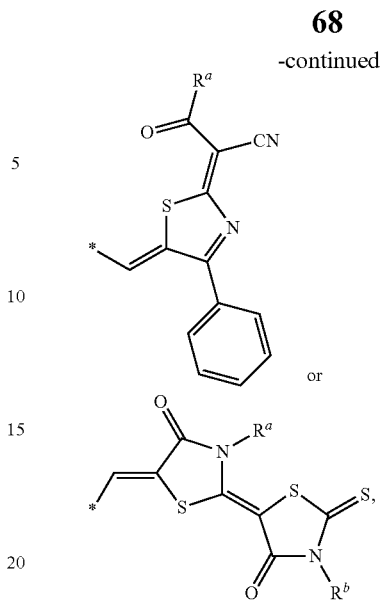

R$^a$, R$^b$ are independently of each other aryl or heteroaryl, each having from 4 to 30 ring atoms and being unsubstituted or substituted with one or more groups R or R$^1$, Ar$^{12}$ is aryl or heteroaryl, each having from 4 to 30 ring atoms and being unsubstituted or substituted with one or more groups R$^1$, R is alkyl with 1 to 30 C atoms which is straight-chain, branched or cyclic, and is unsubstituted, substituted with one or more F or Cl atoms or CN groups, or perfluorinated, and in which one or more C atoms are optionally replaced by —O—, —S—, —C(O)—, —C(S)—, S—SiR$^o$R$^{oo}$—, —NR$^o$R$^{oo}$—, —CHR$^o$=CR$^{oo}$— or —C≡C— such that O- and/or S-atoms are not directly linked to each other, R$^o$, R$^{oo}$ have the meanings given in formula I and preferably denote, independently of each other, H or C$_{1-20}$ alkyl, R', R'', R''' independently of each other have one of the meanings of R$^o$, e, f, g, h, i, k, l, m are independently of each other 0 or 1, with at least one of e, f, g, h, i, k, l, m being 1, t is 1, 2 or 3.

Especially preferred groups Ar$^{4-12}$ in the oligomers and small molecules according to the present invention are selected from the formulae D1-D138 and A1-A96 above.

Further preferred repeating units, monomers, oligomers, polymers and small molecules of formulae I-VII and their subformulae are selected from the following list of preferred embodiments or any combination thereof:

y is >0 and <1 and z is 0,
y is >0 and <1 and z is >0 and <1,
n is at least 5, preferably at least 10, very preferably at least 50, and up to 2,000, preferably up to 500.
M$_w$ is at least 5,000, preferably at least 8,000, very preferably at least 10,000, and preferably up to 300,000, very preferably up to 100,000,
all groups R$^S$ denote H,
at least one group R$^S$ is different from H,
R$^S$ is selected, on each occurrence identically or differently, from the group consisting of primary alkyl with 1 to 30 C atoms, secondary alkyl with 3 to 30 C atoms, and tertiary alkyl with 4 to 30 C atoms, wherein in all these groups one or more H atoms are optionally replaced by F, $R^S$ is selected, on each occurrence identically or differently, from the group consisting of aryl and heteroaryl, each of which is optionally fluorinated, alkylated or alkoxylated and has 4 to 30 ring atoms, $R^S$ is selected, on each occurrence identically or differently, from the group consisting of aryl and heteroaryl, each of which is optionally fluorinated, or alkylated and has 4 to 30 ring atoms, $R^S$ is selected, on each occurrence identically or differently, from the group consisting of primary alkoxy or sulfanylalkyl with 1 to 30 C atoms, secondary alkoxy or sulfanylalkyl with 3 to 30 C atoms, and tertiary alkoxy or sulfanylalkyl with 4 to 30 C atoms, wherein in all these groups one or more H atoms are optionally replaced by F, $R^S$ is selected, on each occurrence identically or differently, from the group consisting of aryloxy and heteroaryloxy, each of which is optionally alkylated or alkoxylated and has 4 to 30 ring atoms, $R^S$ is selected, on each occurrence identically or differently, from the group consisting of alkylcarbonyl, alkoxycarbonyl and alkylcarbonyloxy, all of which are straight-chain or branched, are optionally fluorinated, and have from 1 to 30 C atoms, $R^S$ denotes, on each occurrence identically or differently, F, Cl, Br, I, CN, $R^9$, —C(O)—$R^9$, —C(O)—O—$R^9$, or —O—C(O)—$R^9$, —SO$_2$—$R^9$, —SO$_3$—$R^9$, wherein $R^9$ is straight-chain, branched or cyclic alkyl with 1 to 30 C atoms, in which one or more non-adjacent C atoms are optionally replaced by —O—, —S—, —C(O)—, —C(O)—O—, —O—C(O)—, —O—C(O)—O—, —SO$_2$—, —SO$_3$—, —CR$^0$=CR$^{00}$— or —C≡C— and in which one or more H atoms are optionally replaced by F, Cl, Br, I or CN, or $R^9$ is aryl or heteroaryl having 4 to 30 ring atoms which is unsubstituted or which is substituted by one or more halogen atoms or by one or more groups $R^1$ as defined above, $R^0$ and $R^{00}$ are selected from H or $C_1$-$C_{10}$-alkyl, $R^{21}$ and $R^{22}$ are independently of each other selected from H, halogen, —CH$_2$Cl, —CHO, —CH=CH$_2$— SiR'R''R''', —SnR'R''R''', —BR'R'', —B(OR')(OR''), —B(OH)$_2$, P-Sp, $C_1$-$C_{20}$-alkyl, $C_1$-$C_{20}$-alkoxy, $C_2$-$C_{20}$-alkenyl, $C_1$-$C_{20}$-fluoroalkyl and optionally substituted aryl or heteroaryl, preferably phenyl, $R^{23}$ and $R^{24}$ are independently of each other selected from the group consisting of Cl, Br, I, O-tosylate, O-triflate, O-mesylate, O-nonaflate, —SiMe$_2$F, —SiMeF$_2$, —O—SO$_2$Z$^1$, —B(OZ$^2$)$_2$, —CZ$^3$=C(Z$^4$)$_2$, —C≡CH, C≡CSi(Z$^1$)$_3$, —ZnX$^0$ and —Sn(Z$^4$)$_3$, wherein X$^0$ is halogen, Z$^{1-4}$ are selected from the group consisting of alkyl and aryl, each being optionally substituted, and two groups Z$^2$ may also form a cyclic group.

The compounds of the present invention can be synthesized according to or in analogy to methods that are known to the skilled person and are described in the literature. Other methods of preparation can be taken from the examples.

For example, the polymers of the present invention can be suitably prepared by aryl-aryl coupling reactions, such as Yamamoto coupling, Suzuki coupling, Stille coupling, Sonogashira coupling, Heck coupling or Buchwald coupling. Suzuki coupling, Stille coupling and Yamamoto coupling are especially preferred. The monomers which are polymerised to form the repeat units of the polymers can be prepared according to methods which are known to the person skilled in the art.

Preferably the polymers are prepared from monomers of formula VIa or VIb or their preferred subformulae as described above and below.

Another aspect of the invention is a process for preparing a polymer by coupling one or more identical or different monomeric units of formula I or monomers of formula VIa or VIb with each other and/or with one or more co-monomers in a polymerisation reaction, preferably in an aryl-aryl coupling reaction.

Suitable and preferred comonomers are selected from the following formulae

$R^{23}$—(Ar$^1$)$_a$-A$^c$-(Ar$^2$)$_c$—R$^{24}$    VIII

$R^{23}$—Ar$^1$—R$^{24}$    IX

$R^{23}$—Ar$^3$—R$^{24}$    X

$R^{23}$-A$^c$-R$^{24}$    XI wherein Ar$^1$, Ar$^2$, Ar$^3$, a and c have one of the meanings of formula IIa or one of the preferred meanings given above and below, A$^c$ has one of the meanings of formula IIIa or one of the preferred meanings given above and below, and R$^{23}$ and R$^{24}$ have one of meanings of formula VI or one of the preferred meanings given above and below.

Very preferred is a process for preparing a polymer by coupling one or more monomers selected from formula VIa or VIb with one or more monomers of formula VIII, and optionally with one or more monomers selected from formula IX, X and XI, in an aryl-aryl coupling reaction, wherein preferably R$^{23}$ and R$^{24}$ are selected from Cl, Br, I, —B(OZ$^2$)$_2$ and —Sn(Z$^4$)$_3$.

For example, preferred embodiments of the present invention relate to a) a process of preparing a polymer by coupling a monomer of formula VII

$R^{23}$—Ar$^1$—U—Ar$^2$—R$^{24}$    VII with a monomer of formula IX

$R^{23}$—Ar$^1$—R$^{24}$    IX in an aryl-aryl coupling reaction, or b) a process of preparing a polymer by coupling a monomer of formula VI2

$R^{23}$—U—R$^{24}$    VI2 with a monomer of formula VIII1

$R^{23}$—Ar$^1$-A$^c$-Ar$^2$—R$^{24}$    VIII1 in an aryl-aryl coupling reaction, or c) a process of preparing a polymer by coupling a monomer of formula VI2

$R^{23}$—U—R$^{24}$    VI2 with a monomer of formula VIII-2

$R^{23}$-A$^c$-R$^{24}$    VIII2 in an aryl-aryl coupling reaction, or d) a process of preparing a polymer by coupling a monomer of formula VI2

$R^{23}$—U—R$^{24}$    VI2 with a monomer of formula VIII2

$R^{23}$-A$^c$-R$^{24}$    VIII2 and a monomer of formula IX $$R^{23}\text{—}Ar^1\text{—}R^{24} \quad \text{IX}$$

in an aryl-aryl coupling reaction,
e) a process of preparing a polymer by coupling a monomer of formula VI1

$$R^{23}\text{—}U\text{—}Ar^1\text{—}U\text{—}R^{24} \quad \text{VI5}$$

with a monomer of formula IX $$R^{23}\text{—}Ar^1\text{—}R^{24} \quad \text{IX}$$

in an aryl-aryl coupling reaction,
or
f) a process of preparing a polymer by coupling a monomer of formula VI2

$$R^{23}\text{—}U\text{—}R^{24} \quad \text{VI2}$$

with a monomer of formula IX $$R^{23}\text{—}Ar^1\text{—}R^{24} \quad \text{IX}$$

and a monomer of formula X $$R^{23}\text{—}Ar^3\text{—}R^{24} \quad \text{X}$$

in an aryl-aryl coupling reaction,
or
g) a process of preparing a polymer by coupling a monomer of formula VI2

$$R^{23}\text{—}U\text{—}R^{24} \quad \text{VI2}$$

with a monomer of formula XI $$R^{23}\text{-}A^c\text{-}R^{24} \quad \text{XI}$$

in an aryl-aryl coupling reaction,
wherein $R^{23}$, $R^{24}$, U, $A^c$ and $Ar^{1,2,3}$ are as defined in formula IIa, IIIa and VIa, and $R^{23}$ and $R^{24}$ are preferably selected from Cl, Br, I, —B($OZ^2$)$_2$ and —Sn($Z^4$)$_3$ as defined in formula VIa.

Preferred aryl-aryl coupling and polymerisation methods used in the processes described above and below are Yamamoto coupling, Kumada coupling, Negishi coupling, Suzuki coupling, Stille coupling, Sonogashira coupling, Heck coupling, C—H activation coupling, Ullmann coupling or Buchwald coupling. Especially preferred are Suzuki coupling, Negishi coupling, Stille coupling and Yamamoto coupling. Suzuki coupling is described for example in WO 00/53656 A1. Negishi coupling is described for example in *J. Chem. Soc., Chem. Commun.*, 1977, 683-684. Yamamoto coupling is described in for example in T. Yamamoto et al., *Prog. Polym. Sci.*, 1993, 17, 1153-1205, or WO 2004/022626 A1. Stille coupling is described for example in Z. Bao et al., *J. Am. Chem. Soc.*, 1995, 117, 12426-12435 and C—H activation is described for example in M. Leclerc et al, *Angew. Chem. Int. Ed.*, 2012, 51, 2068-2071. For example, when using Yamamoto coupling, monomers having two reactive halide groups are preferably used. When using Suzuki coupling, compounds of formula II having two reactive boronic acid or boronic acid ester groups or two reactive halide groups are preferably used. When using Stille coupling, monomers having two reactive stannane groups or two reactive halide groups are preferably used. When using Negishi coupling, monomers having two reactive organozinc groups or two reactive halide groups are preferably used. When synthesizing a linear polymer by C—H activation polymerisation, preferably a monomer as described above is used wherein at least one reactive group is an activated hydrogen bond.

Preferred catalysts, especially for Suzuki, Negishi or Stille coupling, are selected from Pd(0) complexes or Pd(II) salts. Preferred Pd(0) complexes are those bearing at least one phosphine ligand such as Pd(Ph$_3$P)$_4$. Another preferred phosphine ligand is tris(ortho-tolyl)phosphine, i.e. Pd(o-Tol$_3$P)$_4$. Preferred Pd(II) salts include palladium acetate, i.e. Pd(OAc)$_2$. Alternatively the Pd(0) complex can be prepared by mixing a Pd(0) dibenzylideneacetone complex, for example tris(dibenzyl-ideneacetone)dipalladium(0), bis(dibenzylideneacetone)palladium(0), or Pd(II) salts e.g. palladium acetate, with a phosphine ligand, for example triphenylphosphine, tris(ortho-tolyl)phosphine or tri(tert-butyl) phosphine. Suzuki polymerisation is performed in the presence of a base, for example sodium carbonate, potassium carbonate, cesium carbonate, lithium hydroxide, potassium phosphate or an organic base such as tetraethylammonium carbonate or tetraethylammonium hydroxide. Yamamoto polymerisation employs a Ni(0) complex, for example bis(1,5-cyclooctadienyl) nickel(0).

Suzuki, Stille or C—H activation coupling polymerisation may be used to prepare homopolymers as well as statistical, alternating and block random copolymers. Statistical or block copolymers can be prepared for example from the above monomers of formula VI or its subformulae, wherein one of the reactive groups is halogen and the other reactive group is a C—H activated bond, boronic acid, boronic acid derivative group or and alkylstannane. The synthesis of statistical, alternating and block copolymers is described in detail for example in WO 03/048225 A2 or WO 2005/014688 A2.

As alternatives to halogens as described above, leaving groups of formula —O—SO$_2$Z$^1$ can be used wherein Z$^1$ is as described above. Particular examples of such leaving groups are tosylate, mesylate and triflate.

Especially suitable and preferred synthesis methods of the repeating units, small molecules, monomers, oligomers and polymers of formulae I-VII and their subformulae are illustrated in the synthesis schemes shown hereinafter. Synthesis scheme examples for the preparation of the unfunctionalised monomers are shown in Schemes 1, 2, 3 and 4. Further functionalisation is shown in Scheme 5, and the synthesis of homopolymers, copolymers and statistical block co-polymers are shown in Schemes 6, 7 an 8.

Scheme 1 - Synthesis of un-functionalised monomer

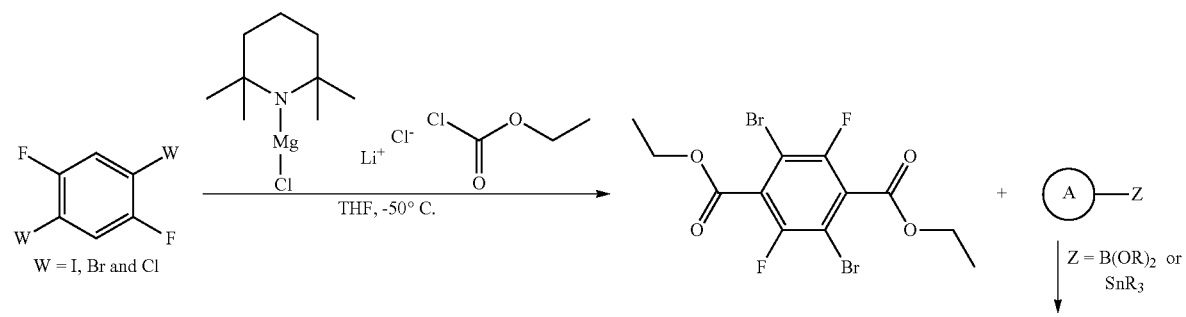

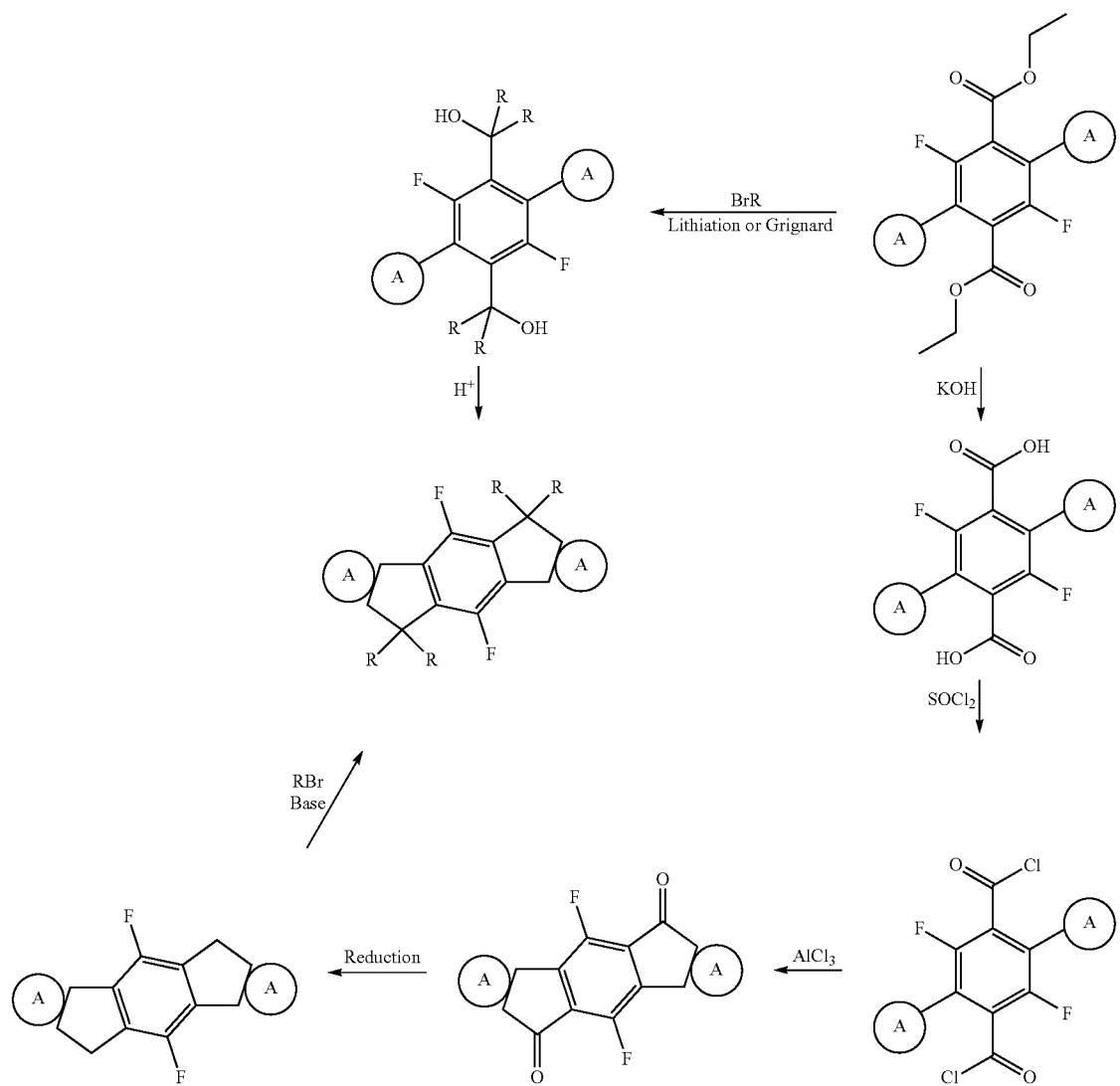
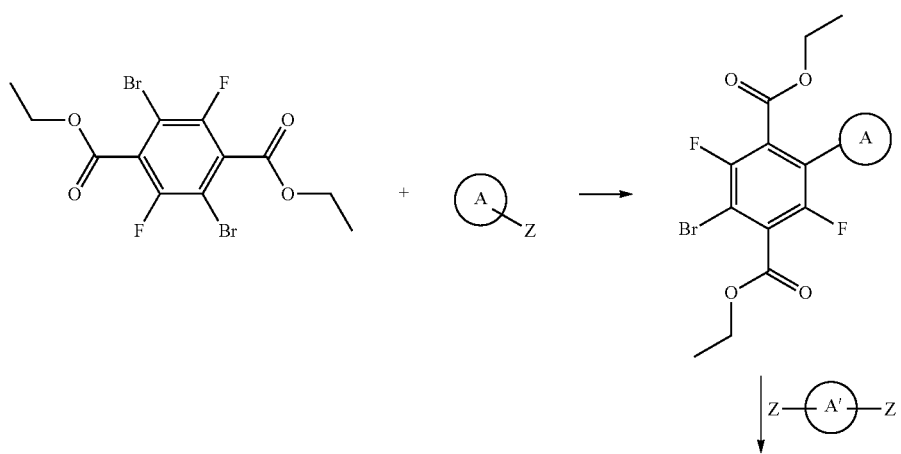
Scheme 2 - Synthesis of un-functionalised polycyclic monomer 75 76
-continued
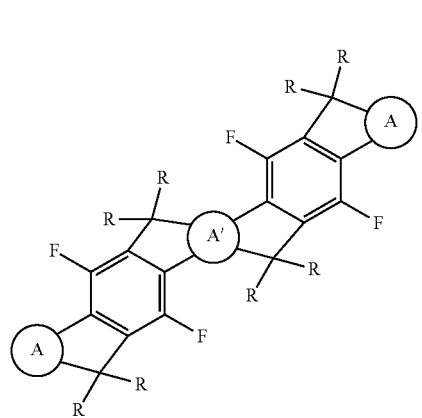
Z = B(OR)$_2$ or SnR$_3$
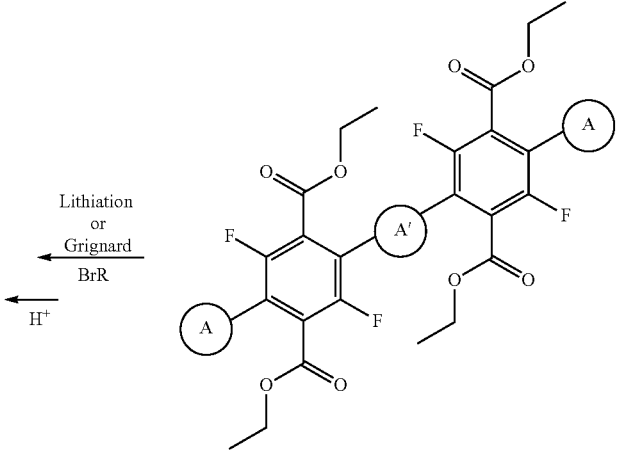
Scheme 3 - Stepwise synthesis of un-functionalised polycyclic monomer
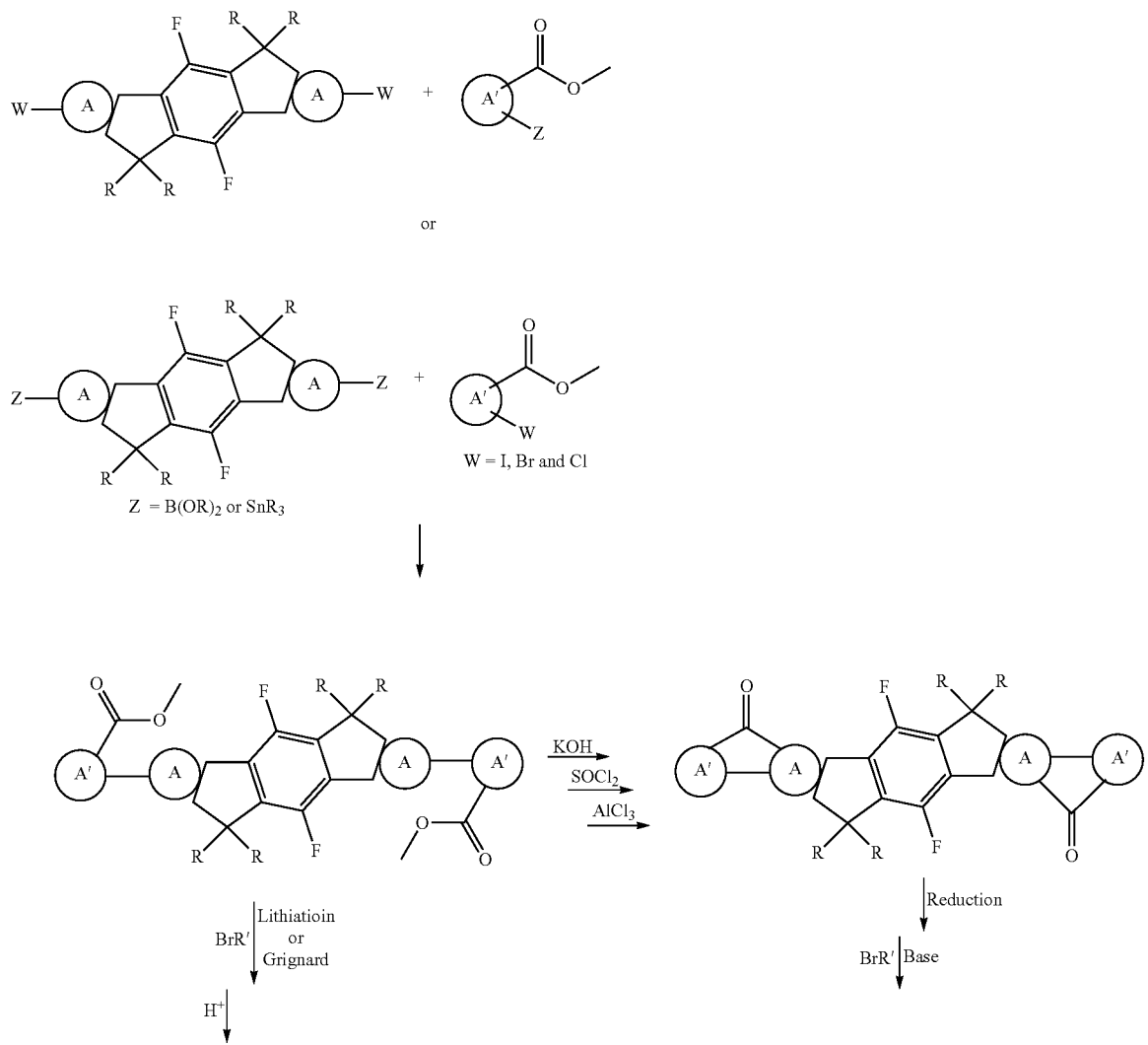

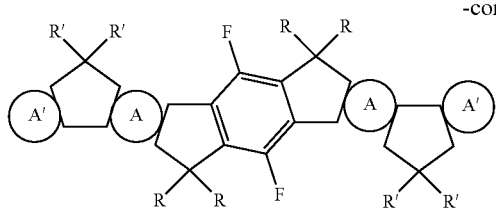
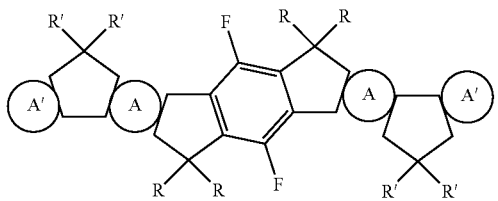
-continued
Scheme 4 - Alternative synthesis of un-functionalised polycyclic monomer
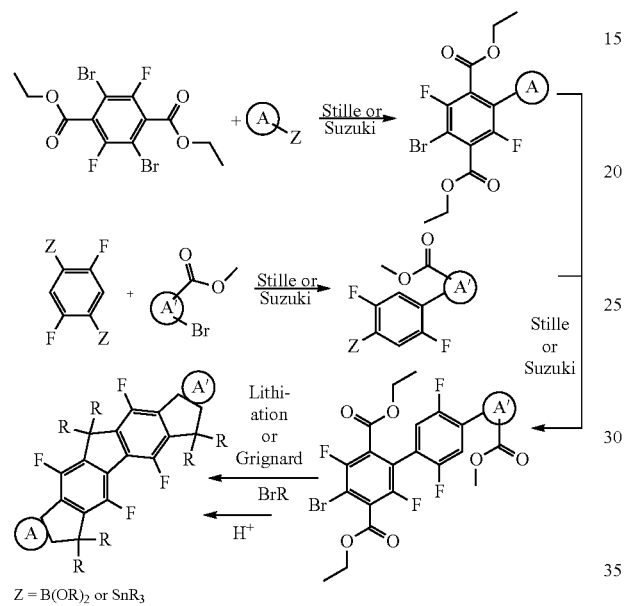
Z = B(OR)₂ or SnR₃
Scheme 5 - Synthesis of functionalised monomer
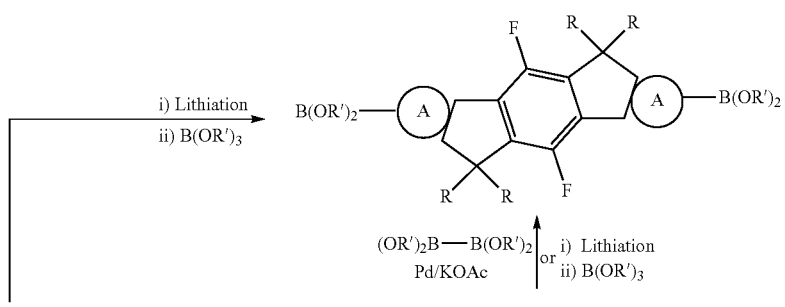
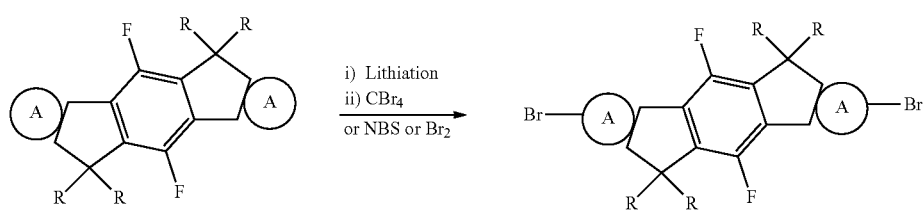

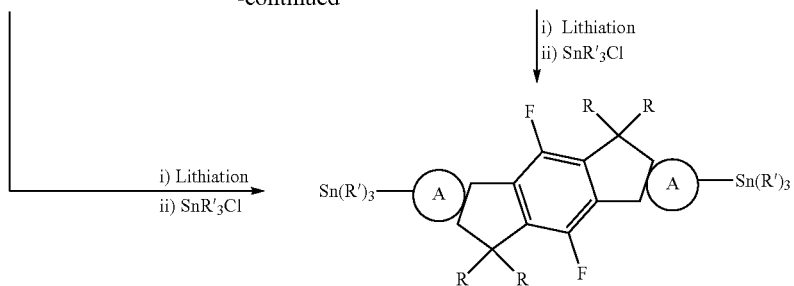

Scheme 6-Synthesis of homo-polymer

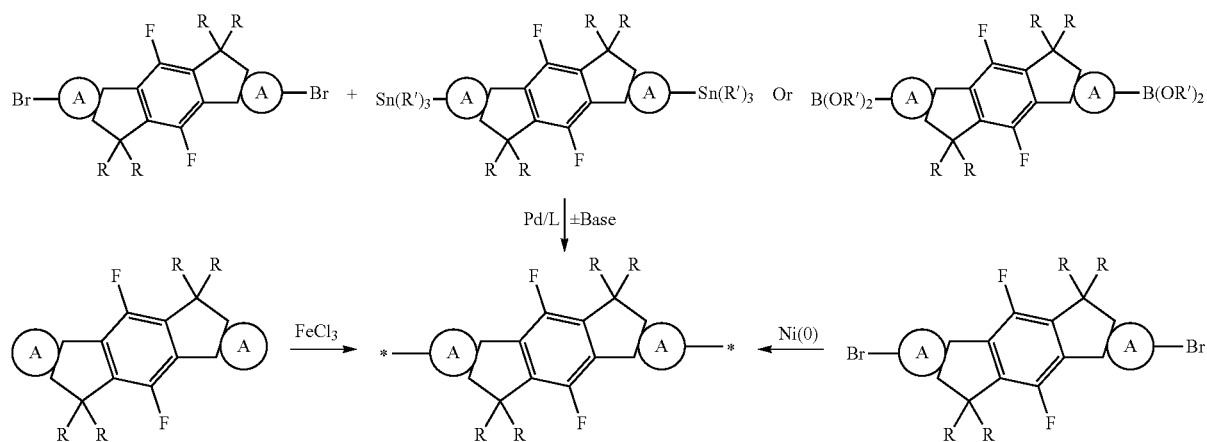

Scheme 7 - Synthesis of co-polymers

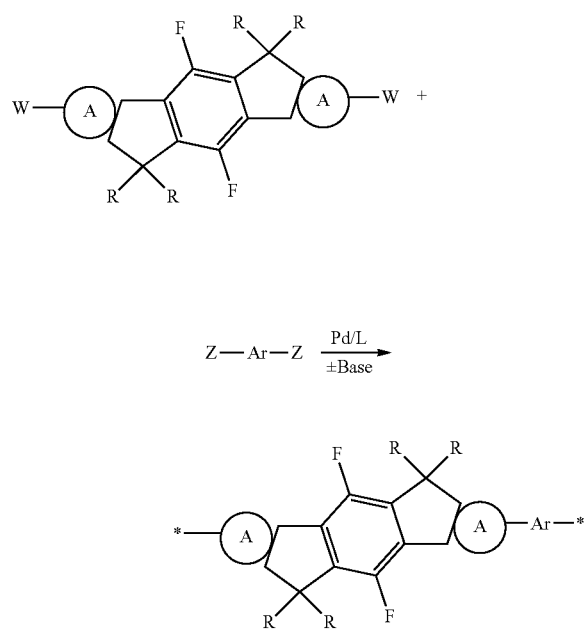

W = Br or I, Z = B(OR)₂ or SnR₃
W = B(OR)₂ or SnR₃, Z = Br or I

Scheme 8-Synthesis of statistical block co-polymers

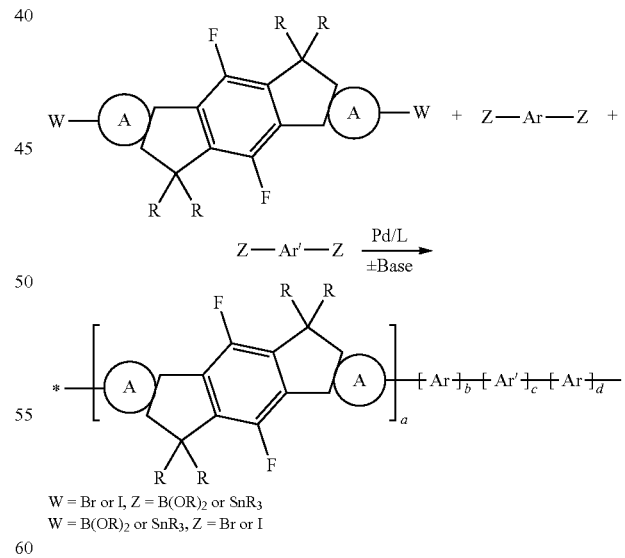

W = Br or I, Z = B(OR)₂ or SnR₃
W = B(OR)₂ or SnR₃, Z = Br or I

The novel methods of preparing monomers and polymers as described above and below are another aspect of the invention.

The compounds and polymers according to the present invention can also be used in compositions or polymer blends, for example together with monomeric or polymeric compounds having charge-transport, semiconducting, electrically conducting, photoconducting and/or light emitting semiconducting properties, or for example with compounds having hole blocking or electron blocking properties for use as interlayers or charge blocking layers in OLED devices.

Thus, another aspect of the invention relates to a composition comprising one or more small molecule compounds according to the present invention and one or more small molecule compounds and/or polymers having one or more of a charge-transport, semiconducting, electrically conducting, photoconducting, hole blocking and electron blocking property.

Another aspect of the invention relates to a composition comprising one or more polymers according to the present invention and one or more small molecule compounds and/or polymers having one or more of a charge-transport, semiconducting, electrically conducting, photoconducting, hole blocking and electron blocking property.

Another aspect of the invention relates to a polymer blend comprising one or more polymers according to the present invention and one or more further polymers having one or more of a charge-transport, semiconducting, electrically conducting, photoconducting, hole blocking and electron blocking property.

These compositions and polymer blends can be prepared by conventional methods that are described in prior art and known to the skilled person. Typically the compounds and/or polymers are mixed with each other or dissolved in suitable solvents and the solutions combined.

Another aspect of the invention relates to a formulation comprising one or more small molecules, polymers, compositions or polymer blends as described above and below and one or more organic solvents.

Preferred solvents are aliphatic hydrocarbons, chlorinated hydrocarbons, aromatic hydrocarbons, ketones, ethers and mixtures thereof. Additional solvents which can be used include 1,2,4-trimethylbenzene, 1,2,3,4-tetramethyl benzene, pentylbenzene, mesitylene, cumene, cymene, cyclohexylbenzene, diethylbenzene, tetralin, decalin, 2,6-lutidine, 2-fluoro-m-xylene, 3-fluoro-o-xylene, 2-chlorobenzotrifluoride, N,N-dimethylformamide, 2-chloro-6-fluorotoluene, 2-fluoroanisole, anisole, 2,3-dimethylpyrazine, 4-fluoroanisole, 3-fluoroanisole, 3-trifluoro-methylanisole, 2-methylanisole, phenetol, 4-methylanisole, 3-methylanisole, 4-fluoro-3-methylanisole, 2-fluorobenzonitrile, 4-fluoro-veratrol, 2,6-dimethylanisole, 3-fluorobenzo-nitrile, 2,5-dimethylanisole, 2,4-dimethylanisole, benzonitrile, 3,5-dimethyl-anisole, N,N-dimethylaniline, ethyl benzoate, 1-fluoro-3,5-dimethoxy-benzene, 1-methylnaphthalene, N-methylpyrrolidinone, 3-fluorobenzo-trifluoride, benzotrifluoride, dioxane, trifluoromethoxy-benzene, 4-fluorobenzotrifluoride, 3-fluoropyridine, toluene, 2-fluoro-toluene, 2-fluorobenzotrifluoride, 3-fluorotoluene, 4-isopropylbiphenyl, phenyl ether, pyridine, 4-fluorotoluene, 2,5-difluorotoluene, 1-chloro-2,4-difluorobenzene, 2-fluoropyridine, 3-chlorofluoro-benzene, 1-chloro-2,5-difluorobenzene, 4-chlorofluorobenzene, chloro-benzene, o-dichlorobenzene, 2-chlorofluorobenzene, p-xylene, m-xylene, o-xylene or mixture of o-, m-, and p-isomers. Solvents with relatively low polarity are generally preferred. For inkjet printing solvents and solvent mixtures with high boiling temperatures are preferred. For spin coating alkylated benzenes like xylene and toluene are preferred.

Examples of especially preferred solvents include, without limitation, dichloromethane, trichloromethane, chlorobenzene, o-dichlorobenzene, tetrahydrofuran, anisole, morpholine, toluene, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, N,N-dimethylformamide, dimethylacetamide, dimethylsulfoxide, tetraline, decaline, indane, methyl benzoate, ethyl benzoate, mesitylene and/or mixtures thereof.

The concentration of the compounds or polymers in the solution is preferably 0.1 to 10% by weight, more preferably 0.5 to 5% by weight. Optionally, the solution also comprises one or more binders to adjust the rheological properties, as described for example in WO 2005/055248 A1.

After the appropriate mixing and ageing, solutions are evaluated as one of the following categories: complete solution, borderline solution or insoluble. The contour line is drawn to outline the solubility parameter-hydrogen bonding limits dividing solubility and insolubility. 'Complete' solvents falling within the solubility area can be chosen from literature values such as published in "Crowley, J. D., Teague, G. S. Jr and Lowe, J. W. Jr., *Journal of Paint Technology*, 1966, 38 (496), 296". Solvent blends may also be used and can be identified as described in "Solvents, W. H. Ellis, Federation of Societies for Coatings Technology, p 9-10, 1986". Such a procedure may lead to a blend of 'non' solvents that will dissolve both the polymers of the present invention, although it is desirable to have at least one true solvent in a blend.

The compounds and polymers according to the present invention can also be used in patterned OSC layers in the devices as described above and below. For applications in modern microelectronics it is generally desirable to generate small structures or patterns to reduce cost (more devices/unit area), and power consumption. Patterning of thin layers comprising a polymer according to the present invention can be carried out for example by photolithography, electron beam lithography or laser patterning.

For use as thin layers in electronic or electrooptical devices the compounds, polymers, polymer blends or formulations of the present invention may be deposited by any suitable method. Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, ink jet printing, nozzle printing, letter-press printing, screen printing, gravure printing, doctor blade coating, roller printing, reverse-roller printing, offset lithography printing, dry offset lithography printing, flexographic printing, web printing, spray coating, curtain coating, brush coating, slot dye coating or pad printing.

Ink jet printing is particularly preferred when high resolution layers and devices needs to be prepared. Selected formulations of the present invention may be applied to prefabricated device substrates by ink jet printing or microdispensing. Preferably industrial piezoelectric print heads such as but not limited to those supplied by Aprion, Hitachi-Koki, InkJet Technology, On Target Technology, Picojet, Spectra, Trident, Xaar may be used to apply the organic semiconductor layer to a substrate. Additionally semi-industrial heads such as those manufactured by Brother, Epson, Konica, Seiko Instruments Toshiba TEC or single nozzle microdispensers such as those produced by Microdrop and Microfab may be used.

In order to be applied by ink jet printing or microdispensing, the compounds or polymers should be first dissolved in a suitable solvent. Solvents must fulfil the requirements stated above and must not have any detrimental effect on the chosen print head. Additionally, solvents should have boiling points>100° C., preferably >140° C. and more preferably >150° C. in order to prevent operability problems caused by the solution drying out inside the print head. Apart from the solvents mentioned above, suitable solvents include substituted and non-substituted xylene derivatives, di-$C_{1-2}$-alkyl formamide, substituted and non-substituted anisoles and other phenol-ether derivatives, substituted heterocycles such as substituted pyridines, pyrazines, pyrimidines, pyrrolidinones, substituted and non-substituted N,N-di-$C_{1-2}$-alkylanilines and other fluorinated or chlorinated aromatics.

A preferred solvent for depositing a compound or polymer according to the present invention by ink jet printing comprises a benzene derivative which has a benzene ring substituted by one or more substituents wherein the total number of carbon atoms among the one or more substituents is at least three. For example, the benzene derivative may be substituted with a propyl group or three methyl groups, in either case there being at least three carbon atoms in total. Such a solvent enables an ink jet fluid to be formed comprising the solvent with the compound or polymer, which reduces or prevents clogging of the jets and separation of the components during spraying. The solvent(s) may include those selected from the following list of examples: dodecylbenzene, 1-methyl-4-tert-butylbenzene, terpineol, limonene, isodurene, terpinolene, cymene, diethylbenzene. The solvent may be a solvent mixture, that is a combination of two or more solvents, each solvent preferably having a boiling point>100° C., more preferably >140° C. Such solvent(s) also enhance film formation in the layer deposited and reduce defects in the layer.

The ink jet fluid (that is mixture of solvent, binder and semiconducting compound) preferably has a viscosity at 20° C. of 1-100 mPa·s, more preferably 1-50 mPa·s and most preferably 1-30 mPa·s.

The polymer blends and formulations according to the present invention can additionally comprise one or more further components or additives selected for example from surface-active compounds, lubricating agents, wetting agents, dispersing agents, hydrophobing agents, adhesive agents, flow improvers, defoaming agents, deaerators, diluents which may be reactive or non-reactive, auxiliaries, colourants, dyes or pigments, sensitizers, stabilizers, nanoparticles or inhibitors.

The compounds and polymers to the present invention are useful as charge transport, semiconducting, electrically conducting, photoconducting or light emitting materials in optical, electrooptical, electronic, electroluminescent or photoluminescent components or devices. In these devices, the polymers of the present invention are typically applied as thin layers or films.

Thus, the present invention also provides the use of the semiconducting compound, polymer, polymers blend, formulation or layer in an electronic device. The formulation may be used as a high mobility semiconducting material in various devices and apparatus. The formulation may be used, for example, in the form of a semiconducting layer or film. Accordingly, in another aspect, the present invention provides a semiconducting layer for use in an electronic device, the layer comprising a compound, polymer, polymer blend or formulation according to the invention. The layer or film may be less than about 30 microns. For various electronic device applications, the thickness may be less than about 1 micron thick. The layer may be deposited, for example on a part of an electronic device, by any of the aforementioned solution coating or printing techniques.

The invention additionally provides an electronic device comprising a compound, polymer, polymer blend, formulation or organic semiconducting layer according to the present invention. Especially preferred devices are OFETs, TFTs, ICs, logic circuits, capacitors, RFID tags, OLEDs, OLETs, OPEDs, OPVs, OPDs, solar cells, laser diodes, photoconductors, photodetectors, electrophotographic devices, electrophotographic recording devices, organic memory devices, sensor devices, charge injection layers, Schottky diodes, planarising layers, antistatic films, conducting substrates and conducting patterns.

Especially preferred electronic device are OFETs, OLEDs, OPV and OPD devices, in particular bulk heterojunction (BHJ) OPV devices. In an OFET, for example, the active semiconductor channel between the drain and source may comprise the layer of the invention. As another example, in an OLED device, the charge (hole or electron) injection or transport layer may comprise the layer of the invention.

For use in OPV or OPD devices the compounds according to the present invention are preferably used in a composition that comprises or contains, more preferably consists essentially of, very preferably exclusively of, a p-type (electron donor) semiconductor and an n-type (electron acceptor) semiconductor.

The p-type semiconductor is for example constituted by a compound or polymer according to the present invention.

The n-type semiconductor can be an inorganic material such as zinc oxide ($ZnO_x$), zinc tin oxide (ZTO), titan oxide ($TiO_x$), molybdenum oxide ($MoO_x$), nickel oxide ($NiO_x$), or cadmium selenide (CdSe), or an organic material such as graphene or a fullerene or substituted fullerene, for example an indene-$C_{60}$-fullerene bisaduct like ICBA, or a (6,6)-phenyl-butyric acid methyl ester derivatized methano $C_{60}$ fullerene, also known as "PCBM-$C_{60}$" or "$C_{60}$PCBM", as disclosed for example in G. Yu, J. Gao, J. C. Hummelen, F. Wudl, A. J. Heeger, Science 1995, Vol. 270, p. 1789 ff and having the structure shown below, or structural analogous compounds with e.g. a $C_{61}$ fullerene group, a $C_{70}$ fullerene group, or a $C_{71}$ fullerene group, or an organic polymer (see for example Coakley, K. M. and McGehee, M. D. Chem. Mater. 2004, 16, 4533).

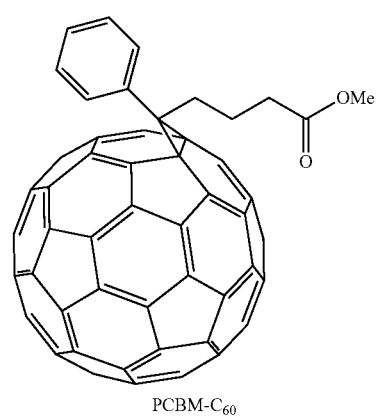

PCBM-$C_{60}$

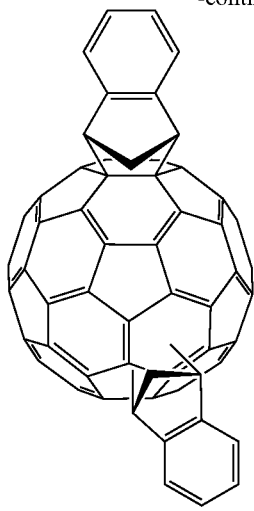

ICBA-C$_{60}$

Preferably the polymer according to the present invention is blended with an n-type semiconductor such as a fullerene or substituted fullerene, like for example PCBM-C60, PCBM-C70, bis-PCBM-C60, bis-PCBM-C70, ICMA-c60 (1',4'-dihydro-naphtho[2',3':1,2][5,6]fullerene-C60), ICBA, oQDM-C60 (1',4'-dihydro-naphtho[2',3':1,9][5,6]fullerene-C60-Ih), bis-oQDM-C60, graphene, or a metal oxide, like for example, ZnOx, TiOx, ZTO, MoOx, NiOx, or quantum dots, like for example, CdSe or CdS, to form the photoactive layer in an OPV or OPD device.

The device preferably further comprises a first transparent or semi-transparent electrode on a transparent or semi-transparent substrate on one side of the photoactive layer, and a second metallic or semi-transparent electrode on the other side of the photoactive layer.

Further preferably the OPV or OPD device comprises, between the photoactive layer and the first or second electrode, one or more additional buffer layers acting as hole transporting layer and/or electron blocking layer, which comprise a material such as metal oxide, like for example, ZTO, MoO$_x$, NiO$_x$, a conjugated polymer electrolyte, like for example PEDOT:PSS, a conjugated polymer, like for example polytriarylamine (PTAA), an organic compound, like for example N,N'-diphenyl-N,N'-bis(1-naphthyl)(1,1'-biphenyl)-4,4'diamine (NPB), N,N'-diphenyl-N,N'-(3-methylphenyl)-1,1'-biphenyl-4,4'-diamine (TPD), or alternatively as hole blocking layer and/or electron transporting layer, which comprise a material such as metal oxide, like for example, ZnO$_x$, TiO$_x$, a salt, like for example LiF, NaF, CsF, a conjugated polymer electrolyte, like for example poly[3-(6-trimethylammoniumhexyl)thiophene], poly(9,9-bis(2-ethylhexyl)-fluorene]-b-poly[3-(6-trimethylammonium-hexyl)thiophene], or poly [(9,9-bis(3'-(N,N-dimethylamino)propyl)-2,7-fluorene)-alt-2,7-(9,9-dioctylfluorene)] or an organic compound, like for example tris(8-quinolinolato)-aluminium(III) (Alq$_3$), 4,7-diphenyl-1,10-phenanthroline.

In a blend or mixture of a polymer according to the present invention with a fullerene or modified fullerene, the ratio polymer:fullerene is preferably from 5:1 to 1:5 by weight, more preferably from 1:1 to 1:3 by weight, most preferably 1:1 to 1:2 by weight. A polymeric binder may also be included, from 5 to 95% by weight. Examples of binder include polystyrene (PS), polypropylene (PP) and polymethylmethacrylate (PMMA).

To produce thin layers in BHJ OPV devices the compounds, polymers, polymer blends or formulations of the present invention may be deposited by any suitable method. Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, ink jet printing, nozzle printing, letter-press printing, screen printing, gravure printing, doctor blade coating, roller printing, reverse-roller printing, offset lithography printing, dry offset lithography printing, flexographic printing, web printing, spray coating, curtain coating, brush coating, slot dye coating or pad printing. For the fabrication of OPV devices and modules area printing method compatible with flexible substrates are preferred, for example slot dye coating, spray coating and the like.

Suitable solutions or formulations containing the blend or mixture of a polymer according to the present invention with a C$_{60}$ or C$_{70}$ fullerene or modified fullerene like PCBM must be prepared. In the preparation of formulations, suitable solvent must be selected to ensure full dissolution of both component, p-type and n-type and take into account the boundary conditions (for example rheological properties) introduced by the chosen printing method.

Organic solvent are generally used for this purpose. Typical solvents can be aromatic solvents, halogenated solvents or chlorinated solvents, including chlorinated aromatic solvents. Examples include, but are not limited to chlorobenzene, 1,2-dichlorobenzene, chloroform, 1,2-dichloroethane, dichloromethane, carbon tetrachloride, toluene, cyclohexanone, ethylacetate, tetrahydrofuran, anisole, morpholine, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, dimethylformamide, dimethylacetamide, dimethylsulfoxide, tetraline, decaline, indane, methyl benzoate, ethyl benzoate, mesitylene and combinations thereof.

The OPV device can for example be of any type known from the literature (see e.g. Waldauf et al., *Appl. Phys. Lett.*, 2006, 89, 233517).

A first preferred OPV device according to the invention comprises the following layers (in the sequence from bottom to top):
optionally a substrate,
a high work function electrode, preferably comprising a metal oxide, like for example ITO, serving as anode,
an optional conducting polymer layer or hole transport layer, preferably comprising an organic polymer or polymer blend, for example of PEDOT:PSS (poly(3,4-ethylenedioxythiophene):poly(styrene-sulfonate), or TBD (N,N'-dyphenyl-N—N'-bis(3-methylphenyl)-1,1'biphenyl-4,4'-diamine) or NBD (N,N'-dyphenyl-N—N'-bis(1-napthylphenyl)-1,1'biphenyl-4,4'-diamine),
a layer, also referred to as "photoactive layer", comprising a p-type and an n-type organic semiconductor, which can exist for example as a p-type/n-type bilayer or as distinct p-type and n-type layers, or as blend or p-type and n-type semiconductor, forming a BHJ,
optionally a layer having electron transport properties, for example comprising LiF or PFN,
a low work function electrode, preferably comprising a metal like for example aluminium, serving as cathode,
wherein at least one of the electrodes, preferably the anode, is transparent to visible light, and
wherein the p-type semiconductor is a compound or polymer according to the present invention.

A second preferred OPV device according to the invention is an inverted OPV device and comprises the following layers (in the sequence from bottom to top):
optionally a substrate,
a high work function metal or metal oxide electrode, comprising for example ITO, serving as cathode,
a layer having hole blocking properties, preferably comprising a metal oxide like $TiO_x$ or $Zn_x$, or a poly(ethyleneimine),
a photoactive layer comprising a p-type and an n-type organic semiconductor, situated between the electrodes, which can exist for example as a p-type/n-type bilayer or as distinct p-type and n-type layers, or as blend or p-type and n-type semiconductor, forming a BHJ,
an optional conducting polymer layer or hole transport layer, preferably comprising an organic polymer or polymer blend, for example of PEDOT:PSS or TBD or NBD,
an electrode comprising a high work function metal like for example silver, serving as anode,
wherein at least one of the electrodes, preferably the cathode, is transparent to visible light, and
wherein the p-type semiconductor is a compound or polymer according to the present invention.

In the OPV devices of the present invention the p-type and n-type semiconductor materials are preferably selected from the materials, like the polymer/fullerene systems, as described above When the photoactive layer is deposited on the substrate, it forms a BHJ that phase separates at nanoscale level. For discussion on nanoscale phase separation see Dennler et al, *Proceedings of the IEEE*, 2005, 93 (8), 1429 or Hoppe et al, *Adv. Func. Mater,* 2004, 14(10), 1005. An optional annealing step may be then necessary to optimize blend morpohology and consequently OPV device performance.

Another method to optimize device performance is to prepare formulations for the fabrication of OPV(BHJ) devices that may include high boiling point additives to promote phase separation in the right way. 1,8-Octanedithiol, 1,8-diiodooctane, nitrobenzene, chloronaphthalene, and other additives have been used to obtain high-efficiency solar cells. Examples are disclosed in J. Peet, et al, *Nat. Mater.,* 2007, 6, 497 or Fréchet et al. *J. Am. Chem. Soc.,* 2010, 132, 7595-7597.

Another preferred embodiment of the present invention relates to the use of a compound, composition or polymer blend according to the present invention as dye, hole transport layer, hole blocking layer, electron transport layer and/or electron blocking layer in a DSSC or a perovskite-based solar cells, and to a DSSC or perovskite-based solar cells comprising a compound composition or polymer blend according to the present invention.

DSSCs and perovskite-based DSSCs can be manufactured as described in the literature, for example in Chem. Rev. 2010, 110, 6595-6663, Angew. Chem. Int. Ed. 2014, 53, 2-15 or in WO2013171520A1

The compounds, polymers, compositions and polymer blends of the present invention can also be used as dye or pigment in other applications, for example as an ink dye, laser dye, fluorescent marker, solvent dye, food dye, contrast dye or pigment in coloring paints, inks, plastics, fabrics, cosmetics, food and other materials.

The compounds, polymers, compositions and polymer blends of the present invention are also suitable for use in the semiconducting channel of an OFET. Accordingly, the invention also provides an OFET comprising a gate electrode, an insulating (or gate insulator) layer, a source electrode, a drain electrode and an organic semiconducting channel connecting the source and drain electrodes, wherein the organic semiconducting channel comprises a compound, polymer, composition or polymer blend according to the present invention. Other features of the OFET are well known to those skilled in the art.

OFETs where an OSC material is arranged as a thin film between a gate dielectric and a drain and a source electrode, are generally known, and are described for example in U.S. Pat. Nos. 5,892,244, 5,998,804, 6,723,394 and in the references cited in the background section. Due to the advantages, like low cost production using the solubility properties of the compounds according to the invention and thus the processibility of large surfaces, preferred applications of these OFETs are such as integrated circuitry, TFT displays and security applications.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

An OFET device according to the present invention preferably comprises:
a source electrode,
a drain electrode,
a gate electrode,
a semiconducting layer,
one or more gate insulator layers,
optionally a substrate.
wherein the semiconductor layer preferably comprises a compound, polymer, composition or polymer blend as described above and below.

The OFET device can be a top gate device or a bottom gate device. Suitable structures and manufacturing methods of an OFET device are known to the skilled in the art and are described in the literature, for example in US 2007/0102696 A1.

The gate insulator layer preferably comprises a fluoropolymer, like e.g. the commercially available Cytop 809M® or Cytop 107M® (from Asahi Glass). Preferably the gate insulator layer is deposited, e.g. by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g. FC75® (available from Acros, catalogue number 12380). Other suitable fluoropolymers and fluorosolvents are known in prior art, like for example the perfluoropolymers Teflon AF® 1600 or 2400 (from DuPont) or Fluoropel® (from Cytonix) or the perfluorosolvent FC 43® (Acros, No. 12377). Especially preferred are organic dielectric materials having a low permittivity (or dielectric contant) from 1.0 to 5.0, very preferably from 1.8 to 4.0 ("low k materials"), as disclosed for example in US 2007/0102696 A1 or U.S. Pat. No. 7,095,044.

In security applications, OFETs and other devices with semiconducting materials according to the present invention, like transistors or diodes, can be used for RFID tags or security markings to authenticate and prevent counterfeiting of documents of value like banknotes, credit cards or ID cards, national ID documents, licenses or any product with monetary value, like stamps, tickets, shares, cheques etc.

Alternatively, the compounds, compositions, polymers and polymer blends (hereinafter referred to as "materials") according to the present invention can be used in OLEDs, e.g. as the active display material in a flat panel display applications, or as backlight of a flat panel display like e.g. a liquid crystal display. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The materials according to the present invention may be employed in one or more of the charge transport layers and/or in the emission layer, corresponding to their electrical and/or optical properties. Furthermore their use within the emission layer is especially advantageous, if the materials according to the present invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see, e.g., Müller et al, *Synth. Metals,* 2000, 111-112, 31-34, Alcala, *J. Appl. Phys.,* 2000, 88, 7124-7128 and the literature cited therein.

According to another use, the materials according to the present invention, especially those showing photoluminescent properties, may be employed as materials of light sources, e.g. in display devices, as described in EP 0 889 350 A1 or by C. Weder et al., *Science,* 1998, 279, 835-837.

A further aspect of the invention relates to both the oxidised and reduced form of the materials according to the present invention. Either loss or gain of electrons results in formation of a highly delocalised ionic form, which is of high conductivity. This can occur on exposure to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantantion of the dopant into the semiconductor material.

When electrons are used as carriers, suitable dopants are for example halogens (e.g., $I_2$, $Cl_2$, $Br_2$, ICl, $ICl_3$, IBr and IF), Lewis acids (e.g., $PF_5$, $AsF_5$, $SbF_5$, $BF_3$, $BCl_3$, $SbCl_5$, $BBr_3$ and $SO_3$), protonic acids, organic acids, or amino acids (e.g., HF, HCl, $HNO_3$, $H_2SO_4$, $HClO_4$, $FSO_3H$ and $ClSO_3H$), transition metal compounds (e.g., $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g., $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g., $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Ba), $O_2$, $XeOF_4$, $(NO_2^+)$ $(SbF_6^-)$, $(NO_2^+)$ $(SbCl_6^-)$, $(NO_2^+)$ $(BF_4^-)$, $AgClO_4$, $H_2IrCl_6$, $La(NO_3)_3.6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of the materials according to the present invention can be used as an organic "metal" in applications including, but not limited to, charge injection layers and ITO planarising layers in OLED applications, films for flat panel displays and touch screens, antistatic films, printed conductive substrates, patterns or tracts in electronic applications such as printed circuit boards and condensers.

The materials according to the present invention may also be suitable for use in organic plasmon-emitting diodes (OPEDs), as described for example in Koller et al., *Nat. Photonics,* 2008, 2, 684.

According to another use, the materials according to the present invention can be used alone or together with other materials in or as alignment layers in LCD or OLED devices, as described for example in US 2003/0021913. The use of charge transport compounds according to the present invention can increase the electrical conductivity of the alignment layer. When used in an LCD, this increased electrical conductivity can reduce adverse residual dc effects in the switchable LCD cell and suppress image sticking or, for example in ferroelectric LCDs, reduce the residual charge produced by the switching of the spontaneous polarisation charge of the ferroelectric LCs. When used in an OLED device comprising a light emitting material provided onto the alignment layer, this increased electrical conductivity can enhance the electroluminescence of the light emitting material.

The materials according to the present invention having mesogenic or liquid crystalline properties can form oriented anisotropic films as described above, which are especially useful as alignment layers to induce or enhance alignment in a liquid crystal medium provided onto said anisotropic film.

The materials according to the present invention may also be combined with photoisomerisable compounds and/or chromophores for use in or as photoalignment layers, as described in US 2003/0021913 A1.

According to another use, the materials according to the present invention, especially their water-soluble derivatives (for example with polar or ionic side groups) or ionically doped forms, can be employed as chemical sensors or materials for detecting and discriminating DNA sequences. Such uses are described for example in L. Chen, D. W. McBranch, H. Wang, R. Helgeson, F. Wudl and D. G. Whitten, *Proc. Natl. Acad. Sci. U.S.A.,* 1999, 96, 12287; D. Wang, X. Gong, P. S. Heeger, F. Rininsland, G. C. Bazan and A. J. Heeger, *Proc. Natl. Acad. Sci. U.S.A.,* 2002, 99, 49; N. DiCesare, M. R. Pinot, K. S. Schanze and J. R. Lakowicz, *Langmuir,* 2002, 18, 7785; D. T. McQuade, A. E. Pullen, T. M. Swager, *Chem. Rev.,* 2000, 100, 2537.

Unless the context clearly indicates otherwise, as used herein plural forms of the terms herein are to be construed as including the singular form and vice versa.

Throughout the description and claims of this specification, the words "comprise" and "contain" and variations of the words, for example "comprising" and "comprises", mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or

Example 1

2,5-Dibromo-3,6-difluoro-terephthalic acid diethyl ester

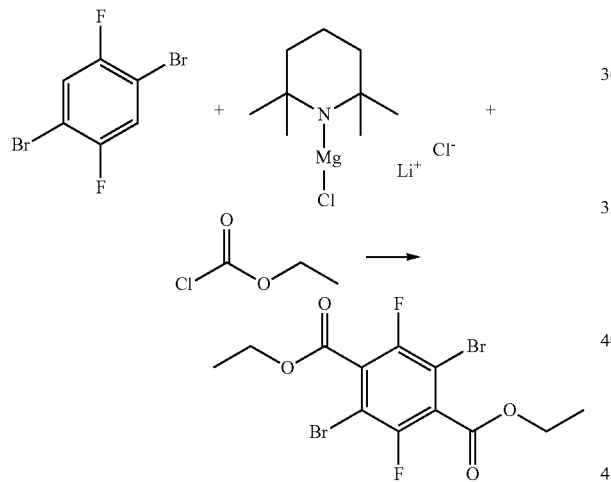

To a 1.0 M solution (tetrahydrofuran 1:1 toluene) of 2,2,6,6-tetramethylpiperidinylmagnesium chloride lithium chloride complex (200 cm³, 200 mmol) at −30° C. under inert atmosphere is added drop-wise a solution of 1,4-dibromo-2,5-difluoro-benzene (23.6 g, 86.8 mmol) in anhydrous tetrahydrofuran (150 cm³) over 30 minutes. After addition, the reaction mixture is stirred at −30° C. for 7 hours before ethyl chloroformate (22.6 g, 208 mmol) is added in one go. The mixture is then allowed to warm to 23° C. over 17 hours. Aqueous hydrochloric acid (1.0 M, 500 cm³) is added and the mixture stirred at 23° C. for 30 minutes. The product is extracted with diethyl ether (3×100 cm³). The combined organics are dried over anhydrous magnesium sulfate, filtered and the solvent removed in vacuo. The crude product is triturated with n-pentane to form a suspension. The product is filtered and washed with cold acetone, collected and dried under vacuum to give 2,5-dibromo-3,6-difluoro-terephthalic acid diethyl ester (12.0 g, 33%) as a white solid. $^{1}$H-NMR (300 MHz, CDCl$_3$) 1.42 (6H, m, CH$_3$), 4.49 (4H, q, CH$_3$) $^{19}$F-NMR 108.72 (2F, s, CF).

2,5-Difluoro-3,6-di-thiophen-2-yl-terephthalic acid diethyl ester

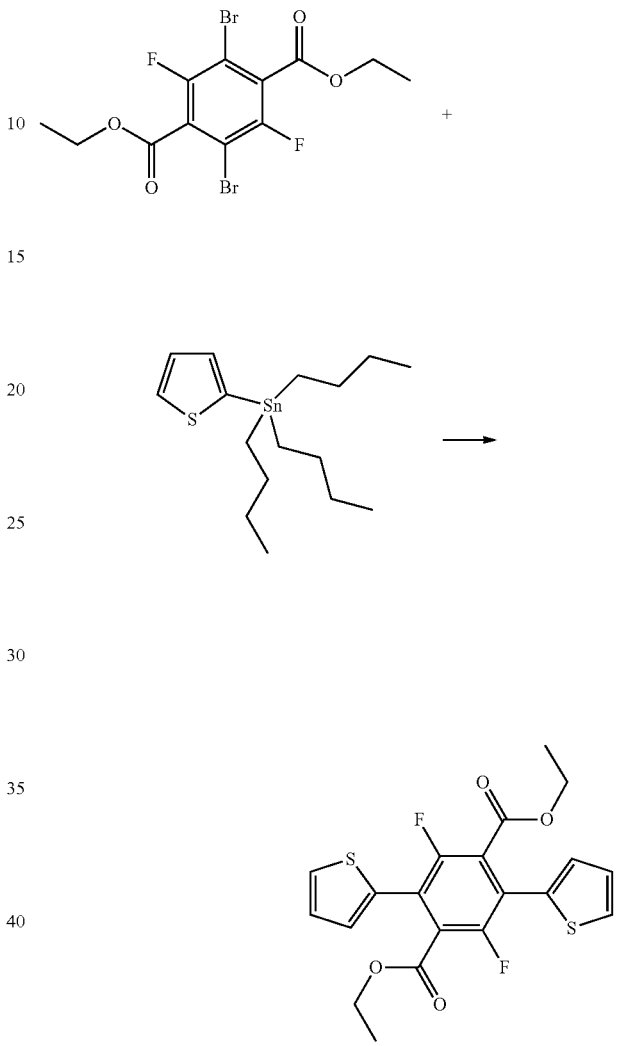

A mixture of 2,5-dibromo-3,6-difluoro-terephthalic acid diethyl ester (2.8 g, 6.7 mmol), tributyl-thiophen-2-yl-stannane (6.0 g, 16 mmol), tri-o-tolyl-phosphine (164 mg, 0.54 mmol) and anhydrous toluene (150 cm³) is degassed by nitrogen for 25 minutes. To the mixture is added tris(dibenzylideneacetone) dipalladium(0) (123 mg, 0.14 mmol) and the mixture further degassed for 15 minutes. The mixture is stirred at 100° C. for 17 hours and the solvent removed in vacuo. Dichloromethane (200 cm³) and water (200 cm³) is added and the mixture stirred at 23° C. for 30 minutes. The product is extracted with dichloromethane (3×100 cm³). The combined organics are dried over anhydrous magnesium sulfate, filtered and the solvent removed in vacuo. The crude product is triturated with light petroleum ether to form a suspension. The product is filtered, collected and dried under vacuum to give 2,5-difluoro-3,6-di-thiophen-2-yl-terephthalic acid diethyl ester (2.45 g, 86%) as a pale yellow solid. $^{1}$H-NMR (300 MHz, CDCl$_3$) 1.16 (6H, t, CH$_3$, J 7.16), 4.23 (4H, q, CH$_2$), 7.12 (2H, dd, ArH, J 5.1, 3.7), 7.21 (2H, dd, ArH, J 3.5, 0.9), 7.50 (2H, dd, ArH, J 5.1, 1.2).

4,9-Dihyro-4,4,9,9-tetrakis[4-(hexadecyl)phenyl]-s-5,10-difluoro-indaceno[1,2-b:5,6-b']ditiophene

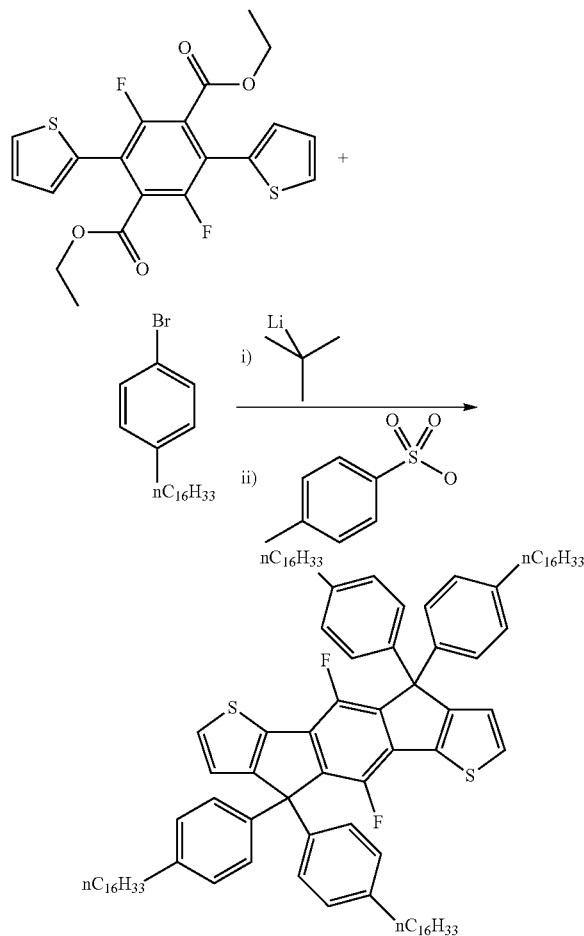

To a suspension of 1-bromo-4-hexadecylbenzene (8.4 g, 22 mmol) in anhydrous tetrahydrofuran (215 cm³) at −78° C. is added dropwise tert-butyllithium (25.9 cm³, 38.0 mmol, 1.7 M in pentane) over 45 minutes. After addition, the reaction mixture is stirred at −78° C. for 20 minutes before it is warmed to −40° C. and stirred for 40 minutes. The mixture is cooled to −78° C. and 2,5-difluoro-3,6-di-thiophen-2-yl-terephthalic acid diethyl ester (2.3 g, 5.5 mmol) added in one go. The mixture is then allowed to warm to 23° C. over 17 hours. Diethyl ether (200 cm³) and water (200 cm³) is added and the mixture stirred at 23° C. for 30 minutes. The product is extracted with diethyl ether (3×100 cm³). The combined organics are dried over anhydrous magnesium sulfate, filtered and the solvent removed in vacuo to obtain crude diol intermediate as a pale yellow oily residue. To a solution of crude diol in anhydrous dichloromethane (100 cm³) is added p-toluenesulfonic acid (1.9 g, 11 mmol). The resulting solution is stirred at 40° C. for 2 hours. The reaction mixture is allowed to cool to 23° C. and the solvent removed in vacuo. The crude is purified using silica gel column chromatography (40-60 petroleum ether). Fractions containing pure product are combined and the solvent removed in vacuo to give 4,9-dihyro-4,4,9,9-tetrakis[4-(hexadecyl)phenyl]-s-5,10-difluoro-indaceno[1,2-b:5,6-b']ditiophene (650 mg, 8%) as a cream solid. ¹H-NMR (300 MHz, CDCl₃) 0.86-0.95 (12H, m, CH₃), 1.11-1.40 (104H, m, CH₂), 1.55-1.67 (8H, m, CH₂), 2.41-2.63 (8H, m, CH₂), 6.96 (2H, d, ArH, J 4.9), 7.01-7.10 (8H, m, ArH), 7.13-7.21 (8H, m, ArH), 7.33 (2H, d, ArH, J 4.9).

2,7-Dibromo-4,9-dihyro-4,4,9,9-tetrakis[4-(hexadecyl)phenyl]-s-5,10-difluoro-indaceno[1,2-b:5,6-b']ditiophene

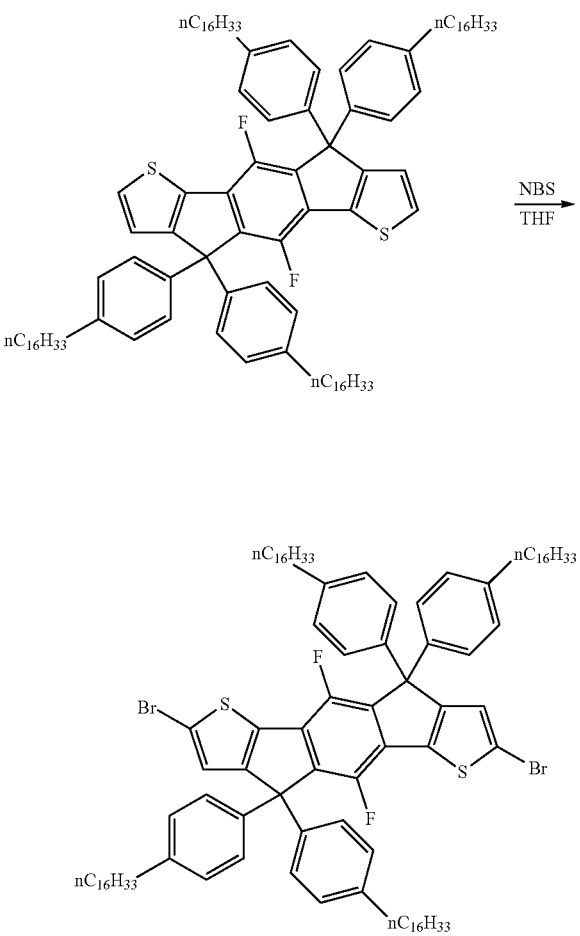

1-Bromo-pyrrolidine-2,5-dione (118 mg, 0.66 mmol) is added portion wise to a solution of 4,9-dihyro-4,4,9,9-tetrakis[4-(hexadecyl)phenyl]-s-5,10-difluoro-indaceno[1,2-b:5,6-b']ditiophene (500 mg, 0.33 mmol) in anhydrous tetrahydrofuran (50 cm³) under a nitrogen atmosphere with absence of light at 0° C. After addition, the reaction mixture is stirred at 23° C. for 17 hours and then the reaction mixture is concentrated in vacuo. The residue is dissolved in warm 40-60 petroleum ether (20 cm³ at 50° C.) and purified using silica gel column chromatography eluting with 40-60 petroleum ether. Fractions containing pure product are combined and the solvent removed in vacuo to give 2,7-dibromo-4,9-dihyro-4,4,9,9-tetrakis[4-(hexadecyl)phenyl]-s-5,10-difluoro-indaceno[1,2-b:5,6-b']ditiophene (552 mg, 82%) as a pale yellow crystalline solid. ¹H NMR (300 MHz, CDCl₃) 0.80-0.98 (12H, m, CH₃), 1.15-1.41 (104H, m, CH₂), 1.56-1.68 (8H, m, CH₂), 2.47-2.64 (8H, m, CH₂), 6.99 (2H, s, ArH), 7.03-7.21 (16H, m, ArH).

Poly{2,9-[4,9-dihyro-4,4,9,9-tetrakis[4-(hexadecyl) phenyl]-s-5,10-difluoro-indaceno[1,2-b:5,6-b']ditiophene]-alt-[2,5-thieno[3,2-b]thiophene]} (Polymer 1)

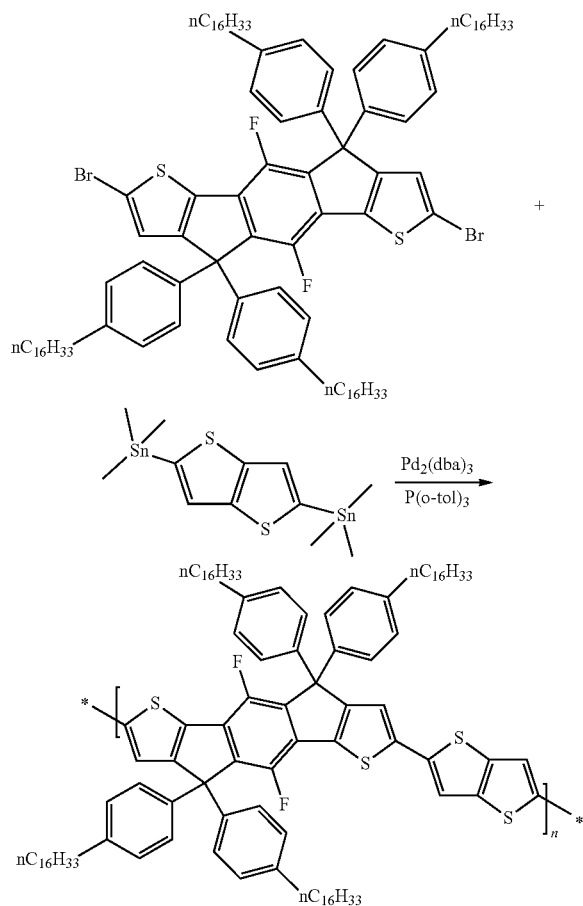

Nitrogen gas is bubbled through a mixture of 2,7-dibromo-4,9-dihydro-4,4,9,9-tetrakis[4-(hexadecyl)phenyl]-s-5,10-difluoro-indaceno[1,2-b:5,6-b']ditiophene (120 mg, 0.072 mmol), 2,5-thieno[3,2-b]thiophene (33.6 mg, 0.072 mmol), tri-o-tolyl-phosphine (1.8 mg, 0.006 mmol) and anhydrous toluene (3 cm$^3$) for 30 minutes. Tris(dibenzylideneacetone)dipalladium(0) (1.0 mg, 0.001 mmol) is added and the reaction mixture heated in a pre-heated oil bath at 100° C. for 30 minutes. Bromobenzene (0.02 cm$^3$) is added and the mixture heated at 100° C. for 30 minutes before addition of tributyl-phenyl-stannane (0.07 cm$^3$). The mixture heated at 100° C. for 1 hour. The mixture allowed to cool slightly and poured into stirred methanol (200 cm$^3$) and the polymer precipitate collected by filtration. The crude polymer is subjected to sequential soxhlet extraction; acetone, 40-60 petroleum ether and cyclohexanes. The cyclohexane extract is poured into methanol (400 cm$^3$) and the polymer precipitate collected by filtration to give poly{2,9-[4,9-dihydro-4,4,9,9-tetrakis[4-(hexadecyl)phenyl]-s-5,10-difluoro-indaceno[1,2-b:5,6-b']ditiophene]-alt-[2,5-thieno[3,2-b]thiophene]}(130 mg, 83%) as a light brown solid. GPC (chlorobenzene, 50° C.) $M_n$=74,000 g/mol, $M_w$=170,000 g/mol.

Example 2

2,5-Difluoro-3,6-bis-(5-triisopropylsilanyl-thieno[3,2-b]thiophen-2-yl)-terephthalic acid diethyl ester

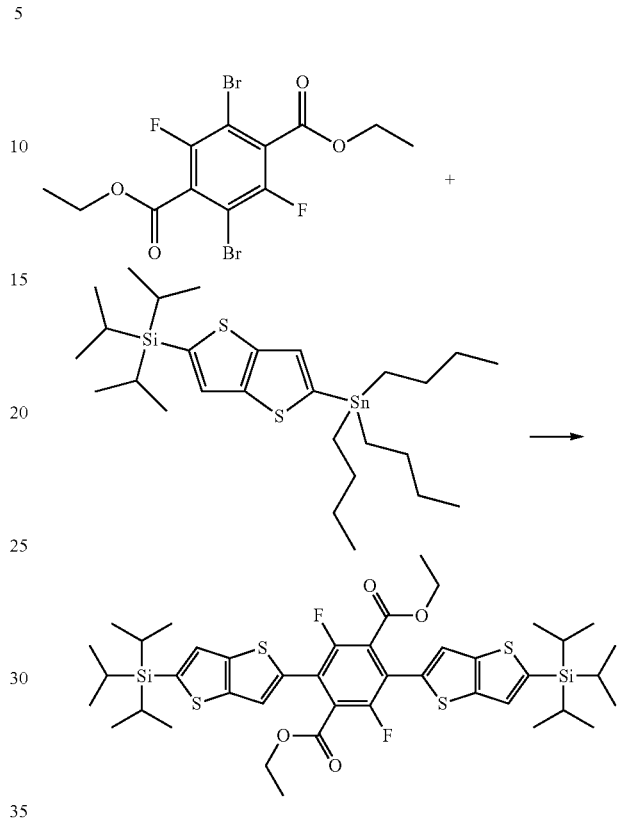

A mixture of 2,5-dibromo-3,6-difluoro-terephthalic acid diethyl ester (5.3 g, 13 mmol), triisopropyl-(5-tributylstannylthieno[3,2-b]thiophen-2-yl)silane (18.7 g, 32.0 mmol) and anhydrous toluene (150 cm$^3$) is degassed by nitrogen for 25 minutes. To the mixture is added tetrakis(triphenylphosphine)palladium(0) (500 mg, 0.4 mmol) and further degassed for 15 minutes. The mixture is stirred at 100° C. for 17 hours and the solvent removed in vacuo. Acetone (200 cm$^3$) is added and the mixture stirred at 23° C. for 30 minutes to form a suspension. The crude product is filtered, collected and dried under vacuum. The crude is purified using silica gel column chromatography (40-60 petroleum ether 6:4 dichloromethane) to give 2,5-difluoro-3,6-bis-(5-triisopropylsilanyl-thieno[3,2-b]thiophen-2-yl)-terephthalic acid diethyl ester (8.5 g, 79%) as a yellow solid. $^1$H-NMR (300 MHz, CD$_2$Cl$_2$) 1.11-1.18 (42H, m, CH$_3$), 1.28-1.50 (6H, m, CH), 4.24-4.32 (4H, q, CH$_2$), 7.40 (2H, s, ArH), 7.42 (2H, s, ArH).

Compound 1

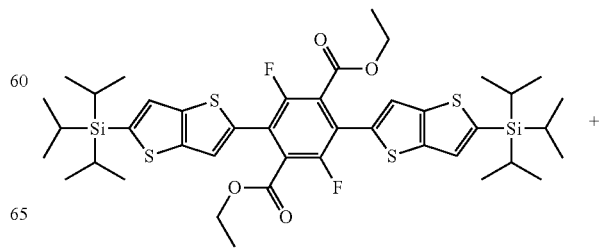

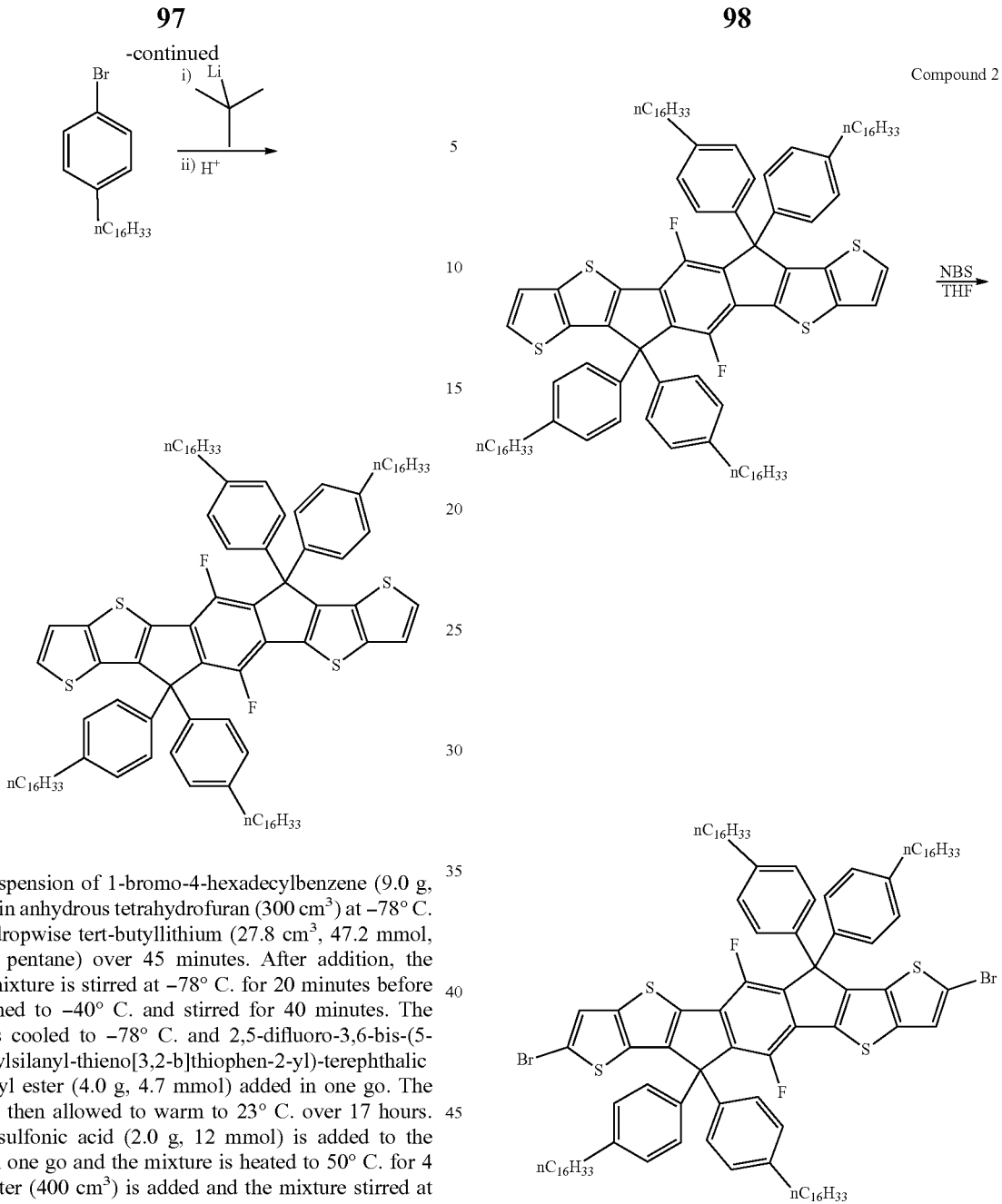

To a suspension of 1-bromo-4-hexadecylbenzene (9.0 g, 24 mmol) in anhydrous tetrahydrofuran (300 cm$^3$) at −78° C. is added dropwise tert-butyllithium (27.8 cm$^3$, 47.2 mmol, 1.7 M in pentane) over 45 minutes. After addition, the reaction mixture is stirred at −78° C. for 20 minutes before it is warmed to −40° C. and stirred for 40 minutes. The mixture is cooled to −78° C. and 2,5-difluoro-3,6-bis-(5-triisopropylsilanyl-thieno[3,2-b]thiophen-2-yl)-terephthalic acid diethyl ester (4.0 g, 4.7 mmol) added in one go. The mixture is then allowed to warm to 23° C. over 17 hours. p-Toluenesulfonic acid (2.0 g, 12 mmol) is added to the mixture in one go and the mixture is heated to 50° C. for 4 hours. Water (400 cm$^3$) is added and the mixture stirred at 23° C. for 30 minutes. The product is extracted with diethyl ether (3×100 cm$^3$). The combined organics are dried over anhydrous magnesium sulfate, filtered and the solvent removed in vacuo to obtain crude intermediate product as yellow oily residue. To a solution of intermediate product in anhydrous toluene (100 cm$^3$) is added strong acid 15H$^+$ amberlyst. The suspension was degassed for 30 minutes and the mixture is heated to 70° C. for 5 hours. The suspension is filtered and the solid washed with diethyl ether (300 cm$^3$), filtrate is collected and the solvent is removed in vacuo. The crude is purified using silica gel column chromatography (cyclohexane 8:2 chloroform at 50° C.). Fractions containing pure product are combined and the solvent removed in vacuo to give compound 1 (495 mg, 11%) as a yellow solid. $^1$H-NMR (300 MHz, CDCl$_3$) 0.83-0.94 (12H, m, CH$_3$), 1.15-1.37 (104H, m, CH$_2$), 1.54-1.68 (8H, m, CH$_2$), 2.47-2.62 (8H, m, CH$_2$), 7.04-7.13 (8H, bd, ArH), 7.17-7.24 (8H, bd, ArH), 7.30 (4H, s, ArH).

1-Bromo-pyrrolidine-2,5-dione (198 mg, 1.12 mmol) is added portion wise to a solution of compound 1 (900 mg, 0.56 mmol) in anhydrous tetrahydrofuran (50 cm$^3$) under a nitrogen atmosphere with absence of light at 0° C. After addition, the reaction mixture is stirred at 40° C. for 17 hours. The reaction mixture is concentrated in vacuo. The crude is purified using silica gel column chromatography (cyclohexane at 70° C.). Fractions containing pure product are combined and the solvent removed in vacuo. The solid is recrystallized first with chloroform and then tetrahydrofuran to give compound 2 (520 mg, 53%) as a cream yellow crystalline solid. $^1$H NMR (300 MHz, CDCl$_3$) 0.81-0.95 (12H, m, CH$_3$), 1.14-1.41 (104H, m, CH$_2$), 1.56-1.68 (8H, m, CH$_2$), 2.49-2.65 (8H, m, CH$_2$), 7.06-7.14 (8H, bd, ArH), 7.16-7.22 (8H, bd, ArH), 7.31 (2H, s, ArH).

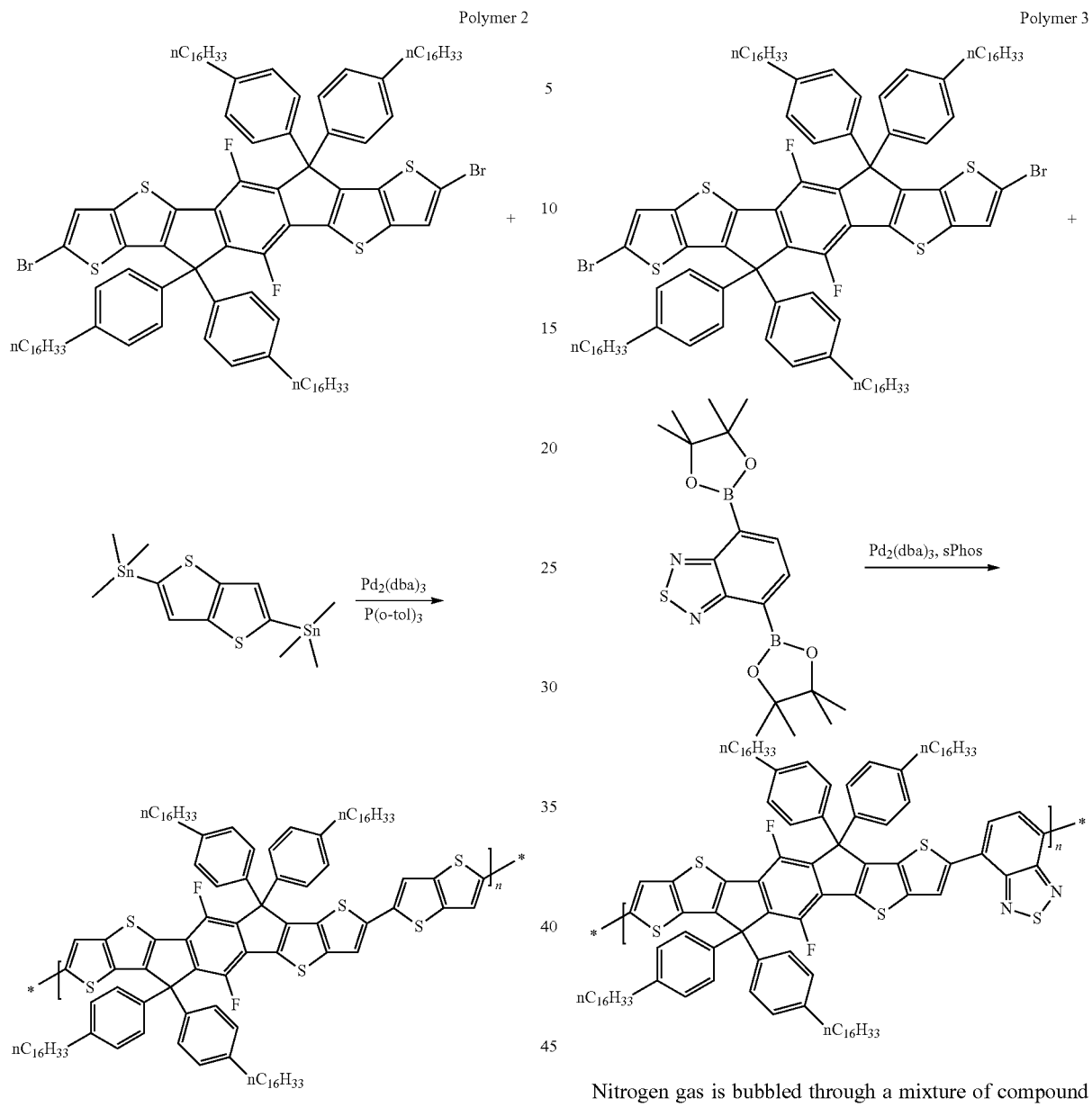

Nitrogen gas is bubbled through a mixture of compound 2 (145 mg, 0.082 mmol), 2,5-thieno[3,2-b]thiophene (38.0 mg, 0.082 mmol), tri-o-tolyl-phosphine (2.0 mg, 0.007 mmol) in anhydrous toluene (3 cm$^3$) for 30 minutes. Tris(dibenzylideneacetone)dipalladium(0) (1.2 mg, 0.002 mmol) is added and the reaction mixture is then heated in a pre-heated oil bath at 100° C. for 30 minutes. Bromobenzene (0.02 cm$^3$) is added and the mixture heated at 100° C. for 30 minutes before addition of tributyl-phenyl-stannane (0.08 cm$^3$). The mixture heated at 100° C. for 1 hour. The mixture allowed to cool slightly and poured into stirred methanol (200 cm$^3$) and the polymer precipitate collected by filtration. The crude polymer is subjected to sequential soxhlet extraction; acetone, 40-60 petroleum ether and cyclohexanes. The cyclohexane extract is poured into methanol (400 cm$^3$) and the polymer precipitate collected by filtration to give polymer 2 (120 mg, 71%) as a brown red solid. GPC (chlorobenzene, 50° C.) $M_n$=39,000 g/mol, $M_w$=75,000 g/mol.

Nitrogen gas is bubbled through a mixture of compound 2 (139 mg, 0.078 mmol), 4,7-bis-(4,4,5,5-tetramethyl-[1,3,2]dioxaborolan-2-yl)-benzo[1,2,5]thiadiazole (30.4 mg, 0.078 mmol), aliquat 336 (0.1 mg), 2-dicyclohexylphosphino-2',6'-dimethoxybiphenyl (2.6 mg, 0.006 mmol) and a solution of sodium carbonate (2M aq 0.2 cm$^3$) in toluene (2.3 cm$^3$) for 30 minutes. Tris(dibenzylideneacetone)dipalladium(0) (1.1 mg, 0.002 mmol) is added and the reaction mixture is then heated in a pre-heated oil bath at 100° C. for 30 minutes. Bromobenzene (0.02 cm$^3$) is added and the mixture heated at 100° C. for 30 minutes before addition of phenylboronic acid (19.0 mg). The mixture heated at 100° C. for 1 hour. The mixture allowed to cool slightly and poured into stirred methanol (200 cm$^3$) and the polymer precipitate collected by filtration. The crude polymer is subjected to sequential soxhlet extraction; acetone, 40-60 petroleum ether, cyclohexanes and chloroform. The chloroform extract is poured into methanol (400 cm$^3$) and the polymer precipitate collected by filtration to give polymer 2 (97 mg, 65%) as a dark blue solid. GPC (chlorobenzene, 50° C.) $M_n$=52,000 g/mol, $M_w$=88,000 g/mol.

Example 3

Transistor Fabrication and Measurement

Top-gate thin-film organic field-effect transistors (OFETs) were fabricated on glass substrates with photolithographically defined Au source-drain electrodes. A 7 mg/cm$^3$ solution of the organic semiconductor in dichlorobenzene was spin-coated on top (an optional annealing of the film is carried out at 100° C., 150° C. or 200° C. for between 1 and 5 minutes) followed by a spin-coated fluoropolymer dielectric material (Lisicon® D139 from Merck, Germany). Finally a photolithographically defined Au gate electrode was deposited. The electrical characterization of the transistor devices was carried out in ambient air atmosphere using computer controlled Agilent 4155C Semiconductor Parameter Analyser. Charge carrier mobility in the saturation regime (μsat) was calculated for the compound. Field-effect mobility was calculated in the saturation regime ($V_d$>($V_g$−$V_0$)) using equation (1):

$$\left(\frac{dI_d^{sat}}{dV_g}\right)_{V_d} = \frac{WC_i}{L}\mu^{sat}(V_g - V_0) \quad (1)$$

where W is the channel width, L the channel length, $C_i$ the capacitance of insulating layer, $V_g$ the gate voltage, $V_0$ the turn-on voltage, and $\mu_{sat}$ is the charge carrier mobility in the saturation regime. Turn-on voltage ($V_0$) was determined as the onset of source-drain current.

The mobilities ($\mu_{sat}$) for polymers 1 and 2 in top-gate OFETs are summarised in Table 1.

TABLE 1

Mobilities ($\mu_{sat}$) for polymers 1 and 2 in top-gate OFETs.

| Polymer | $\mu_{sat}$ (cm$^2$/Vs) |
|---|---|
| 1 | 0.149 |
| 2 | 0.387 |

The Drawing shows the transfer characteristics and the charge carrier mobility of a top-gate OFET prepared as described above, wherein polymer 2 is used as the organic semiconductor.

The invention claimed is:

1. A compound comprising one or more divalent units of formula I

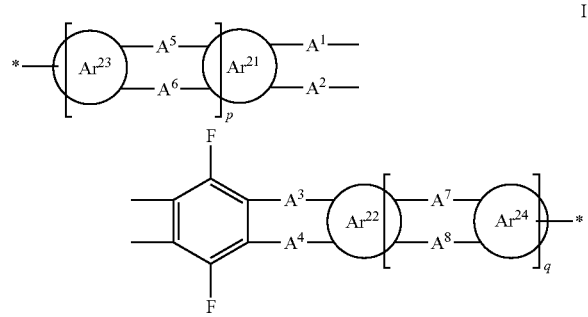

I wherein
one of A$^1$ and A$^2$ is X and the other is a single bond,
one of A$^3$ and A$^4$ is X and the other is a single bond,
one of A$^5$ and A$^6$ is X and the other is a single bond,
one of A$^7$ and A$^8$ is X and the other is a single bond,
X is, on each occurrence identically or differently, CR$^1$R$^2$, C=CR$^1$R$^2$, SiR$^1$R$^2$, GeR$^1$R$^2$, C=O or NR$^1$,
R$^1$, R$^2$ denote, independently of each other and on each occurrence identically or differently, H, halogen or straight chain, branched or cyclic alkyl group with 1 to 50 C atoms in which one or more non-adjacent CH$_2$ groups are optionally replaced, in each case independently from one another, by —O—, —S—, —C(O)—, —C(O)O—, —O—C(O)—, —O—CO(O)—O—, —SO$_2$—, —SO$_3$—, —NR$^0$—, —SiR$^0$R$^{00}$—, —CF$_2$—, —CR$^0$=CR$^{00}$—, —CY$^1$=CY$^2$— or —C≡C— in such a manner that O and/or S atoms are not linked directly to one another, and in which one or more, but not all, H atoms are optionally replaced by F, Cl, Br, I or CN, or denotes monocyclic or polycyclic aryl or heteroaryl, each of which is optionally substituted with one or more groups R$^S$ and has 4 to 30 ring atoms,
p, q are independently of each other 0, 1 or 2,
Ar$^{21}$, Ar$^{22}$, Ar$^{23}$, Ar$^{24}$ denote, independently of each other, and on each occurrence identically or differently, an aromatic or heteroaromatic group, each of which is monocyclic or polycyclic, has 4 to 20 ring atoms, and is optionally substituted by one or more groups R$^S$,
R$^S$ denotes, on each occurrence identically or differently, F, Br, Cl, —CN, —NC, —NCO, —NCS, —OCN, —SCN, —C(O)NR$^0$R$^{00}$, —C(O)X$^0$, —C(O)R$^0$, —C(O)OR$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, optionally substituted silyl, carbyl or hydrocarbyl with 1 to 40 C atoms that is optionally substituted and optionally comprises one or more hetero atoms,
R$^0$, R$^{00}$ independently of each other denote H or optionally substituted C$_{1-40}$ carbyl or hydrocarbyl,
Y$^1$, Y$^2$ independently of each other denote H, F, Cl or CN,
X$^0$ denotes halogen.

2. The compound according to claim 1, wherein Ar$^{21}$, Ar$^{22}$, Ar$^{23}$ and Ar$^{24}$ in formula I, when representing a non-terminal ring, are selected from the following formulae

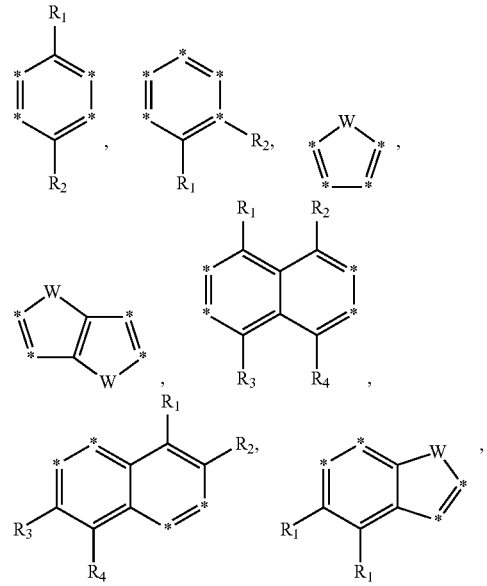

-continued

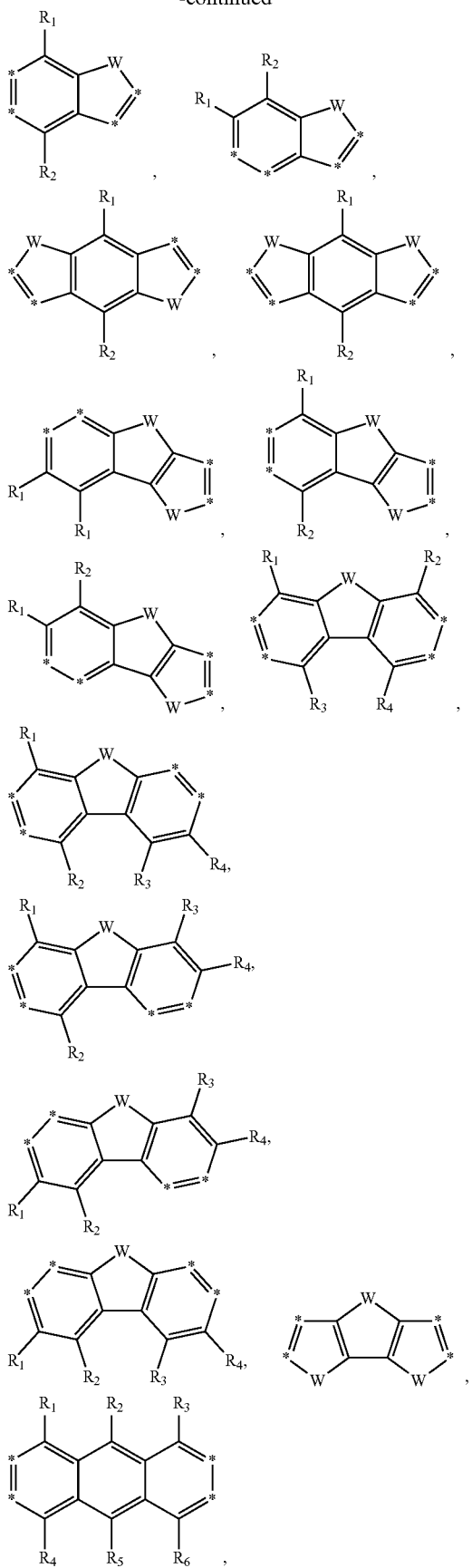

-continued

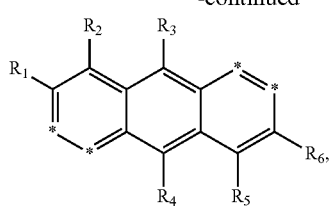

wherein

W is on each occurrence identically or differently S, O or Se, $R^1$ and $R^2$ have independently of each other one of the meanings given in claim 1, and $R^3$, $R^4$, $R^5$ and $R^6$ have independently of each other one of the meanings given for $R^1$.

3. The compound according to claim 1, wherein $Ar^{21}$, $Ar^{22}$, $Ar^{23}$ and $Ar^{24}$ in formula I, when representing a terminal ring, are selected from the following formulae

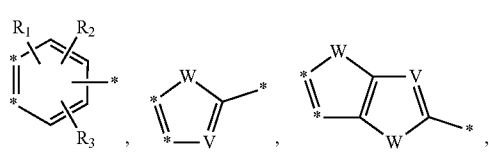

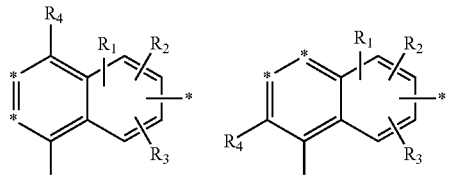

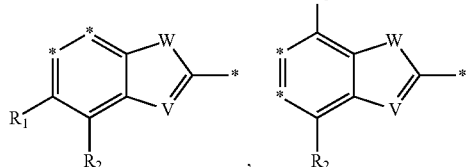

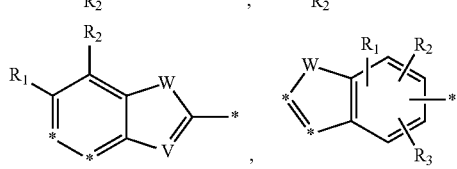

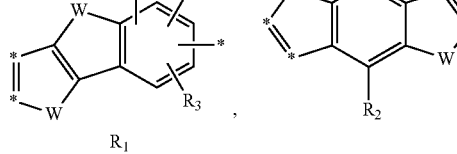

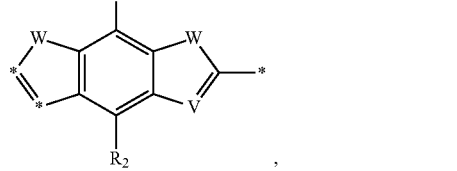

-continued

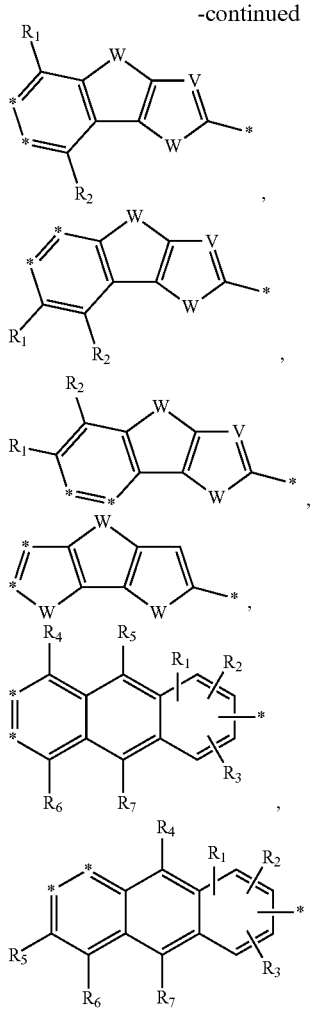

wherein
W is on each occurrence identically or differently S, O or Se,
V is on each occurrence identically or differently CR¹ or N,
R¹ and R² have independently of each other one of the meanings given in claim 1, and
R³, R⁴, R⁵, R⁶ and R⁷ have independently of each other one of the meanings given for R¹.

4. The compound according to claim 1, wherein A¹, A⁴, A⁶ and A⁷ are each a single bond.

5. The compound according claim 1, characterized in that it is a conjugated polymer comprising one or more units of formula I as defined in claim 1.

6. The compound according to claim 5, characterized in that it comprises one or more units of formula IIa or IIb

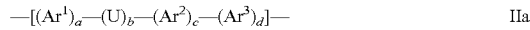    IIa

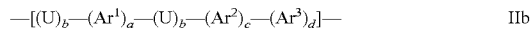    IIb wherein
U is a unit of formula I as defined in claim 1,
Ar¹, Ar², Ar³ are, on each occurrence identically or differently, and independently of each other, aryl or heteroaryl that is different from U, and is optionally substituted,
R⁰ and R⁰⁰ are independently of each other H or optionally substituted $C_{1-40}$ carbyl or hydrocarbyl, X⁰ is halogen,
a, b, c are on each occurrence identically or differently 0, 1 or 2,
d is on each occurrence identically or differently 0 or an integer from 1 to 10,
wherein the polymer comprises at least one repeating unit of formula IIa or IIb wherein b is at least 1.

7. The compound according to claim 6, characterized in that it additionally comprises one or more repeating units selected of formula IIIa or IIIb

    IIIa

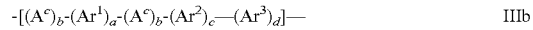    IIIb wherein Ar¹, Ar², Ar³, a, b, c and d are as defined in claim 6, and $A^c$ is an aryl or heteroaryl group that is different from U and $Ar^{1-3}$, has 5 to 30 ring atoms, is optionally substituted by one or more groups $R^S$, and is selected from aryl or heteroaryl groups having electron acceptor properties, wherein the polymer comprises at least one repeating unit of formula IIIa or IIIb wherein b is at least 1,
wherein $R^S$ is on each occurrence identically or differently F, Br, Cl, —CN, —NC, —NCO, —NCS, —OCN, —SCN, —C(O)NR⁰R⁰⁰, —C(O)X⁰, —C(O)R⁰, —NH₂, —NR⁰R⁰⁰, —SH, —SR⁰, —SO₃H, —SO₂R⁰, —OH, —NO₂, —CF₃, —SF₅, optionally substituted silyl, carbyl or hydrocarbyl with 1 to 40 C atoms that is optionally substituted and optionally comprises one or more hetero atoms.

8. The compound according claim 7, characterized in that it is selected of formula IV:

    IV wherein
A, B, C independently of each other denote a distinct unit of formula I, IIa, IIb, IIIa or IIIb, provided that at least one of A, B and C is a unit of the formula I, IIa or IIb,
x is >0 and ≤1,
y is ≥0 and <1,
z is ≥0 and <1,
x+y+z is 1, and
n is an integer >1.

9. The compound according to claim 8, characterized in that it is selected of formula V

    V wherein "chain" denotes a polymer chain of formulae IV, and R²¹ and R²² have independently of each other one of the meanings of $R^S$, or denote, independently of each other, H, F, Br, Cl, I, —CH₂Cl, —CHO, —CR'=CR''₂, —SiR'R''R''', —SiR'X'X'', —SiR'R''X', —SnR'R''R''', —BR'R'', —B(OR')(OR''), —B(OH)₂, —O—SO₂—R', —C≡CH, —C≡C—SiR'₃, —ZnX' or an endcap group, X' and X'' denote halogen, R', R'' and R''' have independently of each other one of the meanings of R⁰, and two of R', R'' and R''' may also form a cyclosilyl, cyclostannyl, cycloborane or cycloboronate group with 2 to 20 C atoms together with the respective hetero atom to which they are attached.

10. The compound of claim 6, wherein:
Ar¹, Ar², Ar³ are, on each occurrence identically or differently, and independently of each other, aryl or heteroaryl that is different from U, has 5 to 30 ring atoms and is optionally substituted by one or more groups $R^S$, $R^S$ is on each occurrence identically or differently F, Br, Cl, —CN, —NC, —NCO, —NCS, —OCN, —SCN, —C(O)NR°R°°, —C(O)X°, —C(O)R°, —NH$_2$, —NR°R°°, —SH, —SR°, —SO$_3$H, —SO$_2$R°, —OH, —NO$_2$, —CF$_3$, —SF$_5$, optionally substituted silyl, carbyl or hydrocarbyl with 1 to 40 C atoms that is optionally substituted and optionally comprises one or more hetero atoms, and X° is F, Cl or Br.

11. The compound according to claim 1, characterized in that it is selected from the following formulae

*—[(Ar$^1$—U—Ar$^2$)$_x$—(Ar$^3$)$_y$]$_n$—*  IVa

*—[(Ar$^1$—U—Ar$^2$)$_x$—(Ar$^3$—Ar$^3$)$_y$]$_n$—*  IVb

*—[(Ar$^1$—U—Ar$^2$)$_x$—(Ar$^3$—Ar$^3$—Ar$^3$)$_y$]$_n$—*  IVc

*—[(Ar$^1$)$_a$—(U)$_b$—(Ar$^2$)$_c$—(Ar$^3$)$_d$]$_n$—*  IVd

*—([(Ar$^1$)$_a$—(U)$_b$—(Ar$^2$)$_c$—(Ar$^3$)$_d$]$_x$—[(Ar$^1$)$_a$-(A$^c$)$_b$-(Ar$^2$)$_c$—(Ar$^3$)$_d$]$_y$)$_n$—*  IVe

*—[(U—Ar$^1$—U)$_x$—(Ar$^2$—Ar$^3$)$_y$]$_n$—*  IVf

*—[(U—Ar$^1$—U)$_x$—(Ar$^2$—Ar$^3$—Ar$^3$)$_y$]$_n$—*  IVg

*—[(U)$_b$—(Ar$^1$)$_a$—(U)$_b$—(Ar$^2$)$_c$]$_n$—*  IVh

*—([(U)$_b$—(Ar$^1$)$_a$—(U)$_b$—(Ar$^2$)$_c$]$_x$—[(A$^c$)$_b$-(Ar$^1$)$_a$-(A$^c$)$_b$-(Ar$^2$)$_d$]$_y$)$_n$—*  IVi

*—[(U—Ar$^1$)$_x$—(U—Ar$^2$)$_y$—(U—Ar$^3$)$_z$]$_n$—*  IVk

*—[U]$_n$—*  IVm wherein U is a unit of the formula I,

Ar$^1$, Ar$^2$, Ar$^3$ are, on each occurrence identically or differently, and independently of each other, aryl or heteroaryl that is different from U, and is optionally substituted, a, b, c are on each occurrence identically or differently 0, 1 or 2, d is on each occurrence identically or differently 0 or an integer from 1 to 10, A$^c$ is an aryl or heteroaryl group that is different from U and Ar$^{1-3}$, has 5 to 30 ring atoms, is optionally substituted by one or more groups, and is selected from aryl or heteroaryl groups having electron acceptor properties, wherein $R^S$ is on each occurrence identically or differently F, Br, Cl, —CN, —NC, —NCO, —NCS, —OCN, —SCN, —C(O)NR°R°°, —C(O)X°, —C(O)R°, —NH$_2$, —NR°R°°, —SH, —SR°, —SO$_3$H, —SO$_2$R°, —OH, —NO$_2$, —CF$_3$, —SF$_5$, optionally substituted silyl, carbyl or hydrocarbyl with 1 to 40 C atoms that is optionally substituted and optionally comprises one or more hetero atoms, x is >0 and ≤1,
y is ≥0 and <1,
z is ≥0 and <1,
x+y+z is 1, and
n is an integer >1, wherein these polymers can be alternating or random copolymers, and wherein in formula IVd and IVe in at least one of the repeating units [(Ar$^1$)$_a$—(U)$_b$—(Ar$^2$)$_c$—(Ar$^3$)$_d$] and in at least one of the repeating units [(Ar$^1$)$_a$-(A$^c$)$_b$-(Ar$^2$)$_c$—(Ar$^3$)$_d$] b is at least 1 and wherein in formula IVh and IVi in at least one of the repeating units [(U)$_b$—(Ar$^1$)$_a$—(U)$_b$—(Ar$^2$)$_d$] and in at least one of the repeating units [(U)$_b$—(Ar$^1$)$_a$—(U)$_b$—(Ar$^2$)$_d$] b is at least 1.

12. The compound according to claim 1, characterized in that it is selected from the following formulae

*—[U]$_n$—*  IV1

*—[(Ar$^1$)$_a$—U—(Ar$^2$)$_c$—(Ar$^3$)$_d$]$_n$—*  IV2

*—[[(Ar$^1$)$_a$—U]$_x$—[(Ar$^2$)$_c$—(Ar$^3$)$_d$]$_y$]$_n$—*  IV3

*—[[(Ar$^1$)$_a$]$_x$—[U]$_y$—[(Ar$^2$)$_c$]$_z$—[(Ar$^3$)$_d$]$_w$]$_n$—*  IV4

*—[(Ar$^1$)$_a$—U]$_n$—*  IV5

*—[(Ar$^1$)$_a$—U]$_o$—[(Ar$^1$)$_a$—U]$_n$—*  IV6

*—[(Ar$^1$)$_a$—U]$_o$—[(Ar$^2$)$_c$—(Ar$^3$)$_d$]$_n$—*  IV7

*—[(Ar$^1$)$_a$]$_o$—[U]$_p$—[(Ar$^2$)$_c$]$_n$—[(Ar$^3$)$_d$]$_q$—*  IV8 wherein U is unit of formula I,

Ar$^1$, Ar$^2$, Ar$^3$ are, on each occurrence identically or differently, and independently of each other, aryl or heteroaryl that is different from U, and is optionally substituted, a, b, c are on each occurrence identically or differently 0, 1 or 2, d is on each occurrence identically or differently 0 or an integer from 1 to 10, x is >0 and ≤1,
y is ≥0 and <1,
z is ≥0 and <1,
x+y+z is 1,
n is an integer >1,
w is ≥0 and <1, and o, p and q have one of the meanings given for n.

13. The compound according to claim 1, characterized in that it is a small molecule or oligomer of formula VII

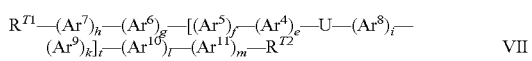

VII wherein

U is a unit of formula I,

Ar$^{4-11}$ independently of each other denote —CY$^1$=CY$^2$—, —C≡C—, or aryl or heteroaryl that has 5 to 30 ring atoms and is unsubstituted or substituted by one or more groups $R^S$, and one or more of Ar$^{4-11}$ may also denote U which is a unit of the formula I, $R^S$ is on each occurrence identically or differently F, Br, Cl, —CN, —NC, —NCO, —NCS, —OCN, —SCN, —C(O)NR°R°°, —C(O)X°, —C(O)R°, —NH$_2$, —NR°R°°, —SH, —SR°, —SO$_3$H, —SO$_2$R°, —OH, —NO$_2$, —CF$_3$, —SF$_5$, optionally substituted silyl, carbyl or hydrocarbyl with 1 to 40 C atoms that is optionally substituted and optionally comprises one or more hetero atoms, Y$^1$, Y$^2$ independently of each other denote H, F, Cl or CN, R$^{T1,T2}$ independently of each other denote H, F, Cl, Br, —CN, —CF$_3$, R, —CF$_2$—R, —O—R, —S—R, —SO$_2$—R, —SO$_3$—R, —C(O)—R, —C(O)—H, —C(S)—R, —C(O)—CF$_2$—R, —C(O)—OR, —C(S)—OR, —O—C(O)—R, —O—C(S)—R, —C(O)—SR, —S—C(O)—R, —C(O)NRR', —NR'—C(O)—R, —NHR, —NRR', —SO$_2$—R, —CR'=CR"R'", —C≡C—R', —≡C—SiR'R"R'", —CH═CH(CN), —CH═C(CN)$_2$, —C(CN)═C(CN)$_2$, —CH═C(CN)(Ar$^{12}$), —CH═C(CN)—COOR, —CH═C(COOR)$_2$, CH═C(CONRR')$_2$,
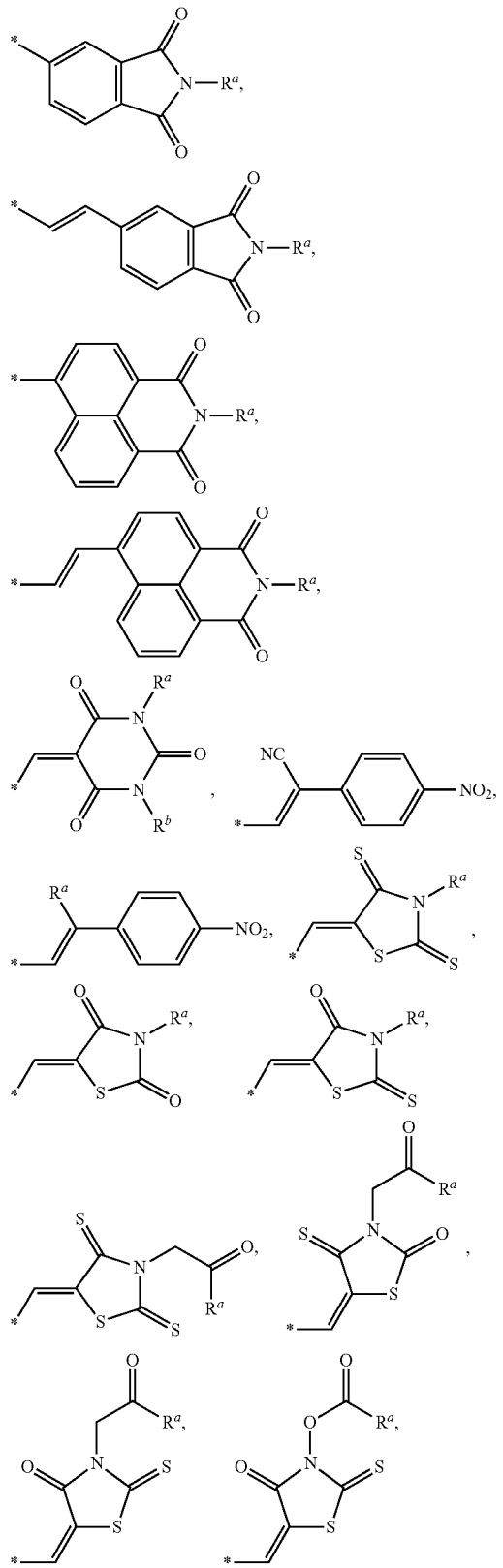
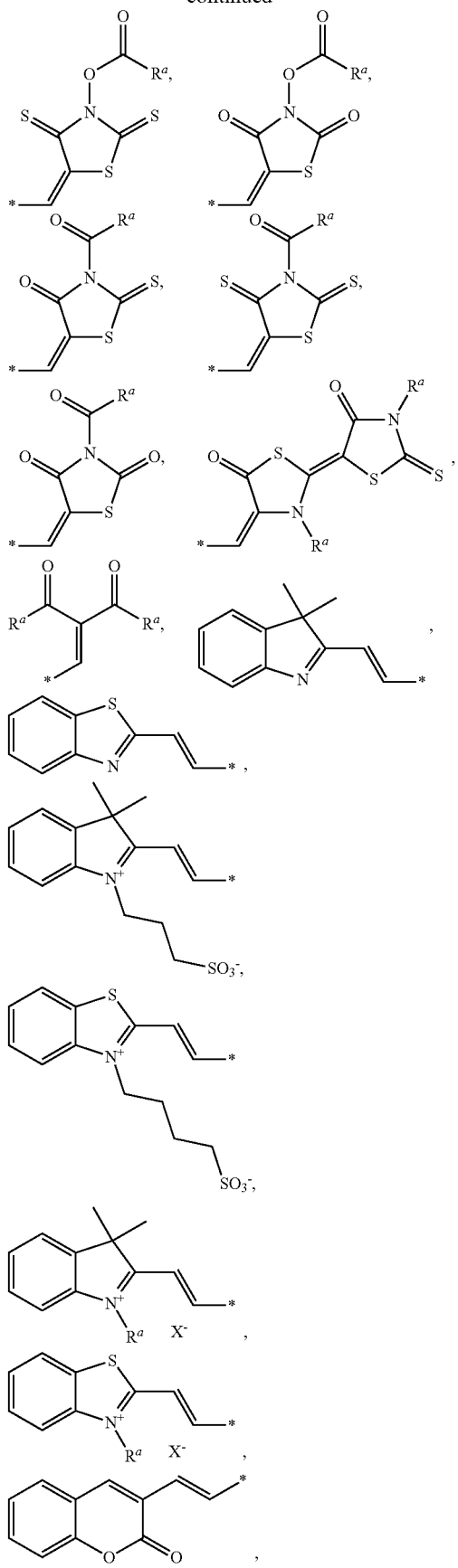

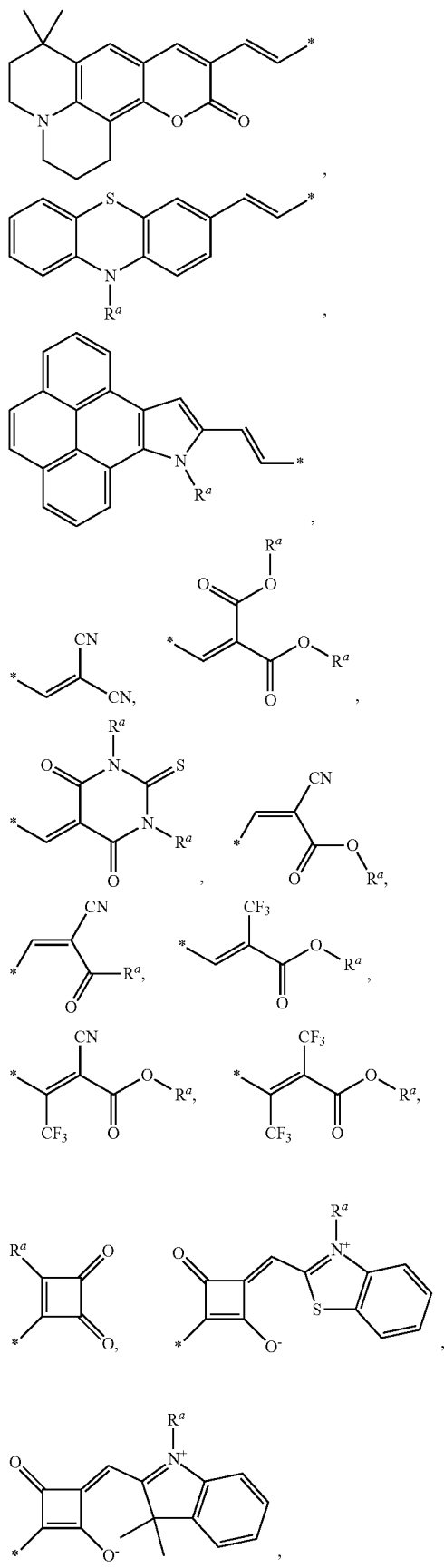

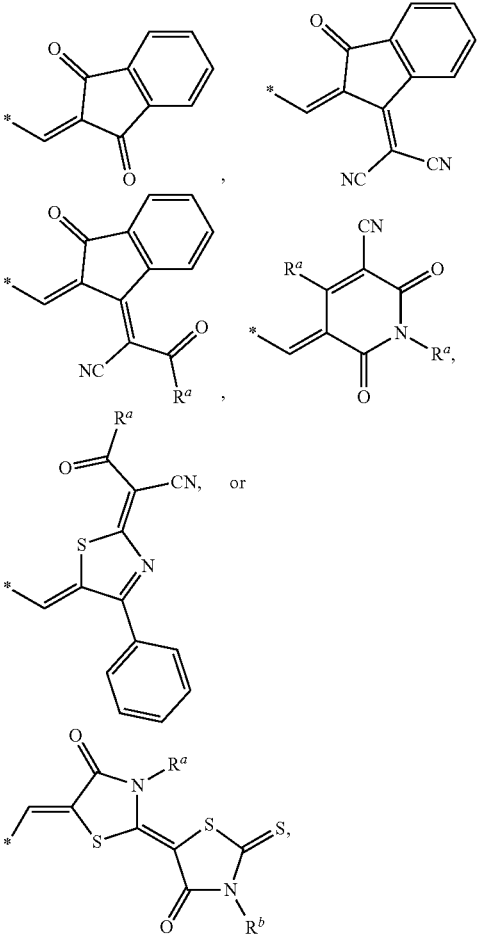

R<sup>a</sup>, R<sup>b</sup> are independently of each other aryl or heteroaryl, each having from 4 to 30 ring atoms and being unsubstituted or substituted with one or more groups R or $R^1$, $Ar^{12}$ is aryl or heteroaryl, each having from 4 to 30 ring atoms and being unsubstituted or substituted with one or more groups $R^1$, R is alkyl with 1 to 30 C atoms which is straight-chain, branched or cyclic, and is unsubstituted, substituted with one or more F or Cl atoms or CN groups, or perfluorinated, and in which one or more C atoms are optionally replaced by —O—, —S—, —C(O)—, —C(S)—, —SiR°R°°—, —NR°R°°—, —CHR°=CR°°— or —C≡C— such that O- and/or S-atoms are not directly linked to each other, R°, R°° have the meanings given in claim 1, R', R", R''' independently of each other have one of the meanings of R°, e, f, g, h, i, k, l, m are independently of each other 0 or 1, with at least one of e, f, g, h, i, k, l, m being 1, t is 1, 2 or 3.

14. The compound of claim 13, wherein:

R°, R°° denote, independently of each other, H or $C_{1-20}$ alkyl.

15. A composition or polymer blend comprising one or more compounds according to claim 1 and one or more compounds or polymers having one or more of semiconducting, charge transport, hole or electron transport, hole or electron blocking, electrically conducting, photoconducting or light emitting properties.

16. The composition or polymer blend according to claim 15, characterized in that it comprises one or more n-type organic semiconductor compounds.

17. The composition or polymer blend according to claim 16, characterized in that the n-type organic semiconductor compound is a fullerene or substituted fullerene.

18. An optical, electrooptical, electronic, photoactive, electroluminescent or photoluminescent device, or a component of such a device or an assembly comprising such a device or component, comprising a composition or polymer blend according to claim 15.

19. A semiconducting, charge transport, electrically conducting, photoconducting, photoactive or light emitting material or a dye or a pigment, comprising a composition or polymer blend of claim 15.

20. An optical, electrooptical, electronic, photoactive, electroluminescent or photoluminescent device, or a component of such a device or an assembly comprising such a device or component, comprising a compound according to claim 1.

21. A semiconducting, charge transport, electrically conducting, photoconducting, photoactive or light emitting material or a dye or a pigment, comprising a compound of claim 1.

22. An optical, electrooptical, electronic, photoactive, electroluminescent or photoluminescent device, or a component thereof, or an assembly comprising it, which comprises a semiconducting, charge transport, electrically conducting, photoconducting or light emitting material according to claim 21.

23. The optical, electrooptical, electronic, photoactive, electroluminescent or photoluminescent device according to claim 22, which is selected from organic field effect transistors (OFET), organic thin film transistors (OTFT), organic light emitting diodes (OLED), organic light emitting transistors (OLET), organic photovoltaic devices (OPV), organic photodetectors (OPD), organic solar cells, dye sensitized solar cells (DSSC), laser diodes, Schottky diodes, photoconductors, photodetectors and thermoelectric devices.

24. The component according to claim 22, which is selected from charge injection layers, charge transport layers, interlayers, planarising layers, antistatic films, polymer electrolyte membranes (PEM), conducting substrates and conducting patterns.

25. The assembly according to claim 22, which is selected from integrated circuits (IC), radio frequency identification (RFID) tags, security devices, flat panel displays, backlights of flat panel devices, electrophotographic devices, electrophotographic recording devices, organic memory devices, sensor devices, biosensors and biochips.

26. The device according to claim 22, which is an OFET, OTFT, OPD, OLED, bulk heterojunction (BHJ) OPV device or inverted BHJ OPV device.

27. A formulation comprising one or more compounds according to claim 1 and further comprising one or more organic solvents.

28. An optical, electrooptical, electronic, photoactive, electroluminescent or photoluminescent device, or a component thereof, or an assembly comprising it, which is prepared using a formulation according to claim 27.

29. The compound of claim 1, wherein:

$R^o$, $R^{oo}$ independently of each other denote H or alkyl with 1 to 12 C-atoms, and $X^o$ denotes F, Cl or Br.

30. A compound comprising one or more divalent units of formula I

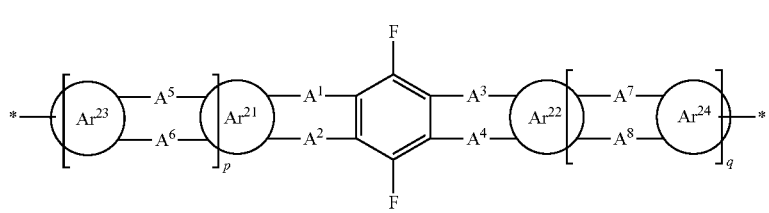

wherein one of $A^1$ and $A^2$ is X and the other is a single bond, one of $A^3$ and $A^4$ is X and the other is a single bond, one of $A^5$ and $A^6$ is X and the other is a single bond, one of $A^7$ and $A^8$ is X and the other is a single bond, X is, on each occurrence identically or differently, $CR^1R^2$, $C=CR^1R^2$, $SiR^1R^2$, $GeR^1R^2$, C=O or $NR^1$, $R^1$, $R^2$ denote, independently of each other and on each occurrence identically or differently, straight-chain or branched alkyl, alkoxy, sulfanylalkyl, sulfonylalkyl, alkylcarbonyl, alkoxycarbonyl and alkylcarbonyloxy, each having 1 to 30 C atoms and being unsubstituted or substituted by one or more F atoms without being perfluorinated, or aryl or heteroaryl, each of which is optionally substituted with one or more groups $R^S$ and has 4 to 30 ring atoms, p, q are independently of each other 0, 1 or 2, $Ar^{21}$, $Ar^{22}$, $Ar^{23}$, $Ar^{24}$ denote, independently of each other, and on each occurrence identically or differently, an aromatic or heteroaromatic group, each of which is monocyclic or polycyclic, has 4 to 20 ring atoms, and is optionally substituted by one or more groups $R^S$, $R^S$ denotes, on each occurrence identically or differently, straight-chain or branched alkyl, alkoxy, sulfanylalkyl, sulfonylalkyl, alkylcarbonyl, alkoxycarbonyl and alkylcarbonyloxy, each having 1 to 30 C atoms and being unsubstituted or substituted by one or more F atoms without being perfluorinated, or aryl or heteroaryl, each of which is optionally substituted with one or more groups $R^S$ and has 4 to 30 ring atoms, $R^o$, $R^{oo}$ independently of each other denote H or optionally substituted $C_{1-40}$ carbyl or hydrocarbyl, $Y^1$, $Y^2$ independently of each other denote H, F, Cl or CN, and $X^o$ denotes halogen.

31. A compound comprising one or more divalent units selected from the following subformulae I1-I22:

115                                                                 116
I1
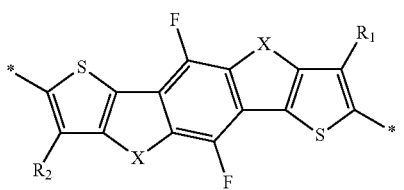
I2
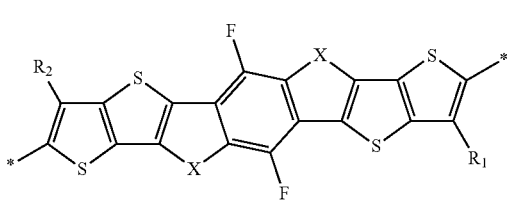
I3
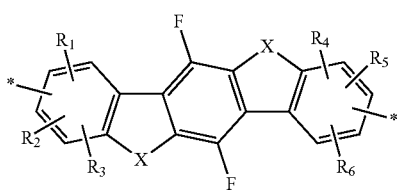
I4
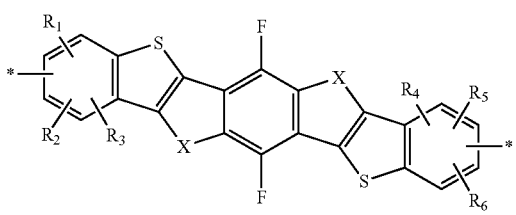
I5
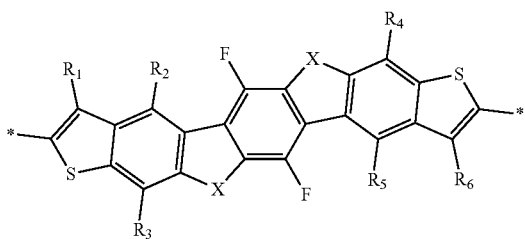
I6
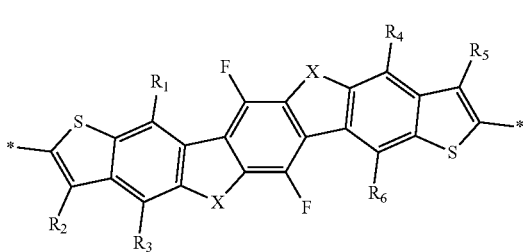
I7
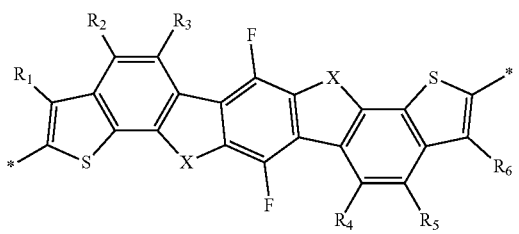
I8
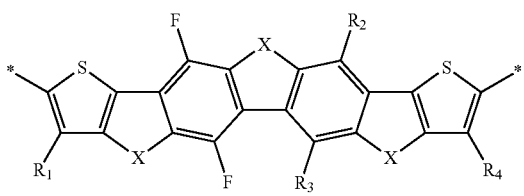
I9
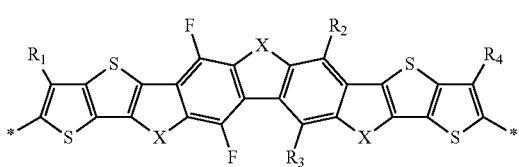
I10
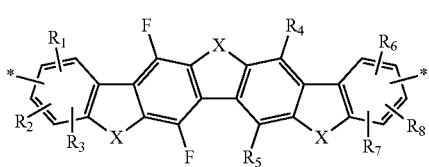
I11
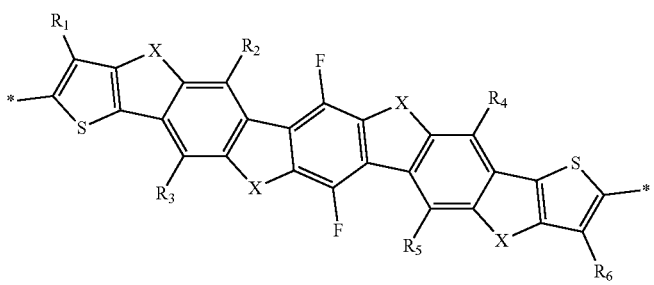
I12
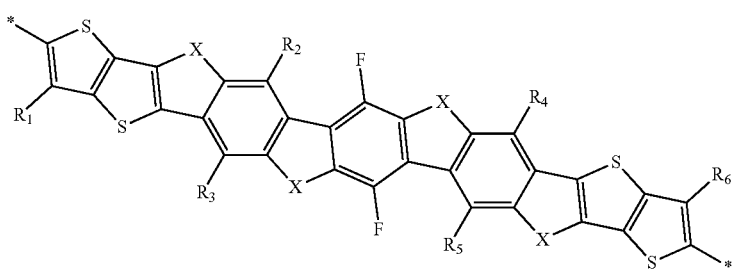

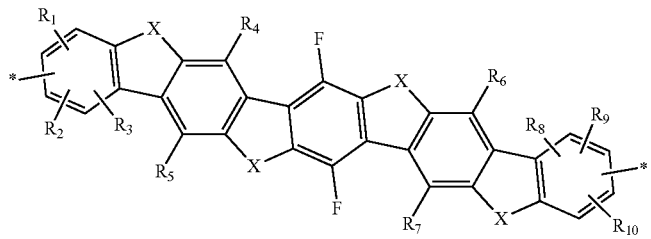
I13
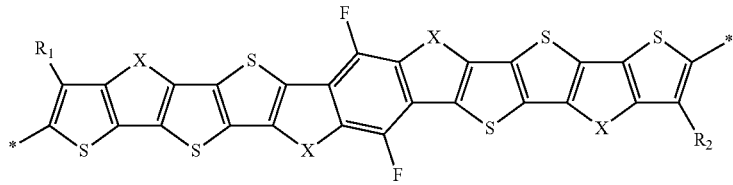
I14
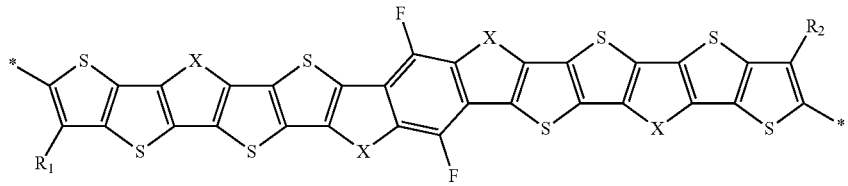
I15
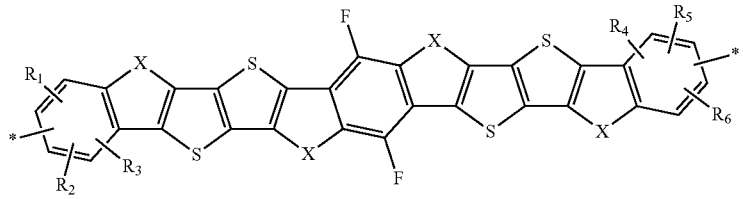
I16
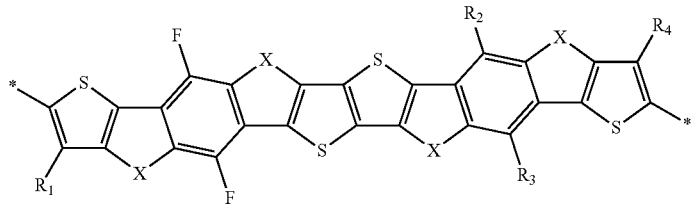
I17
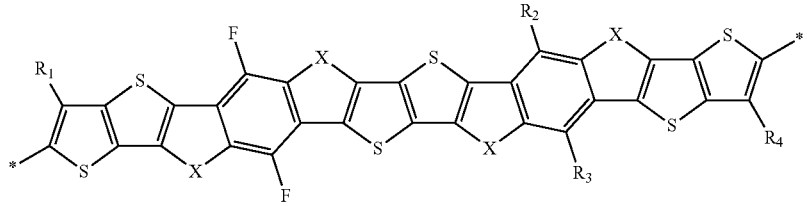
I18
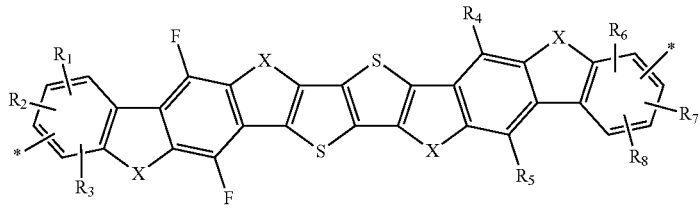
I19

-continued

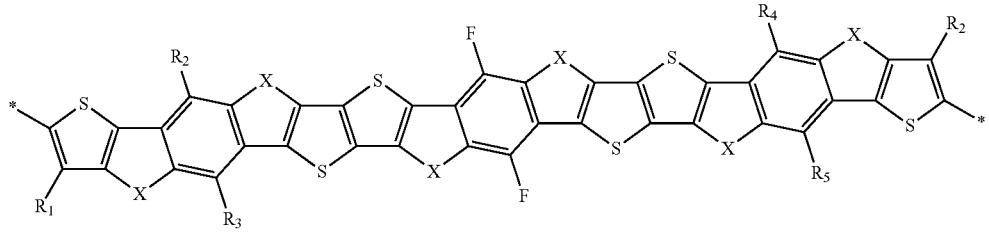

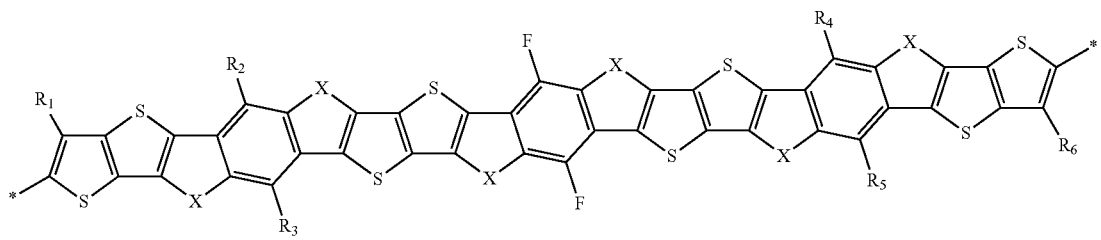

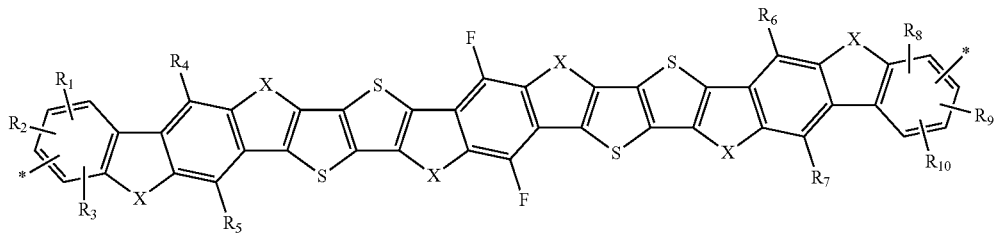

wherein X is CR¹R², C=CR¹R², SiR¹R² or GeR¹R², R¹ and R² denote, independently of each other and on each occurrence identically or differently, H, halogen or straight chain, branched or cyclic alkyl group with 1 to 50 C atoms in which one or more non-adjacent CH₂ groups are optionally replaced, in each case independently from one another, by —O—, —S—, —C(O)—, —C(O)O—, —O—C(O)—, —O—CO(O)—O—, —SO₂—, —SO₃—, —NR⁰—, —SiR⁰R⁰⁰—, —CF—, —CR⁰=CR⁰⁰—, —CY¹=CY²— or —C≡C— in such a manner that O and/or S atoms are not linked directly to one another, and in which one or more, but not all, H atoms are optionally replaced by F, Cl, Br, I or CN, or denotes monocyclic or polycyclic aryl or heteroaryl, each of which is optionally substituted with one or more groups R^S and has 4 to 30 ring atoms, and R³, R⁴, R⁵, R⁶, R⁷ and R⁸ independently have one of the meanings given for R¹.

32. A monomer of formula VIa or VIb

R²³—(Ar¹)ₐ—U—(Ar²)꜀—R²⁴  (VIa)

R²³—U—(Ar¹)ₐ—U—R²⁴  (VIb)

wherein

U is a unit of formula I

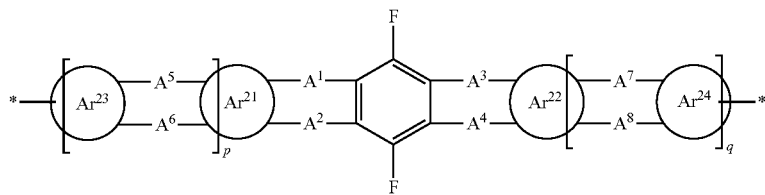

wherein
one of A¹ and A² is X and the other is a single bond,
one of A³ and A⁴ is X and the other is a single bond,
one of A⁵ and A⁶ is X and the other is a single bond,
one of A⁷ and A⁸ is X and the other is a single bond,
X is, on each occurrence identically or differently, CR¹R², C=CR¹R², SiR¹R², GeR¹R², C=O or NR¹,
R¹, R² denote, independently of each other and on each occurrence identically or differently, H, halogen or straight chain, branched or cyclic alkyl group with 1 to 50 C atoms in which one or more non-adjacent CH₂ groups are optionally replaced, in each case independently from one another, by —O—, —S—, —C(O)—, —C(O)O—, —O—C(O)—, —O—CO(O)—O—, —SO₂—, —SO₃—, —NR⁰—, —SiR⁰R⁰⁰—, —CF₂—, —CR⁰CR⁰⁰—, —CY¹=CY²— or —C≡C— in such a manner that O and/or S atoms are not linked directly to one another, and in which one or more, but not all, H atoms are optionally replaced by F, Cl, Br, I or CN, or denotes monocyclic or polycyclic aryl or heteroaryl, each of which is optionally substituted with one or more groups $R^S$ and has 4 to 30 ring atoms, p, q are independently of each other 0, 1 or 2, $Ar^{21}, Ar^{22}, Ar^{23}, Ar^{24}$ denote, independently of each other, and on each occurrence identically or differently, an aromatic or heteroaromatic group, each of which is monocyclic or polycyclic, has 4 to 20 ring atoms, and is optionally substituted by one or more groups $R^S$, $R^S$ denotes, on each occurrence identically or differently, F, Br, Cl, —CN, —NC, —NCO, —NCS, —OCN, —SCN, —C(O)NR$^O$R$^{OO}$, —C(O)X$^O$, —C(O)R$^O$, —C(O)OR$^O$, —NH$_2$, —NR$^O$R$^{OO}$, —SH, —SR$^O$, —SO$_3$H, —SO$_2$R$^O$, —OH, —NO$_2$, —CF$_3$, —SF$_5$, optionally substituted silyl, carbyl or hydrocarbyl with 1 to 40 C atoms that is optionally substituted and optionally comprises one or more hetero atoms, $R^O, R^{OO}$ independently of each other denote H or optionally substituted $C_{1-40}$ carbyl or hydrocarbyl, $Y^1, Y^2$ independently of each other denote H, F, Cl or CN, $X^O$ denotes halogen, $Ar^1, Ar^2$ are, on each occurrence identically or differently, and independently of each other, aryl or heteroaryl that is different from U, and is optionally substituted, a, b are on each occurrence identically or differently 0, 1 or 2, and $R^{23}$ and $R^{24}$ are, independently of each other, selected from the group consisting of H, Cl, Br, I, O-tosylate, O-triflate, O-mesylate, O-nona-flate, —SiMe$_2$F, —SiMeF$_2$, —O—SO$_2$Z$^1$, —B(OZ$^2$)$_2$, —CZ$^3$=C(Z$^3$)$_2$, —C≡CH, —C≡CSi(Z$^1$)$_3$, —ZnX$^O$ and —Sn(Z$^4$)$_3$, wherein $X^O$ is halogen, $Z^{1-4}$ are selected from the group consisting of alkyl and aryl, each being optionally substituted, and two groups $Z^2$ may also together form a cycloboronate group with 2 to 20 C atoms together with the B and O atoms.

33. The monomer of claim 32, which is selected from the following formulae $R^{23}$—U—$R^{24}$     VI1

$R^{23}$—Ar$^1$—U—$R^{24}$     VI2

$R^{23}$—U—Ar$^2$—$R^{24}$     VI3

$R^{23}$—U—Ar$^1$—U—$R^{24}$     VI4

$R^{23}$—Ar$^1$—U—Ar$^2$—$R^{24}$     VI5

$R^{23}$—U-$A^c$-$R^{24}$     VI6 wherein $A^c$ is an aryl or heteroaryl group that is different from U and $Ar^{1-3}$, has 5 to 30 ring atoms, is optionally substituted by one or more groups $R^S$, and is selected from aryl or heteroaryl groups having electron acceptor properties, wherein $R^S$ is on each occurrence identically or differently F, Br, Cl, —CN, —NC, —NCO, —NCS, —OCN, —SCN, —C(O)NR$^O$R$^{OO}$, —C(O)X$^O$, —C(O)R$^O$, —NH$_2$, —NR$^O$R$^{OO}$, —SH, —SR$^O$, —SO$_3$H, —SO$_2$R$^O$, —OH, —NO$_2$, —CF$_3$, —SF$_5$, optionally substituted silyl, carbyl or hydrocarbyl with 1 to 40 C atoms that is optionally substituted and optionally comprises one or more hetero atoms.

34. A process of preparing a conjugated polymer by coupling one or more monomers of formula VIa or VIb $R^{23}$—(Ar$^1$)$_a$—U—(Ar$^2$)$_c$—$R^{24}$     VIa $R^{23}$—U—(Ar$^1$)$_a$—U—$R^{24}$     VIb wherein U is a unit of formula I

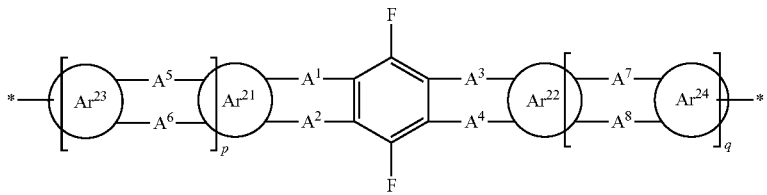

wherein one of $A^1$ and $A^2$ is X and the other is a single bond, one of $A^3$ and $A^4$ is X and the other is a single bond, one of $A^5$ and $A^6$ is X and the other is a single bond, one of $A^7$ and $A^8$ is X and the other is a single bond, X is, on each occurrence identically or differently, $CR^1R^2$, $C=CR^1R^2$, $SiR^1R^2$, $GeR^1R^2$, C=O or $NR^1$, $R^1, R^2$ denote, independently of each other and on each occurrence identically or differently, H, halogen or straight chain, branched or cyclic alkyl group with 1 to 50 C atoms in which one or more non-adjacent CH$_2$ groups are optionally replaced, in each case independently from one another, by —O—, —S—, —C(O)—, —C(O)O—, —O—C(O)—, —O—CO(O)—O—, —SO$_2$—, —SO$_3$—, —NR$^O$—, —SiR$^O$R$^{OO}$—, —CF$_2$—, —CR$^O$=CR$^{OO}$—, —CY$^1$=CY$^2$— or —C≡C— in such a manner that O and/or S atoms are not linked directly to one another, and in which one or more, but not all, H atoms are optionally replaced by F, Cl, Br, I or CN, or denotes monocyclic or polycyclic aryl or heteroaryl, each of which is optionally substituted with one or more groups $R^S$ and has 4 to 30 ring atoms, p, q are independently of each other 0, 1 or 2, $Ar^{21}, Ar^{22}, Ar^{23}, Ar^{24}$ denote, independently of each other, and on each occurrence identically or differently, an aromatic or heteroaromatic group, each of which is monocyclic or polycyclic, has 4 to 20 ring atoms, and is optionally substituted by one or more groups $R^S$, $R^S$ denotes, on each occurrence identically or differently, F, Br, Cl, —CN, —NC, —NCO, —NCS, —OCN, —SCN, —C(O)NR$^O$R$^{OO}$, —C(O)X$^O$, —C(O)R$^O$, —C(O)OR$^O$, —NH$_2$, —NR$^O$R$^{OO}$, —SH, —SR$^O$, —SO$_3$H, —SO$_2$R$^O$, —OH, —NO$_2$, —CF$_3$, —SF$_5$, optionally substituted silyl, carbyl or hydrocarbyl with 1 to 40 C atoms that is optionally substituted and optionally comprises one or more hetero atoms, $R^O, R^{OO}$ independently of each other denote H or optionally substituted $C_{1-40}$ carbyl or hydrocarbyl, $Y^1$, $Y^2$ independently of each other denote H, F, Cl or CN, $X^0$ denotes halogen, $Ar^1$, $Ar^2$ are, on each occurrence identically or differently, and independently of each other, aryl or heteroaryl that is different from U, and is optionally substituted, a, b are on each occurrence identically or differently 0, 1 or 2, and $R^{23}$ and $R^{24}$ are selected from Cl, Br, I, $-B(OZ^2)_2$ and $-Sn(Z^4)_3$, with each other and/or with one or more monomers selected from the following formulae $$R^{23}-(Ar^1)_a-A^c-(Ar^2)_c-R^{24} \qquad \text{VIII}$$

$$R^{23}-Ar^1-R^{24} \qquad \text{IX}$$

$$R^{23}-Ar^3-R^{24} \qquad \text{X}$$

$$R^{23}-A^c-R^{24} \qquad \text{XI}$$

wherein $Ar^1$, $Ar^2$, $Ar^3$, are independently as defined for $Ar^1$, $Ar^2$, a and c are independently as defined for a, b, $A^c$ is an aryl or heteroaryl group that is different from U and $Ar^{1-3}$, has 5 to 30 ring atoms, is optionally substituted by one or more groups $R^S$, and is selected from aryl or heteroaryl groups having electron acceptor properties, wherein $R^S$ is on each occurrence identically or differently F, Br, Cl, $-CN$, $-NC$, $-NCO$, $-NCS$, $-OCN$, $-SCN$, $-C(O)NR^0R^{00}$, $-C(O)X^0$, $-C(O)R^0$, $-NH_2$, $-NR^0R^{00}$, $-SH$, $-SR^0$, $-SO_3H$, $-SO_2R^0$, $-OH$, $-NO_2$, $-CF_3$, $-SF_5$, optionally substituted silyl, carbyl or hydrocarbyl with 1 to 40 C atoms that is optionally substituted and optionally comprises one or more hetero atoms, and $R^{23}$ and $R^{24}$ are selected from Cl, Br, I, $-B(OZ^2)_2$ and $-Sn(Z^4)_3$, in an aryl-aryl coupling reaction.

* * * * *